United States Patent
Altschul et al.

(10) Patent No.: US 12,227,727 B2
(45) Date of Patent: Feb. 18, 2025

(54) MEDICAL DEVICES AND USES THEREOF

(71) Applicant: Pop Test Oncology LLC, Cliffside Park, NJ (US)

(72) Inventors: Randice Lisa Altschul, Cliffside Park, NJ (US); Neil David Theise, New York, NY (US); Razvan Andrei Ene, Vimercate (IT); Myron Rapkin, Indianapolis, IN (US); Rebecca O'Brien, Shell Knob, MO (US)

(73) Assignee: Pop Test Oncology LLC, Cliffside Park, NJ (US)

( * ) Notice: Subject to any disclaimer, the term of this patent is extended or adjusted under 35 U.S.C. 154(b) by 865 days.

(21) Appl. No.: 16/992,705

(22) PCT Filed: Feb. 27, 2019

(86) PCT No.: PCT/US2019/019744
§ 371 (c)(1),
(2) Date: Aug. 13, 2020

(87) PCT Pub. No.: WO2019/168913
PCT Pub. Date: Sep. 6, 2019

(65) Prior Publication Data
US 2021/0162125 A1 Jun. 3, 2021

Related U.S. Application Data

(60) Provisional application No. 62/723,071, filed on Aug. 27, 2018, provisional application No. 62/655,367, (Continued)

(51) Int. Cl.
*A61M 5/142* (2006.01)
*A61B 5/00* (2006.01)
(Continued)

(52) U.S. Cl.
CPC ......... *C12M 23/42* (2013.01); *A61B 5/14546* (2013.01); *A61B 5/4845* (2013.01);
(Continued)

(58) Field of Classification Search
CPC .............. A61M 1/3486; A61M 1/3489; A61M 1/1601; A61M 1/1603; A61M 1/3623;
(Continued)

(56) References Cited

U.S. PATENT DOCUMENTS 5,270,192 A * 12/1993 Li ........................... C12M 29/10
435/174
5,290,684 A * 3/1994 Kelly ...................... A61F 2/022
435/29

(Continued)

OTHER PUBLICATIONS

Ghazali, Farah Afiqa Mohd, Md Nazibul Hasan, Tariq Rehman, Marwan Nafea, Mohamed Sultan Mohamed Ali, and Kenichi Takahata. "MEMS actuators for biomedical applications: a review." Journal of Micromechanics and Microengineering 30, No. 7 (2020): 073001.*

(Continued)

*Primary Examiner* — Adam Marcetich
(74) *Attorney, Agent, or Firm* — Jeffrey A Schwab; Doug Gilbert; Stefan Knirr

(57) ABSTRACT

The present invention provides for a method and apparatus for inserting and using dermal interstitial sensors in, for example, an analyte monitoring system, and for injecting active pharmaceutical ingredients, a bio-artificial organ device, and detection of a protein biomarker.

4 Claims, 11 Drawing Sheets

Specification includes a Sequence Listing.

Related U.S. Application Data filed on Apr. 10, 2018, provisional application No. 62/650,165, filed on Mar. 29, 2018, provisional application No. 62/636,196, filed on Feb. 28, 2018.

(51) Int. Cl.

| | |
|---|---|
| A61B 5/145 | (2006.01) |
| A61M 1/16 | (2006.01) |
| A61M 1/34 | (2006.01) |
| A61M 1/36 | (2006.01) |
| C12M 1/00 | (2006.01) |
| C12M 1/12 | (2006.01) |
| C12M 3/00 | (2006.01) |
| C12M 3/06 | (2006.01) |
| G01N 33/574 | (2006.01) |
| A61B 5/021 | (2006.01) |
| A61B 34/20 | (2016.01) |

(52) U.S. Cl.
CPC ......... *A61B 5/4866* (2013.01); *A61M 1/3486* (2014.02); *A61M 1/3489* (2014.02); *A61M 1/3623* (2022.05); *A61M 5/14244* (2013.01); *A61M 5/14276* (2013.01); *C12M 3/065* (2013.01); *C12M 3/067* (2013.01); *C12M 23/44* (2013.01); *C12M 23/58* (2013.01); *C12M 25/14* (2013.01); *G01N 33/57438* (2013.01); *A61B 5/021* (2013.01); *A61B 2034/2055* (2016.02); *A61M 1/1601* (2014.02); *A61M 2202/0413* (2013.01); *A61M 2202/0415* (2013.01); *A61M 2205/18* (2013.01); *A61M 2205/3584* (2013.01); *A61M 2205/50* (2013.01); *A61M 2210/1071* (2013.01); *A61M 2210/1082* (2013.01); *C12M 3/06* (2013.01)

(58) Field of Classification Search
CPC .. A61M 2210/1071; A61M 2210/1082; C12M 3/06; C12M 3/065; C12M 3/067; C12M 23/42; C12M 23/44; C12M 21/08; C12M 25/14; C12M 23/16; C12M 23/34
See application file for complete search history.

(56) References Cited

U.S. PATENT DOCUMENTS

| | | | | |
|---|---|---|---|---|
| 5,368,555 | A * | 11/1994 | Sussman | A61M 1/3472 |
| | | | | 435/1.1 |
| 5,522,394 | A | 6/1996 | Zurbrugg | |
| 5,873,835 | A | 2/1999 | Hastings et al. | |
| 6,111,520 | A | 8/2000 | Allen et al. | |
| 6,277,277 | B1 * | 8/2001 | Jacobi | B01D 61/30 |
| | | | | 210/240 |
| 6,278,379 | B1 | 8/2001 | Allen et al. | |
| 6,372,495 | B1 * | 4/2002 | Flendrig | C12M 25/02 |
| | | | | 435/395 |
| 6,409,674 | B1 | 6/2002 | Brockway et al. | |
| 6,472,200 | B1 * | 10/2002 | Mitrani | C12M 35/08 |
| | | | | 435/284.1 |
| 6,475,639 | B2 | 11/2002 | Shahinpoor et al. | |
| 6,517,482 | B1 | 2/2003 | Elden et al. | |
| 6,673,596 | B1 | 1/2004 | Sayler et al. | |
| 6,675,030 | B2 | 1/2004 | Ciurczak et al. | |
| 6,802,811 | B1 | 10/2004 | Slepian | |
| 6,836,678 | B2 | 12/2004 | Tu | |
| 6,855,115 | B2 | 2/2005 | Fonseca et al. | |
| 6,954,662 | B2 | 10/2005 | Freger et al. | |
| 7,184,810 | B2 | 2/2007 | Caduff et al. | |
| 7,299,080 | B2 | 11/2007 | Acosta et al. | |
| 7,303,875 | B1 | 12/2007 | Bock et al. | |
| 2003/0196947 | A1 * | 10/2003 | Gundrum | B01D 35/306 |
| | | | | 210/473 |
| 2003/0223969 | A1 * | 12/2003 | Humes | A61P 3/10 |
| | | | | 424/140.1 |
| 2005/0130254 | A1 * | 6/2005 | Park | G01N 33/5082 |
| | | | | 435/40.5 |
| 2005/0277839 | A1 | 12/2005 | Alderman et al. | |
| 2007/0048734 | A1 * | 3/2007 | Park | G01N 33/5011 |
| | | | | 435/4 |
| 2007/0105224 | A1 * | 5/2007 | Lin | C12N 15/86 |
| | | | | 435/456 |
| 2008/0164220 | A1 * | 7/2008 | Hoshino | B01D 35/12 |
| | | | | 210/232 |
| 2009/0236272 | A1 * | 9/2009 | Zerger | C02F 9/20 |
| | | | | 210/137 |
| 2009/0275072 | A1 * | 11/2009 | Imran | C07K 14/78 |
| | | | | 435/293.1 |
| 2011/0287071 | A1 * | 11/2011 | Mitrani | C12N 5/0068 |
| | | | | 435/395 |
| 2012/0183944 | A1 * | 7/2012 | Taylor | A61K 35/407 |
| | | | | 435/395 |
| 2013/0196375 | A1 * | 8/2013 | Strobbe | C12M 29/10 |
| | | | | 210/198.2 |
| 2013/0288375 | A1 * | 10/2013 | Zhang | C12N 5/0671 |
| | | | | 435/395 |
| 2013/0333178 | A1 * | 12/2013 | Hilal-Alnaqbi | B01D 69/082 |
| | | | | 29/402.04 |
| 2014/0017215 | A1 * | 1/2014 | Ayares | A61L 27/3604 |
| | | | | 435/325 |
| 2014/0087454 | A1 * | 3/2014 | Li | C12M 3/00 |
| | | | | 435/289.1 |
| 2015/0076066 | A1 * | 3/2015 | Zink | A61M 1/3434 |
| | | | | 435/297.1 |
| 2015/0175950 | A1 * | 6/2015 | Hirschel | C12M 41/32 |
| | | | | 435/235.1 |
| 2016/0058933 | A1 * | 3/2016 | Ballantyne | G06F 21/565 |
| | | | | 210/85 |
| 2016/0256672 | A1 * | 9/2016 | Arumugaswami | C12N 5/067 |
| 2016/0333295 | A1 * | 11/2016 | Baker | C12M 23/16 |
| 2017/0240854 | A1 * | 8/2017 | Machluf | C12M 25/14 |
| 2017/0252701 | A1 * | 9/2017 | Nosrati | A61M 1/3417 |
| 2018/0117235 | A1 * | 5/2018 | Zhou | C12M 29/04 |
| 2018/0117236 | A1 * | 5/2018 | Zhou | C12M 41/18 |

OTHER PUBLICATIONS

Chase, C. Peter, and August O. Weilbach. "Viking GC/MS mechanisms design and performance." In JPL 10th Aerospace Mech. Symp. 1976.*

Rushneck, D. R., A. V. Diaz, D. W. Howarth, J. Rampacek, K. W. Olson, W. D. Dencker, P. Smith et al. "Viking gas chromatograph-mass spectrometer." Review of Scientific Instruments 49, No. 6 (1978): 817-834.*

Barakat, Omar, et al. "Use of decellularized porcine liver for engineering humanized liver organ." Journal of surgical research 173.1 (2012): e11-e25. (Year: 2012).*

Sabetkish, Shabnam, et al. "Whole‐organ tissue engineering: Decellularization and recellularization of three‐dimensional matrix liver scaffolds." Journal of biomedical materials research Part A 103.4 (2015): 1498-1508. (Year: 2015).*

Baptista, Pedro M., et al. "The use of whole organ decellularization for the generation of a vascularized liver organoid." Hepatology 53.2 (2011): 604-617. (Year: 2011).*

Bao, Ji, et al. "Construction of a portal implantable functional tissue-engineered liver using perfusion-decellularized matrix and hepatocytes in rats." Cell transplantation 20.5 (2011): 753-766. (Year: 2011).*

Liu, H., You, S., Rong, Y. et al. The newly established human liver cell line: a potential cell source for the bioartificial liver in the future. Human Cell 26, 155-161 (2013). https://doi.org/10.1007/s13577-013-0068-5.*

Durick, K. et al., Cellular biosensors for drug discovery, Biosensors & Bioelectronics, 2001, 587-592.

Hagleitner, C. et al., Smart single-chip gas sensor microsystem, Nature, Nov. 15, 2001, 293-295, vol. 14.

(56) References Cited

OTHER PUBLICATIONS

Mok, W. et al., Recent progress in nucleic acid aptamer-based biosensors and bioassays, Sensors, 2008, 7050-7084, vol. 8.
Morrison, D.W.G. et al., Clinical applications of micro- and nanoscale biosensors, Biomedical Nanostructures, 2008, John Wiley & Sons, Inc., 439-460.
Held, M. et al., Microbial biosensor array with transport mutants of *Escherichia coli* K12 for the simultaneous determination of mono- and disaccharides, Biosensors and Bioelectronics, Dec. 2002, 1089-1094, vol. 17, issues 11-12.
Yang, C. et al., Configurable hardware-efficient interface circuit for multi-sensory microsystems, IEEE Sensors, 2006, Oct. 22-25, 2006, 41-44.
Snow, E.S., Chemical detection with a single-walled carbon nanotube capacitor, Science, Mar. 25, 2005, 1942-1945, vol. 307.
Yang, C.K. et al., Field emission as transducer for sub-micron and nano resonators, IEEE Sensors, 2006.
Yusa, G. et al., Controlled multiple quantum coherences of nuclear spins in a nanometre-scale device, Nature, 2005, 1001-1005.

\* cited by examiner

Fig. 9

SEQ ID NO: 1 gtagatctga aggactgggg tttctgacca cacagcagtg ctgctgacac agaggacagt ttctctacca ggtctgtcac
ctaaagcagt gaaaatggcc agaggatccg tgtctgacga agaaatgatg gagctcagag aggcttttgc caaagttgat
accgatggca aaggatacat cagctgcaat gagctaaatg acttgttcaa ggccgcctgc ctgcctctgc ctgggtaccg
agtgagagaa atcacagaaa acctgatggc cacaggtgat ctggaccaag atggaaagat cagctttgat gagtttatca
aggtcttcca tggcttaaaa agcaccgagg ttgccaaaac cttccgaaaa gctatcaaca agaaggaagg gatctgtgcg
attggcggca cctctgagca gtccagcgtt ggtacccagc actcttactc agaggaagaa aagtatgcct ttgtcaactg
gataaacaaa gccctggaga atgaccccga ctgccggcat gtcatcccca tgaaccccaa caccgacgat ctcttcaatg
ctgtaggcga tggcatagtt ctttgtaaaa tgatcaacct tctgtgcca gacacgattg acgagagaac gatcaacaag
aaaaagctca caccattcac cattcaggaa aacttgaact tggctctgaa ctctgcctct gccattgggt gccacgtggt
taatataggg gccgaggacc tgaaggaggg caagccttac ctggtcctgg gacttttgtg gcaagtcatc aagattgggt
tgtttgctga cattgaactc agcagaaatg aagctctgat tgctcttttg agagaaggag agagcctaga ggatttgatg
aagttgtctc ctgaagaact cctgctgcgg tgggctaact accacctaga aaacgcaggc tgcaccaaaa tcaccaactt
cagcaccgac atcaaggact ccaaagctta ttaccacctg ctcgagcaag tggctccaaa aggagatgaa gaagggatcc
cggcggttgt gattgacatg tcaggactga gggagaagga tgacatccag agggcagagt gcatgctgca acaggcggag
aggctgggct gccggcagtt tgtcacagct actgatgttg tccgagggaa ccccaagttg aacctggcct tcattgccaa
cctcttcaac aaataccctg ccttacacaa accagagaac caggacattg actgggggc tctcgaaggt gagacgaggg
aagagcggac cttcaggaat tggatgaact ccctgggcgt taacccgcgc gtcaatcact tgtacagcga cttatcggat
gccttagtca tcttccagct ctatgagaag atcaaagtcc ctgttgattg gaacagagta aacaagcctc catccccaa
gctgggggc aatatgaaaa agctggagaa ctgtaattat gcagtggacc tggggaagaa tcaagctaaa ttctccctgg
ttggcatcgc aggacaagac ctcaatgaag gaaaccgaac tctcacgctg gcattggttt ggcagctcat gagaaggtac
acactgaata tcctggaaga tatcggaggt ggacagaagg tcaatgatga cattattgtc aactgggtga atacgacctt
gaaggaggca cagaaaagct catccattgc tagcttcaag gacccaaaga tcagtaccag cctcccggtt ctggatctca
ttgacgccat tcagccaggt tccataaact atgaccttct aaagacagaa aactggatg atgaagagaa actcaacaat
gcaaagtatg ccatctctat ggccagaaaa atcggagcaa gggtgtacgc cctcccagaa gacctggttg aagtgaaccc
caaaatggtc atgacagtgt ttgcctgcct catggggaaa gggatgaaga gggtgtaagt cccagaggag taagccagaa
atcgacacag acaagcctga gggggtcagc acatggtgct cccaggatgc agaggaccat tcaagccatt gcaaagtcct
gaaccttgga gacattattt gaaattcaca catttcttca gccaagtagc ttctgctata attagcaata cgtgcttctc ttttgttgtt
gttttttcag aagatgtact cgcctacaaa ttttttttt attctttgaa agtctacc

Fig. 10

SEQ ID NO: 2

Met Ala Arg Gly Ser Val Ser Asp Glu Glu Met Met Glu Leu Arg Glu Ala Phe Ala Lys Val Asp Thr
Asp Gly Lys Gly Tyr Ile Ser Cys Asn Glu Leu Asn Asp Leu Phe Lys Ala Ala Cys Leu Pro Leu Pro Gly
Tyr Arg Val Arg Glu Ile Thr Glu Asn Leu Met Ala Thr Gly Asp Leu Asp Gln Asp Gly Lys Ile Ser Phe
Asp Glu Phe Ile Lys Val Phe His Gly Leu Lys Ser Thr Glu Val Ala Lys Thr Phe Arg Lys Ala Ile Asn Lys
Lys Glu Gly Ile Cys Ala Ile Gly Gly Thr Ser Glu Gln Ser Ser Val Gly Thr Gln His Ser Tyr Ser Glu Glu
Glu Lys Tyr Ala Phe Val Asn Trp Ile Asn Lys Ala Leu Glu Asn Asp Pro Asp Cys Arg His Val Ile Pro
Met Asn Pro Asn Thr Asp Asp Leu Phe Asn Ala Val Gly Asp Gly Ile Val Leu Cys Lys Met Ile Asn Leu
Ser Val Pro Asp Thr Ile Asp Glu Arg Thr Ile Asn Lys Lys Lys Leu Thr Pro Phe Thr Ile Gln Glu Asn Leu
Asn Leu Ala Leu Asn Ser Ala Ser Ala Ile Gly Cys His Val Val Asn Ile Gly Ala Glu Asp Leu Lys Glu Gly
Lys Pro Tyr Leu Val Leu Gly Leu Leu Trp Gln Val Ile Lys Ile Gly Leu Phe Ala Asp Ile Glu Leu Ser Arg
Asn Glu Ala Leu Ile Ala Leu Leu Arg Glu Gly Glu Ser Leu Glu Asp Leu Met Lys Leu Ser Pro Glu Glu
Leu Leu Leu Arg Trp Ala Asn Tyr His Leu Glu Asn Ala Gly Cys Thr Lys Ile Thr Asn Phe Ser Thr Asp
Ile Lys Asp Ser Lys Ala Tyr Tyr His Leu Leu Glu Gln Val Ala Pro Lys Gly Asp Glu Glu Gly Ile Pro Ala
Val Val Ile Asp Met Ser Gly Leu Arg Glu Lys Asp Asp Ile Gln Arg Ala Glu Cys Met Leu Gln Gln Ala
Glu Arg Leu Gly Cys Arg Gln Phe Val Thr Ala Thr Asp Val Val Arg Gly Asn Pro Lys Leu Asn Leu Ala
Phe Ile Ala Asn Leu Phe Asn Lys Tyr Pro Ala Leu His Lys Pro Glu Asn Gln Asp Ile Asp Trp Gly Ala
Leu Glu Gly Glu Thr Arg Glu Glu Arg Thr Phe Arg Asn Trp Met Asn Ser Leu Gly Val Asn Pro Arg Val
Asn His Leu Tyr Ser Asp Leu Ser Asp Ala Leu Val Ile Phe Gln Leu Tyr Glu Lys Ile Lys Val Pro Val Asp
Trp Asn Arg Val Asn Lys Pro Pro Tyr Pro Lys Leu Gly Gly Asn Met Lys Lys Leu Glu Asn Cys Asn Tyr
Ala Val Asp Leu Gly Lys Asn Gln Ala Lys Phe Ser Leu Val Gly Ile Ala Gly Gln Asp Leu Asn Glu Gly
Asn Arg Thr Leu Thr Leu Ala Leu Val Trp Gln Leu Met Arg Arg Tyr Thr Leu Asn Ile Leu Glu Asp Ile
Gly Gly Gly Gln Lys Val Asn Asp Asp Ile Ile Val Asn Trp Val Asn Thr Thr Leu Lys Glu Ala Gln Lys Ser
Ser Ser Ile Ala Ser Phe Lys Asp Pro Lys Ile Ser Thr Ser Leu Pro Val Leu Asp Leu Ile Asp Ala Ile Gln
Pro Gly Ser Ile Asn Tyr Asp Leu Leu Lys Thr Glu Asn Leu Asp Asp Glu Glu Lys Leu Asn Asn Ala Lys
Tyr Ala Ile Ser Met Ala Arg Lys Ile Gly Ala Arg Val Tyr Ala Leu Pro Glu Asp Leu Val Glu Val Asn Pro
Lys Met Val Met Thr Val Phe Ala Cys Leu Met Gly Lys Gly Met Lys Arg Val

SEQUENCE LISTING

<160> NUMBER OF SEQ ID NOS: 2

<210> SEQ ID NO 1
<211> LENGTH: 2227
<212> TYPE: DNA
<213> ORGANISM: Mus musculus

<400> SEQUENCE: 1

| | | | | | |
|---|---|---|---|---|---|
| gtagatctga | aggactgggg | tttctgacca | cacagcagtg | ctgctgacac | agaggacagt | 60 |
| ttctctacca | ggtctgtcac | ctaaagcagt | gaaaatggcc | agaggatccg | tgtctgacga | 120 |
| agaaatgatg | gagctcagag | aggcttttgc | caaagttgat | accgatggca | aggatacat | 180 |
| cagctgcaat | gagctaaatg | acttgttcaa | ggccgcctgc | ctgcctctgc | ctgggtaccg | 240 |
| agtgagagaa | atcacagaaa | acctgatggc | acaggtgat | ctggaccaag | atggaaagat | 300 |
| cagctttgat | gagtttatca | aggtcttcca | tggcttaaaa | agcaccgagg | ttgccaaaac | 360 |
| cttccgaaaa | gctatcaaca | agaaggaagg | gatctgtgcg | attggcggca | cctctgagca | 420 |
| gtccagcgtt | ggtacccagc | actcttactc | agaggaagaa | aagtatgcct | ttgtcaactg | 480 |
| gataaacaaa | gccctggaga | atgacccga | ctgccggcat | gtcatcccca | tgaaccccaa | 540 |
| caccgacgat | ctcttcaatg | ctgtaggcga | tggcatagtt | ctttgtaaaa | tgatcaacct | 600 |
| tctgtgccag | acacgattga | cgagagaacg | atcaacaaga | aaaagctcac | accattcacc | 660 |
| attcaggaaa | acttgaactt | ggctctgaac | tctgcctctg | ccattgggtg | ccacgtggtt | 720 |
| aatatagggg | ccgaggacct | gaaggagggc | aagccttacc | tggtcctggg | acttttgtgg | 780 |
| caagtcatca | agattgggtt | gtttgctgac | attgaactca | gcagaaatga | agctctgatt | 840 |
| gctcttttga | gagaaggaga | gagcctagag | gatttgatga | agttgtctcc | tgaagaactc | 900 |
| ctgctgcggt | gggctaacta | ccacctagaa | aacgcaggct | gcaccaaaat | caccaacttc | 960 |
| agcaccgaca | tcaaggactc | caaagcttat | taccacctgc | tcgagcaagt | ggctccaaaa | 1020 |
| ggagatgaag | aagggatccc | ggcggttgtg | attgacatgt | caggactgag | ggagaaggat | 1080 |
| gacatccaga | gggcagagtg | catgctgcaa | caggcggaga | ggctgggctg | ccggcagttt | 1140 |
| gtcacagcta | ctgatgttgt | ccgagggaac | cccaagttga | acctggcctt | cattgccaac | 1200 |
| ctcttcaaca | ataccctgc | cttacacaaa | ccagagaacc | aggacattga | ctggggggct | 1260 |
| ctcgaaggtg | agacgaggga | agagcggacc | ttcaggaatt | ggatgaactc | cctgggcgtt | 1320 |
| aacccgcgcg | tcaatcactt | gtacagcgac | ttatcggatg | ccttagtcat | cttccagctc | 1380 |
| tatgagaaga | tcaaagtccc | tgttgattgg | aacagagtaa | acaagcctcc | ataccccaag | 1440 |
| ctgggggca | atatgaaaaa | gctggagaac | tgtaattatg | cagtggacct | ggggaagaat | 1500 |
| caagctaaat | tctccctggt | tggcatcgca | ggacaagacc | tcaatgaagg | aaaccgaact | 1560 |
| ctcacgctgg | cattggtttg | gcagctcatg | agaaggtaca | cactgaatat | cctggaagat | 1620 |
| atcgaggtg | gacagaaggt | caatgatgac | attattgtca | actgggtgaa | tacgaccttg | 1680 |
| aaggaggcac | agaaaagctc | atccattgct | agcttcaagg | acccaaagat | cagtaccagc | 1740 |
| ctcccggttc | tggatctcat | tgacgccatt | cagccaggtt | ccataaacta | tgaccttcta | 1800 |
| aagacagaaa | acctggatga | tgaagagaaa | ctcaacaatg | caaagtatgc | catctctatg | 1860 |

```
gccagaaaaa tcggagcaag ggtgtacgcc ctcccagaag acctggttga agtgaacccc   1920
aaaatggtca tgacagtgtt tgcctgcctc atggggaaag ggatgaagag ggtgtaagtc   1980
ccagaggagt aagccagaaa tcgacacaga caagcctgag ggggtcagca catggtgctc   2040
ccaggatgca gaggaccatt caagccattg caaagtcctg aaccttggag acattatttg   2100
aaattcacac atttcttcag ccaagtagct tctgctataa ttagcaatac gtgcttctct   2160
tttgttgttg ttttttcaga agatgtactc gcctacaaat ttttttttta ttctttgaaa   2220
gtctacc                                                             2227

<210> SEQ ID NO 2
<211> LENGTH: 627
<212> TYPE: PRT
<213> ORGANISM: Mus musculus

<400> SEQUENCE: 2

Met Ala Arg Gly Ser Val Ser Asp Glu Glu Met Met Glu Leu Arg Glu
1               5                   10                  15

Ala Phe Ala Lys Val Asp Thr Asp Gly Lys Gly Tyr Ile Ser Cys Asn
            20                  25                  30

Glu Leu Asn Asp Leu Phe Lys Ala Ala Cys Leu Pro Leu Pro Gly Tyr
        35                  40                  45

Arg Val Arg Glu Ile Thr Glu Asn Leu Met Ala Thr Gly Asp Leu Asp
    50                  55                  60

Gln Asp Gly Lys Ile Ser Phe Asp Glu Phe Ile Lys Val Phe His Gly
65                  70                  75                  80

Leu Lys Ser Thr Glu Val Ala Lys Thr Phe Arg Lys Ala Ile Asn Lys
                85                  90                  95

Lys Glu Gly Ile Cys Ala Ile Gly Gly Thr Ser Glu Gln Ser Ser Val
            100                 105                 110

Gly Thr Gln His Ser Tyr Ser Glu Glu Lys Tyr Ala Phe Val Asn
        115                 120                 125

Trp Ile Asn Lys Ala Leu Glu Asn Asp Pro Asp Cys Arg His Val Ile
    130                 135                 140

Pro Met Asn Pro Asn Thr Asp Asp Leu Phe Asn Ala Val Gly Asp Gly
145                 150                 155                 160

Ile Val Leu Cys Lys Met Ile Asn Leu Ser Val Pro Asp Thr Ile Asp
                165                 170                 175

Glu Arg Thr Ile Asn Lys Lys Lys Leu Thr Pro Phe Thr Ile Gln Glu
            180                 185                 190

Asn Leu Asn Leu Ala Leu Asn Ser Ala Ser Ala Ile Gly Cys His Val
        195                 200                 205

Val Asn Ile Gly Ala Glu Asp Leu Lys Glu Gly Lys Pro Tyr Leu Val
    210                 215                 220

Leu Gly Leu Leu Trp Gln Val Ile Lys Ile Gly Leu Phe Ala Asp Ile
225                 230                 235                 240

Glu Leu Ser Arg Asn Glu Ala Leu Ile Ala Leu Leu Arg Glu Gly Glu
                245                 250                 255

Ser Leu Glu Asp Leu Met Lys Leu Ser Pro Glu Glu Leu Leu Leu Arg
            260                 265                 270

Trp Ala Asn Tyr His Leu Glu Asn Ala Gly Cys Thr Lys Ile Thr Asn
        275                 280                 285

Phe Ser Thr Asp Ile Lys Asp Ser Lys Ala Tyr Tyr His Leu Leu Glu
    290                 295                 300
```

-continued

```
Gln Val Ala Pro Lys Gly Asp Glu Glu Gly Ile Pro Ala Val Val Ile
305                 310                 315                 320

Asp Met Ser Gly Leu Arg Glu Lys Asp Asp Ile Gln Arg Ala Glu Cys
            325                 330                 335

Met Leu Gln Gln Ala Glu Arg Leu Gly Cys Arg Gln Phe Val Thr Ala
            340                 345                 350

Thr Asp Val Val Arg Gly Asn Pro Lys Leu Asn Leu Ala Phe Ile Ala
            355                 360                 365

Asn Leu Phe Asn Lys Tyr Pro Ala Leu His Lys Pro Glu Asn Gln Asp
            370                 375                 380

Ile Asp Trp Gly Ala Leu Glu Gly Glu Thr Arg Glu Glu Arg Thr Phe
385                 390                 395                 400

Arg Asn Trp Met Asn Ser Leu Gly Val Asn Pro Arg Val Asn His Leu
            405                 410                 415

Tyr Ser Asp Leu Ser Asp Ala Leu Val Ile Phe Gln Leu Tyr Glu Lys
            420                 425                 430

Ile Lys Val Pro Val Asp Trp Asn Arg Val Asn Lys Pro Pro Tyr Pro
            435                 440                 445

Lys Leu Gly Gly Asn Met Lys Lys Leu Glu Asn Cys Asn Tyr Ala Val
    450                 455                 460

Asp Leu Gly Lys Asn Gln Ala Lys Phe Ser Leu Val Gly Ile Ala Gly
465                 470                 475                 480

Gln Asp Leu Asn Glu Gly Asn Arg Thr Leu Thr Leu Ala Leu Val Trp
                485                 490                 495

Gln Leu Met Arg Arg Tyr Thr Leu Asn Ile Leu Glu Asp Ile Gly Gly
            500                 505                 510

Gly Gln Lys Val Asn Asp Asp Ile Ile Val Asn Trp Val Asn Thr Thr
            515                 520                 525

Leu Lys Glu Ala Gln Lys Ser Ser Ile Ala Ser Phe Lys Asp Pro
    530                 535                 540

Lys Ile Ser Thr Ser Leu Pro Val Leu Asp Leu Ile Asp Ala Ile Gln
545                 550                 555                 560

Pro Gly Ser Ile Asn Tyr Asp Leu Leu Lys Thr Glu Asn Leu Asp Asp
            565                 570                 575

Glu Glu Lys Leu Asn Asn Ala Lys Tyr Ala Ile Ser Met Ala Arg Lys
            580                 585                 590

Ile Gly Ala Arg Val Tyr Ala Leu Pro Glu Asp Leu Val Glu Val Asn
            595                 600                 605

Pro Lys Met Val Met Thr Val Phe Ala Cys Leu Met Gly Lys Gly Met
    610                 615                 620

Lys Arg Val
625
```

MEDICAL DEVICES AND USES THEREOF

CROSS-REFERENCE TO RELATED APPLICATIONS

This application claims the benefit of PCT Application No. PCT/US2019/019744, filed Feb. 27, 2019, which claims the benefit of U.S. Ser. No. 62/636,196, filed Feb. 28, 2018; U.S. Ser. No. 62/650,165, filed Mar. 29, 2018; U.S. Ser. No. 62/655,367, filed Apr. 10, 2018; and U.S. Ser. No. 62/723,071, filed Aug. 27, 2018, the entirety of which are incorporated herein by reference.

BACKGROUND OF THE INVENTION

The present invention provides for a method and apparatus for inserting and using dermal interstitial sensors in, for example, an analyte monitoring system, and for injecting active pharmaceutical ingredients.

The dermis, the second layer of the skin, is usually described as a densely compacted layer of fibroconnective tissue through which course small branches of arteries, veins and lymphatic vessels, as well as nerves. Recent data obtained by correlation of histologic findings with in vivo microscopy reveal that this appearance of densely compacted fibroconnective tissue is artefactual; the living dermis is a cavernous interstitial sinus supported and defined by an extensive lattice of thick collagen bundles lined on one side by a CD34+ cell without endothelial ultrastructure: perhaps a modified endothelial cell, a fibroblast, and/or mesenchymal stem cell. The interstitial fluid flowing in this space in living tissue is derived from serum and may be considered pre-lymph. Molecules in the serum reach the interstitial fluid within minutes of change, as demonstrated by intravascular infusion of fluorescein whereby, within minutes, in vivo microscopy reveals fluorescence of the dermal interstitial sinus.

This lymph, imprecisely termed "interstitial fluid", contains biomolecules, such as proteins, glycoproteins, sugars, lipids, etc, as they are found in the blood. Indwelling sensors that can detect such molecules are known, in particular glucose sensors that are inserted into the skin. However, inventors and users of these devices are imprecise in their identification of the "interstitial fluid" that is being monitored and of the precise location and anatomy of device insertion. These devices often decline in signal integrity over time and also have skin irritative effects that require regular replacement, perhaps due to the invasion of deeper tissues generating tissue reactions. The lack of understanding of the anatomy of the dermal lymphatic sinus has led to such imprecisions which this present invention alleviates.

This present invention describes a method of placement of such a sensor so that it lies entirely within the dermal lymphatic sinus or reticular dermis, providing consistent and maximal exposure to lymph. The device would be positioned by first inserting a trocar at a shallow angle into the dermal lymphatic sinus or reticular dermis, removal of the obturator component leaving the hollow cannula. Lymph draining from the cannula confirms correct placement and then the sensor device is slipped through the cannula and cannula is removed, leaving the device in place, fully within the dermal lymphatic sinus or reticular dermis. This device may be connected to:

An external device for registering and transmission of data from the sensor to nearby or distant monitors;

An internal device sufficiently small to also lay contained within the dermal lymphatic sinus;

An internal device surgically embedded in soft tissues beneath the dermis, i.e., in the subcutis.

The device to which the sensor communicates can receive signals through direct physical connections or wireless digital signaling, such as, but not limited to, Bluetooth.

The sensor can measure glucose or other analytes, such as ions, proteins and glycoproteins, lipids, other sugars, ingested nutrients or drugs/toxins or their metabolites.

The sensor can be coated with biologic or synthetic molecules (including, but not limited to chitosan, hyaluronic acid, Teflon, glycosaminoglycans such as Heparin, Heparin sulfate, chondroitin sulfate etc. that are antifibrotic and/or anti-inflammatory around the sensor leading to consistent signaling over time greater than is achieved through current, imprecisely placed sensors.

Uses for the device would include continuous monitoring of blood sugar in patients with type 1 or type 2 diabetes mellitus, electrolyte imbalances in individuals in exposed environmental conditions such as soldiers and extreme sports participants, uric acid levels in patients with gout, etc.

According to the American Diabetes Association in 2012, 29.1 million Americans, or 9.3% of the population, had diabetes.

Approximately 1.25 million American children and adults have type 1 diabetes.

Undiagnosed: Of the 29.1 million, 21.0 million were diagnosed, and 8.1 million were undiagnosed.

Prevalence in Seniors: The percentage of Americans age 65 and older remains high, at 25.9%, or 11.8 million seniors (diagnosed and undiagnosed).

New Cases: 1.4 million Americans are diagnosed with diabetes every year.

Pre-diabetes: In 2012, 86 million Americans age 20 and older had prediabetes; this is up from 79 million in 2010.

Deaths: Diabetes remains the 7th leading cause of death in the United States in 2010, with 69,071 death certificates listing it as the underlying cause of death, and a total of 234,051 death certificates listing diabetes as an underlying or contributing cause of death.

Diabetes in Youth

About 208,000 Americans under age 20 are estimated to have diagnosed diabetes, approximately 0.25% of that population.

Diabetes was the seventh leading cause of death in the United States in 2010 based on the 69,071 death certificates in which diabetes was listed as the underlying cause of death. In 2010, diabetes was mentioned as a cause of death in a total of 234,051 certificates.

Diabetes may be underreported as a cause of death. Studies have found that only about 35% to 40% of people with diabetes who died had diabetes listed anywhere on the death certificate and about 10% to 15% had it listed as the underlying cause of death.

The key to good health for a diabetic is to monitor their blood glucose levels regularly to be able to maintain a healthy lifestyle. Blood sticks have long been the method for daily monitoring but they are painful and burdensome which leads to a lack of compliance among those who are at risk.

A finger-prick blood glucose check gives you only one number in time. It's hard to know: Is your blood glucose rising, falling, or staying steady? A continuous glucose monitor (CGM), however, records hundreds of readings a day.

A CGM consists of three parts: a small under-the-skin sensor that measures glucose levels in what is known as interstitial fluid; a transmitter that attaches to the sensor and transfers data; and a receiver that displays glucose information and stores data. The sensor measures glucose every five minutes or so.

According to Diabetes Self-Management; although studies find that the sensor readings usually are close to fingerstick numbers, there can be significant differences (up to 15%). It takes glucose around 5-10 minutes to move from blood into tissue fluid, or back, so the CGMS measures lag behind what's really happening in your blood if things are changing rapidly.

The CGM doesn't replace fingersticks. You still have to check your blood glucose level 2 to 4 times a day to keep the CGMS calibrated. Calibration is an ongoing job with CGMS. They also say you should not make "treatment decisions" (like taking extra insulin) based on a CGMS reading without taking a conventional blood glucose reading first.

Acceptance of CGMS in the diabetic community has been slow because of a number of reasons. They are not reliable due to variabilities in placement of the sensor, the fat level of the individual and the high costs which are not always covered by insurance.

The present invention provides for multiple means for a variety of health monitoring that are a reliable means of placement of CGM and similar type interstitial sensors and the use of a digital device that can alternatively read a test strip in a more rapid low cost means of monitoring glucose among other constituents.

Artificial Liver

A collaboration between the disciplines of engineering, medicine, veterinary medicine and pharmacy, aspects of the present disclosure provide for a Bio-Artificial Liver as a pharmaceutical device and methods to manufacture and use the device and system. 3D liver culture system: To predict toxicity and other safety variables as well as the effectiveness of new products, traditional testing of chemicals, consumer products, medical devices, and new drugs has involved the use of animals. The idea that all new drugs and products should be tested for safety in animal studies before being approved for human testing is based on the assumption that animals will respond to drug tests like "little humans." However, the past decades have shown that animals respond differently and unpredictably and therefore the studies are unreliable, at best. The testing of just one compound, be it a potential drug or toxic chemical, can involve using up to 800 animals and cost over $6 million. Currently, we are entering a new era in drug discovery in which the development of non-animal methods, to improve the efficiency and reduce costs, will be vital to the future survival of pharmaceutical companies. New methods, such as computer modeling, virtual drug trials, micro-dosing technologies, and human cell and tissue methods ("organ-on-a-chip" technologies), are being developed that will necessarily change the landscape of this industry.

The 3D liver scaffold culture system is developed as an early stage testing tool for drug companies to use before investing time and money in in vivo models. Once the drug company has gone through its initial "hit-to-lead" high-throughput screening, our living human hepatic tissue could be utilized to speed up the development of candidate compounds, allowing the company to examine the tissue using a variety of assays, such as histological, immune-histological and molecular markers. Unlike other recent technologies that are being evaluated, such as 3D tissue printing, the scaffolds of the preset disclosure hold key components necessary to fully mimic hepatic tissue. Three-dimensional bioprinted tissue can be a powerful tool for making headway in areas where traditional animal models and 2D cell-culture methods aren't able to meet. However, the system of the present invention will allow pharma to go beyond bio-printing technology, giving them more and better avenues to filter and reject an ineffective or dangerous drug in a matter of weeks to months. This will shorten the drug discovery process—which can take up to six years—and results in significant savings.

Currently, most organotypic models have focused on drug safety and toxicity with few adaptations to mimic other aspects of NAFLD or NASH. In this context, the liver microenvironment includes a number of circulating risk factors that can be incorporated into the media formulation in vitro to promote a NASH-relevant phenotype. These risk factors include endotoxin, inflammatory cytokines, growth factors, glucose, insulin, free fatty acid (FFA) and alcohol exposure. In particular, FFAs are known to induce a lipotoxic phenotype and are the most commonly used stimuli in NAFLD in vitro models, as they may also lead to increased levels of additional factors, such as inflammatory cytokines.

The major problem with the above listed models is that they are missing the actual hepatic micro-environment. Utilizing a decellularized hepatic scaffold will allow the culture of all the cell types found in the liver in an environments the cells are familiar with allowing them to set-up a true or more realistic hepatic culture system The 3D liver scaffold culture system is composed of native liver matrices from humans repopulated with native liver cells. Our unique liver scaffold culture system will be developed as an early stage testing tool for drug companies to use before investing time and money into expensive in vivo models. Once the drug company has gone through its initial "hit-to-lead" high-throughput screening, our living human hepatic tissue could be utilized to speed up the development of candidate compounds, allowing the company to examine the tissue using a variety of assays, such as histological, immune-histological and molecular markers. Unlike other recent technologies that are being evaluated, such as 3D tissue printing which uses artificial matrices, our natural decellurized liver scaffolds still hold key signaling components (e.g., GAG-proteins, HGF, IGF-BP3) which are necessary to fully mimic the hepatic microenvironment as seen in the natural liver setting.

Our human hepatocyte 3D culture system will become a powerful tool in making progress in areas where the current methods of animal testing, 2D cell-culture or liver-slice methods aren't able to accomplish. In the present system of drug discovery, the current testing procedures are unable to define toxicity at a histological level, except for the animal model. Our 3D liver culture system can be grown utilizing human hepatic cells or virtually any species of hepatic cells, which will also enable veterinarian medicine pharma companies to develop specific assays for drugs to be administered to animals. Our human 3D liver culture system will allow pharmaceutical companies to go beyond the current technology, giving them enhanced prospects to filter and reject an ineffective or dangerous drug in a shorter period of time. This will shorten the drug discovery process—which can take up to six years—which will result in significant savings for the drug companies allowing them the ability to provide a safer and more effective drug to consumers.

Utilizing the previously discussed methods to induce NASH in conjunction with our 3D culture system will more closely resemble living and functioning hepatic tissue. This simple schematic illustrates how the culture will work. Unlike current in vitro models where the media flows outside the hepatic cells, which only provides a small percentage of effectiveness. The proposed construct will work in a manner similar to how the native liver functions. In our model the media will pass over the hepatic tissue allowing direct contact, which mimics the natural liver environment. By implementing this difference we feel the functional output of our system will be superior in function and mobility.

The premise behind the device is that each column will be independent of each other and the final construct will allow each column the ability to be placed in and/or taken out at any given moment. This allows each column to be independently developed, allowing each column to be developed in accordance with the research specifications. Because of the modular design several different disease models can be studied independently or in combination. For example one, two or three columns can be developed as a NASH model, while other columns can be developed with pancreatic tissue (Type-1 Diabetes or hyperglycemic). In addition, other columns can be normal heptic tissue giving the researcher the ability to study how the diseased state can affect the normal state.

In terms of personal medicine, cancerous cells can be cultured in the columns and each column can be isolated with each column receiving a different treatment protocol allowing oncologist to personalize the treatment for the patient. Our device can also be designed with columns of cancerous cell in combination with normal tissue and study metastatic movement Also, in personalized medicine, patients suffering from metabolic disorders such as Glycogen Storage Disease; Wilson Disease and Alagille Syndrome. Here a geneticist/molecular biologist can actually perform gene therapy studies and understand how effectively the construct infected the cells and how efficiently the transduced cells are performing. This approach can be utilized in a couple of different ways, first the approach will allow the clinicians to utilize the best viral construct to treat the patient, the second application could be to transduce the cells in the columns and then isolate the transduced cells and perform a cellular transplant. The device will hold approximately 700 grams of hepatic tissue at 100 percent functionality, meaning with this much tissue there will be more than enough cells for therapeutic protocols. (approximately 10×7 hepatocytes per gram of liver)

Unlike other current 3D cell/tissue growth technologies, (e.g. organ-on-a-chip, tissue specific organoids) this 3D scaffold approach allows for histologic assessments to be performed, with 200-300 histological sections obtainable from each 1-2 mm thick scaffold. This histologic analysis can be applied to toxicity models or to naturally occurring disease models.

IHoP

The pancreas has 2 main types of cells: Exocrine cells: Most of the cells in the pancreas form the exocrine glands and ducts. The exocrine glands make pancreatic enzymes that are released into the intestines to help you digest foods (especially fats). Endocrine cells: Endocrine cells make up a much smaller percentage of the cells in the pancreas. These cells are in small clusters called islets (or islets of Langerhans). These islets make important hormones like insulin and glucagon (which help control blood sugar levels), and release them directly into the blood. The exocrine cells and endocrine cells of the pancreas form different types of tumors. It's very important to know if the cancer in the pancreas is an exocrine or endocrine cancer. They have distinct risk factors and causes, have different signs and symptoms, are diagnosed with different tests, are treated in different ways, and have different outlooks. Exocrine cancers are by far the most common type of pancreas cancer. If you are told you have pancreatic cancer, it's most likely an exocrine pancreatic cancer.

About 95% of the cancers formed in the pancreas are Pancreatic adenocarcinoma with less common exocrine cancers including, adenosquamous carcinomas, squamous cell carcinomas, signet ring cell carcinomas, undifferentiated carcinomas, and undifferentiated carcinomas with giant cells. Tumors of the endocrine pancreas are uncommon, making up less than 5% of all pancreatic cancers. As a group, they are often called pancreatic neuroendocrine tumors (NETs) or islet cell tumors. The American Cancer Society's estimates that approximately 55,440 people (29,200 men and 26,240 women) will be diagnosed with pancreatic cancer in 2018 in the US. Of these diagnoses about 44,330 people (23,020 men and 21,310 women) will die from the disease. That is about an 85% to 99% mortality rate depending upon the stage of the cancer when diagnosed. The disease accounts for about 3% of all cancers in the US and about 7% of all cancer deaths.

A new protein called Islet Homeostasis Protein (IHoP) plays an important role in maintaining pancreatic stability and recent studies have shown that dysregulation of this protein leads to a variety of pancreatic disorders, such as Type-1 Diabetes Mellitus (T1D), insulitis and cancer. The current disclosure can be utilized as a non-invasive method to determine the health of the pancreas. These methods can include but not limited to blood test, saliva test, urine test and so forth. These methods will be able to utilize in a clinical setting to give clinicians an earlier and better way in diagnosing pancreatic diseases.

The disclosure provides a simple clinical test performed in a medical facility (e.g., hospital, doctor's office, clinic, emergency room), at home or in workplace health maintenance/screening settings to determine if the patient is suffering from pancreatic dysfunction, including neoplasia/malignancy, diabetes mellitus or pre-diabetes, or other inflammatory conditions of the pancreas.

All references cited herein are incorporated herein by reference in their entireties.

BRIEF SUMMARY OF THE INVENTION

Aspects of the present disclosure provide a device for guiding the injection of at least one active pharmaceutical agent into the skin of a subject, the device comprising: a housing that is adapted for placement on the outer skin of the subject and comprising: at least one insertion port contiguous with an insertion channel that is formed at a predetermined angle within said housing, said channel having an opening that is adapted to rest against the skin; an ultraviolet illuminator for illumination of a fluorescent material that is previously positioned within the reticular dermis of the subject that is located underneath said housing; a camera comprising a focus adjustment, said camera capturing an image of the skin, including the reticular dermis, located beneath said housing; and a display that permits a user to view said image when passing an needle through said channel such that a tip of said needle is positioned within the reticular dermis for delivering the at least one active agent through the needle and into the reticular dermis. Aspects of the present disclosure provide a device wherein said camera comprises a wireless transponder and said display is located remotely of said housing, said transponder providing said image to said remotely located display wherein said camera is adapted to couple to said display for displaying said image thereon. Aspects of the present disclosure provide a device wherein the camera is a confocal microscope. Aspects of the present disclosure provide a device wherein the focal plane of the camera is adjusted via the display. Aspects of the present disclosure provide a device wherein the display is a smartphone. Aspects of the present disclosure provide a device wherein said predetermined angle is a shallow angle. Aspects of the present disclosure provide a device wherein the at least one active agent is selected from the group consisting of PT150, TPR-1, OR-1, MR-1, TCY1, PT157, PT158, PT159, PT160, PT162, PT163, PT164, PT165, PT166, PT167, BSI201, Olaparib, ABT-888, AG014699, CEP 9722, MK 4827, KU-0059436, LT-673,3-aminobenzamide, iniparib, olaparib, rucaparib, veliparib, or CEP 9722, combinations thereof, and pharmaceutically acceptable salts thereof.

Aspects of the present disclosure provide a method of delivering at least one active pharmaceutical agent into the skin of a subject, the method comprising: administering an imaging agent to a subject, wherein the imaging agent collects in the target area of the subject's skin, wherein the target area is the reticular dermis of the skin of the subject, further wherein the imaging agent is a fluorescent agent; providing a device for guiding the implanting of an needle within the skin of the subject, the device comprising: a housing comprising: at least one insertion port contiguous with an insertion channel that is formed at a predetermined angle within said housing, said channel having an opening that is adapted to rest against the skin; an ultraviolet illuminator for illumination a fluorescent material that is previously positioned within the reticular dermis of the subject that is located underneath said housing; a camera comprising a focus adjustment, said camera capturing an image of the skin, including the reticular dermis, located beneath said housing; and a display, associated with said housing, that permits a user to view said image when passing an needle through said channel such that a tip of said needle is positioned within the reticular dermis for delivering the sampler therein; applying the imaging device to the skin of the subject; illuminating the skin with the illuminator, thereby causing the imaging agent to fluoresce; using the display to adjust the focus of the confocal microscope into the plane of the fluorescence; inserting a needle through the at least one insertion port into the sample area of the subject, wherein the user uses a display to follow the insertion of the needle, wherein when the tip of the needle is in the plane of the focus, the needle is in the target area; and injecting the at least one active agent into the reticular dermis. Aspects of the present disclosure provide a method wherein the method further comprises: inserting the sensor device through the needle, wherein the needle is a hollow cannula, into the target area, thereby delivering the at least active agent to the target area of the skin of the subject. Aspects of the present disclosure provide a method wherein the imaging is obtained in real time.

Aspects of the present disclosure provide a method wherein the imaging is obtained episodically.

Aspects of the present disclosure provide a method wherein the active agent is selected from the group consisting of PT150, TPR-1, OR-1, MR-1, TCY1, PT157, PT158, PT159, PT160, PT162, PT163, PT164, PT165, PT166, PT167, BSI201, Olaparib, ABT-888, AG014699, CEP 9722, MK 4827, KU-0059436, LT-673,3-aminobenzamide, iniparib, olaparib, rucaparib, veliparib, or CEP 9722, combinations thereof, and pharmaceutically acceptable salts thereof.

Aspects of the present disclosure provide a method wherein the sensor device is attached to the skin of the subject at an area selected from the group consisting of the upper arm, abdomen, waist, torso, and back of the subject. Aspects of the present disclosure provide a method wherein the sensor device is configured to provide data to an external device for registering and transmission of data from the sensor to monitors. Aspects of the present disclosure provide a method wherein the sensor device further comprises an internal device sufficiently small to also lay contained within the target area. Aspects of the present disclosure provide a method wherein the sensor device is configured to communicate data through direct physical connection to a processing device. Aspects of the present disclosure provide a method wherein the sensor device is configured to communicate data through a wireless signal. Aspects of the present disclosure provide a method wherein the wireless signal is Bluetooth. Aspects of the present disclosure provide a method wherein the sensor device can measure an analyte selected from the group consisting of glucose, ions, proteins, glycoproteins, lipids, sugars, ingested nutrients, or drugs, toxins, metabolites of drugs, metabolites of toxins, and combinations thereof. Aspects of the present disclosure provide a method wherein the sensor device is coated with biologic or synthetic molecule selected from the group consisting of chitosan, hyaluronic acid, Teflon, glycosaminoglycans, Heparin, Heparin sulfate, chondroitin sulfate. Aspects of the present disclosure provide a method wherein the coating is antifibrotic and/or anti-inflammatory around the sensor leading to consistent signaling over time greater than is achieved through current, imprecisely placed sensors. Aspects of the present disclosure provide a bio-artificial organ device for processing of a biological fluid comprising: an inflow port for ingress of a biological fluid; a distribution chamber which optionally includes a pump; at least one column in fluid communication with the distribution chamber wherein said at least one column can receive biological fluid flow from the inflow port, wherein said at least one column comprises decellularized, de-vitalized extracellular matrix, and further wherein said at least one column comprises a living cellular component selected from the group consisting of hepatocytes, hepatobiliary progenitor cells, hepatobiliary stem cells, pancreatic islet beta cells, pancreatic stem cells, and combinations thereof; wherein said column has sensors wherein said column can be monitored for metabolic and functional activity; wherein when there are more than one column, the columns are independent from each other; a holding device encasing the at least one column, and wherein the at least one column is attached to the distribution cap with a column connector; a sealingly closeable outer casing; a thermo-pouch encasing the bio-artificial organ device wherein the device may be maintained at an optimal temperature for the cells within the device; the function of the bio-artificial organ may be controlled by control units selected from the group consisting of dedicated sensors, micro-controllers, wireless communication systems, micro-actuators, contactless identification tags, and combinations thereof; an outflow port for egress of a biological fluid, wherein said biological fluid flows through said bio-artificial organ, said biological fluid is processed. Aspects of the present disclosure provide a bio-artificial organ device wherein said bio-artificial organ is external to a patient. Aspects of the present disclosure provide a bio-artificial organ device wherein said bio-artificial organ is implanted in a patient. Aspects of the present disclosure provide a bio-artificial organ device wherein said living cellular compound is selected from the group consisting of human, porcine, or other mammals, and combinations thereof. Aspects of the present disclosure provide a bioartificial organ device wherein said extracellular matrix is derived from a source selected from the group consisting of neonatal porcine or human liver, adult porcine or human liver, neonate porcine or human pancreas, adult porcine or human pancreas, and combinations thereof. Aspects of the present disclosure provide a bio-artificial organ device wherein the living cellular component is derived from a source selected from the group consisting of fetal human liver, neonatal human liver, fetal pediatric human liver, teenage human liver, adult human liver, fetal human pancreas, neonatal human pancreas, pediatric human pancreas, teenage human pancreas, adult human pancreas, cultured human hepatocytes, cultured human beta cells, stem cells derived hepatocytes, stem cells derived beta cells, human pancreatic stem cells, adult or pediatric human hepatobiliary stem cells, adult or pediatric human hepatobiliary progenitor cells and combinations thereof; or from the group consisting of fetal porcine liver, neonatal porcine liver, fetal pediatric porcine liver, teenage porcine liver, adult porcine liver, fetal porcine pancreas, neonatal porcine pancreas, pediatric porcine pancreas, teenage porcine pancreas, adult porcine pancreas, cultured porcine hepatocytes, cultured porcine beta cells, stem cells derived hepatocytes, stem cells derived beta cells, porcine pancreatic stem cells, adult or pediatric porcine hepatobiliary stem cells, adult or pediatric porcine hepatobiliary progenitor cells and combinations thereof. Aspects of the present disclosure provide a bio-artificial organ device wherein the sensors are capable of wireless communication. Aspects of the present disclosure provide a bio-artificial organ device wherein the biological fluid is blood or plasma. Aspects of the present disclosure provide a bio-artificial organ device wherein the inflow port and outflow ports are attached to a central blood line to recirculate blood to the subject. Aspects of the present disclosure provide a bio-artificial organ device wherein the bio-artificial organ contains units selected from the group consisting of an independent redundant battery power system, a hydraulic system, a thermal control system, and combinations thereof. Aspects of the present disclosure provide a bio-artificial organ device wherein the thermal system keeps the bio-artificial organ at a constant temperature. Aspects of the present disclosure provide a bio-artificial organ device wherein sensors can be used to monitor blood values before and after the columns selected from the group consisting of including but not limited to glucose levels, electrolytes, sodium, potassium, chloride, bicarbonate, pH, oxygenation level, ammonia level, lipid levels, the speed and cumulative volume of flow of the blood, temperature, blood pressure, and combinations thereof. Aspects of the present disclosure provide a bio-artificial organ device wherein sensors can be used to monitor blood values selected from the group consisting of hematocrit, iron saturation concentration, red blood cell balance, and combinations thereof. Aspects of the present disclosure provide a bio-artificial organ device wherein said BAO is attached to a patient, and wherein sensors can alert clinical staff overseeing the use of the devices for deviations from normal that may require adjustment of the device or additional diagnostics or therapeutic adjustments for the patient. Aspects of the present disclosure provide a bio-artificial organ device wherein sensors can detect identified toxins selected from the group consisting of prescription medications, over the counter medications, herbal remedies, dietary supplements, ingested, topical toxins, environmental toxins, bio-threats, chemical weapon threats, and combinations thereof. Aspects of the present disclosure provide a bio-artificial organ device wherein sensors can detect infectious agents selected from the group consisting of bacterial, viral, fungal, parasitic, and combinations thereof. Aspects of the present disclosure provide a bio-artificial organ device wherein sensors can detect molecular or cellular breakdown products of infectious agents selected from the group consisting of endotoxins, organism membrane fragments, membrane associated vesicles, and combinations thereof. Aspects of the present disclosure provide a bio-artificial organ device wherein the micro-controller may supervise all the functionality, communicate the status and results of sensor measurements selected from the group consisting of with a cloud based health monitoring system through a wireless connection, receive new/adjusted functional parameters to better adapt to the ongoing treatment.

Aspects of the present disclosure provide a bio-artificial organ device wherein the communication may be encrypted and data available only to the entitled entities. Aspects of the present disclosure provide a bio-artificial organ device wherein the system includes an interface selected from the group consisting of a local user interface, a remote user interface, combinations thereof and wherein the interface is accessible through the wireless connection. Aspects of the present disclosure provide a bio-artificial organ device wherein the micro-actuators together with the hydraulic system insure the control of the blood flow. Aspects of the present disclosure provide a bio-artificial organ device wherein the micro-actuators together with the hydraulic system enable a column exchange without blood loss. Aspects of the present disclosure provide a bio-artificial organ device wherein the micro-actuators together with the hydraulic system are used for precisely flushing the column with isotonic solution before a column exchange in order to minimize the blood loss. Aspects of the present disclosure provide a bio-artificial organ device wherein the bio-artificial organ device will need to hold approximately 500-700 grams of cellularized tissue in order to provide sufficient tissue to function to keep the body in homeostasis. Aspects of the present disclosure provide a bio-artificial organ device wherein the device has a central blood line out and a central blood line in. Aspects of the present disclosure provide a bio-artificial organ device wherein blood flow can be arterial derived, venous derived, and combinations thereof. Aspects of the present disclosure provide a bio-artificial organ device wherein blood flow can come from an implanted or surgically created fistula. Aspects of the present disclosure provide a bio-artificial organ device wherein venous blood flow will be propelled by gravitational force and low pressure of the venous system. Aspects of the present disclosure provide a bio-artificial organ device wherein arterial blood flow will be propelled through arterial blood pressure with or without gravitational force.

Aspects of the present disclosure provide a method of screening for an active compound comprising: providing a bio-artificial organ; providing a potential active compound; applying the potential active compound to the bio-artificial organ; providing a control composition without the potential active compound; measuring the effect of the potential active compound on a parameter of the bio-artificial organ selected from the group consisting of histological, immune-histological, molecular markers, and combinations thereof, as compared to the effect of the control composition.

Aspects of the present disclosure provide a method of treatment of a patient in liver failure comprising: selecting a patient in need of treatment for liver failure; attaching the bio-artificial organ to the patient, wherein the patient is treated. Aspects of the present disclosure provide a method of treatment of a patient in liver failure to bridge said patient to a whole organ transplant comprising: selecting a patient in liver failure; attaching the bio-artificial organ to the patient, wherein the patient is treated. Aspects of the present disclosure provide a method of treating a patient in liver failure to allow their own liver to recover, comprising selecting a patient in liver failure; attaching the bio-artificial organ to the patient, wherein the patient is treated. Aspects of the present disclosure provide a method of treating a patient with chronic disease; selecting a patient with chronic disease; attaching the bio-artificial organ to the patient, wherein the patient is treated. Aspects of the present disclosure provide a method of treating diabetes comprising: selecting a patient with diabetes; attaching the bio-artificial organ to the patient, wherein the patient is treated. Aspects of the present disclosure provide a method wherein the diabetes is selected form the group consisting of type I diabetes, and type II diabetes.

Aspects of the present disclosure provide a bioreactor device comprising: an inflow port for ingress of a biological fluid; a distribution chamber which optionally includes a pump; at least one column in fluid communication with the distribution chamber wherein said at least one column can receive biological fluid flow from the inflow port, wherein said at least one column comprises decellularized, de-vitalized extracellular matrix, and further wherein said at least one column comprises a living cellular component selected from the group consisting of hepatocytes, hepatobiliary progenitor cells, hepatobiliary stem cells, pancreatic islet beta cells, pancreatic stem cells, and combinations thereof; wherein said column has sensors wherein said column can be monitored for metabolic and functional activity; wherein when there are more than one column, the columns are independent from each other; a holding device encasing the at least one column, and wherein the at least one column is attached to the distribution cap with a column connector; a sealingly closeable outer casing; a thermo-pouch encasing the bioreactor device wherein the device may be maintained at an optimal temperature for the cells within the device; the function of the bioreactor may be controlled by control units selected from the group consisting of dedicated sensors, micro-controllers, wireless communication systems, micro-actuators, contactless identification tags, and combinations thereof; an outflow port for egress of a biological fluid, wherein the bioreactor is used to maintain and expand the living cellular component. Aspects of the present disclosure provide a bioreactor wherein said living cellular compound is selected from the group consisting of human, porcine, or other mammals, and combinations thereof. Aspects of the present disclosure provide a bioreactor wherein said extracellular matrix is derived from a source selected from the group consisting of neonatal porcine or human liver, adult porcine or human liver, neonate porcine or human pancreas, adult porcine or human pancreas, and combinations thereof.

Aspects of the present disclosure provide a bioreactor wherein the living cellular component is derived from a source selected from the group consisting of fetal human liver, neonatal human liver, fetal pediatric human liver, teenage human liver, adult human liver, fetal human pancreas, neonatal human pancreas, pediatric human pancreas, teenage human pancreas, adult human pancreas, cultured human hepatocytes, cultured human beta cells, stem cells derived hepatocytes, stem cells derived beta cells, human pancreatic stem cells, adult or pediatric human hepatobiliary stem cells, adult or pediatric human hepatobiliary progenitor cells and combinations thereof or from the group consisting of fetal porcine liver, neonatal porcine liver, fetal pediatric porcine liver, teenage porcine liver, adult porcine liver, fetal porcine pancreas, neonatal porcine pancreas, pediatric porcine pancreas, teenage porcine pancreas, adult porcine pancreas, cultured porcine hepatocytes, cultured porcine beta cells, stem cells derived hepatocytes, stem cells derived beta cells, porcine pancreatic stem cells, adult or pediatric porcine hepatobiliary stem cells, adult or pediatric porcine hepatobiliary progenitor cells and combinations thereof. Aspects of the present disclosure provide a bioreactor wherein the biological fluid is cell culture media. Aspects of the present disclosure provide a bioreactor wherein the sensors are capable of wireless communication. Aspects of the present disclosure provide a bioreactor wherein the bioreactor contains units selected from the group consisting of an independent redundant battery power system, a hydraulic system, a thermal control system, and combinations thereof. Aspects of the present disclosure provide a bioreactor wherein the thermal system keeps the bioreactor at a constant temperature. Aspects of the present disclosure provide a bioreactor wherein sensors can be used to monitor values before and after the columns selected from the group consisting of including but not limited to glucose levels, electrolytes, sodium, potassium, chloride, bicarbonate, pH, oxygenation level, ammonia level, lipid levels, the speed and cumulative volume of flow of the blood, temperature, blood pressure, and combinations thereof.

Aspects of the present disclosure provide a bioreactor wherein sensors can be used to monitor values selected from the group consisting of hematocrit, iron saturation concentration, red blood cell balance, and combinations thereof. Aspects of the present disclosure provide a method to maintain and expand porcine, human, or other mammalian hepatocytes comprising: providing the bioreactor wherein the living cellular component comprises porcine, human, or other mammalian hepatocytes; providing a biological fluid which is a cell culture media, expanding said porcine, human, or other mammalian hepatocytes. Aspects of the present disclosure provide a method of screening for an active compound comprising: providing the expanded porcine, human, or other mammalian hepatocytes; providing a potential active compound; applying the potential active compound to the expanded porcine, human, or other mammalian hepatocytes; providing a control composition without the potential active compound; measuring the effect of the potential active compound on the expanded porcine, human, or other mammalian hepatocytes. Aspects of the present disclosure provide a method to provide large quantities of donor or recipient derived hepatocytes for therapeutic cell transplantation comprising: providing the bioreactor wherein the living cellular component comprises donor or recipient derived hepatocytes; providing a biological fluid which is a cell culture media, expanding said donor or recipient derived hepatocytes; Providing said donor or recipient derived hepatocytes to a patient. Aspects of the present disclosure provide a method further comprising providing the expanded donor or recipient derived hepatocytes to a patient wherein said patient is in need of treatment for infectious, toxic, or acquired or hereditary metabolic diseases, each of which may occur in acute phase, chronic phase, or acute-on-chronic phase. Aspects of the present disclosure provide a method to maintain and expand hepatocytes derived from patients with hereditary liver disease comprising: providing the bioreactor wherein the living cellular component comprises hepatocytes derived from patients with hereditary liver disease; providing a biological fluid which is a cell culture media, expanding said hepatocytes derived from patients with hereditary liver disease. Aspects of the present disclosure provide a method further comprising studying the pathobiology of the hereditary liver disease or treatment effects on such disease.

Aspects of the present disclosure provide a method to maintain and expand hepatocytes derived from patients with infectious liver disease comprising: providing the bioreactor wherein the living cellular component comprises hepatocytes derived from patients with infectious liver disease; providing a biological fluid which is a cell culture media, expanding said hepatocytes derived from patients with infectious liver disease. Aspects of the present disclosure provide a method further comprising studying the pathobiology of the infectious liver disease or treatment effects on such disease. Aspects of the present disclosure provide a method for facilitating the diagnosis of pancreatic cancer in a patient consisting of: obtaining a biological sample from the patient; and detecting the presence or absence of IHoP in the biological sample, wherein the presence of IHoP is indicative of pancreatic cancer. Aspects of the present disclosure provide a method wherein the presence or absence of IHoP is detected using an antibody-based binding moiety which specifically binds to an IHoP protein. Aspects of the present disclosure provide a method wherein said sample is blood, urine, saliva, or a specific tissue biopsy. Aspects of the present disclosure provide a method wherein the antibody-based binding moiety is labeled with a detectable label. Aspects of the present disclosure provide a method wherein the label is selected from the group consisting of a radioactive label, a hapten label, a fluorescent label, and an enzymatic label. Aspects of the present disclosure provide a method wherein the antibody-based binding moiety is an antibody. Aspects of the present disclosure provide a method wherein the antibody is a monoclonal antibody.

Aspects of the present disclosure provide a method for diagnosing pancreatic cancer in a patient consisting of: (a) measuring the levels of IHoP present in a biological sample obtained from the patient, and a test sample; (b) comparing the level of IHoP in the test sample with the level of IHoP present in a control sample; wherein a higher level IHoP in the test sample as compared to the level of IHoP in the control sample is indicative of pancreatic cancer. Aspects of the present disclosure provide a method wherein said sample is blood, urine, saliva, or a specific tissue biopsy. Aspects of the present disclosure provide a method wherein the antibody-based binding moiety is labeled with a detectable label. Aspects of the present disclosure provide a method wherein the label is selected from the group consisting of a radioactive label, a hapten label, a fluorescent label, and an enzymatic label. Aspects of the present disclosure provide a method wherein the antibody-based binding moiety is an antibody. Aspects of the present disclosure provide a method wherein the antibody is a monoclonal antibody. Aspects of the present disclosure provide a method for diagnosing invasive pancreatic cancer in a patient consisting of: a. measuring the levels of IHoP present in a biological sample obtained from the patient, a test sample; b. comparing the level of IHoP in the test sample with the level of IHoP present in a non-invasive control sample; wherein a higher level IHoP in the test sample as compared to the level of IHoP in the non-invasive control sample is indicative of invasive pancreatic cancer. Aspects of the present disclosure provide a method wherein the presence or absence of IHoP is detected using an antibody-based binding moiety which specifically binds to an IHoP protein. Aspects of the present disclosure provide a method wherein the level of IHoP is measured by measuring the protein level of IHoP protein. Aspects of the present disclosure provide a method wherein said sample is blood, urine, saliva, or a specific tissue biopsy.

Aspects of the present disclosure provide a method wherein the protein level of IHoP is measured by a method comprising the steps of: a. contacting the test sample, or preparation thereof, with an antibody-based binding moiety which specifically binds IHoP to form an antibody IHoP complex; and b. detecting the presence of the complex, thereby measuring the level of IHoP present. Aspects of the present disclosure provide a method wherein the antibody-based binding moiety is labeled with a detectable label. Aspects of the present disclosure provide a method wherein the label is selected from the group consisting of a radioactive label, a hapten label, a fluorescent label, and an enzymatic label. Aspects of the present disclosure provide a method wherein the antibody-based binding moiety is an antibody. Aspects of the present disclosure provide a method wherein the antibody is a monoclonal antibody.

Aspects of the present disclosure provide a method for assessment of pancreatic cancer, the method consisting of: a. assaying for IHoP in a biological sample obtained from a subject; and b. determining whether IHoP is present at a level higher than a predetermined level, thereby indicating whether the subject is at an increased risk of pancreatic cancer progression. Aspects of the present disclosure provide a method wherein the predetermined level is based on the level of IHoP normally found in biological samples of healthy subjects. Aspects of the present disclosure provide a method wherein the predetermined level is based on a prior measurement of the subject's IHoP level. Aspects of the present disclosure provide a method wherein the predetermined level is based on the subject's IHoP level prior to treatment. Aspects of the present disclosure provide a method wherein the subject's IHoP level is monitored over time. Aspects of the present disclosure provide a method wherein the cancer progression is a recurrence of cancer. Aspects of the present disclosure provide a method wherein the cancer progression is an increase of metastatic activity. Aspects of the present disclosure provide a method wherein the cancer progression is a progression in cancer grade or stage. Aspects of the present disclosure provide a method wherein the IHoP protein is assayed for by an immunoassay or by mass spectrometry.

Aspects of the present disclosure provide a method of monitoring the efficacy of a therapeutic treatment of pancreatic cancer, the method comprising: (i) providing a biological sample from a patient undergoing the therapeutic treatment; and (ii) determining the level of IHoP in the biological sample by contacting the biological sample with an antibody-based binding moiety which specifically binds to an IHoP protein, thereby monitoring the efficacy of the therapy. Aspects of the present disclosure provide a method wherein the antibody-based binding moiety is labeled with a detectable label. Aspects of the present disclosure provide a method wherein the label is selected from the group consisting of a radioactive label, a hapten label, a fluorescent label, and an enzymatic label. Aspects of the present disclosure provide a method wherein the antibody-based binding moiety is an antibody. Aspects of the present disclosure provide a method wherein the antibody is a monoclonal antibody.

BRIEF DESCRIPTION OF SEVERAL VIEWS OF THE DRAWINGS

The invention will be described in conjunction with the following drawings in which like reference numerals designate like elements and wherein:

FIG. 9 relates to the nucleic acid sequence encoding IHoP (SEQ ID NO: 1).

FIG. 10 relates to the amino acid sequence of IHop (SEQ ID NO: 2).

DETAILED DESCRIPTION OF PREFERRED EMBODIMENTS OF THE INVENTION

Figure 1:
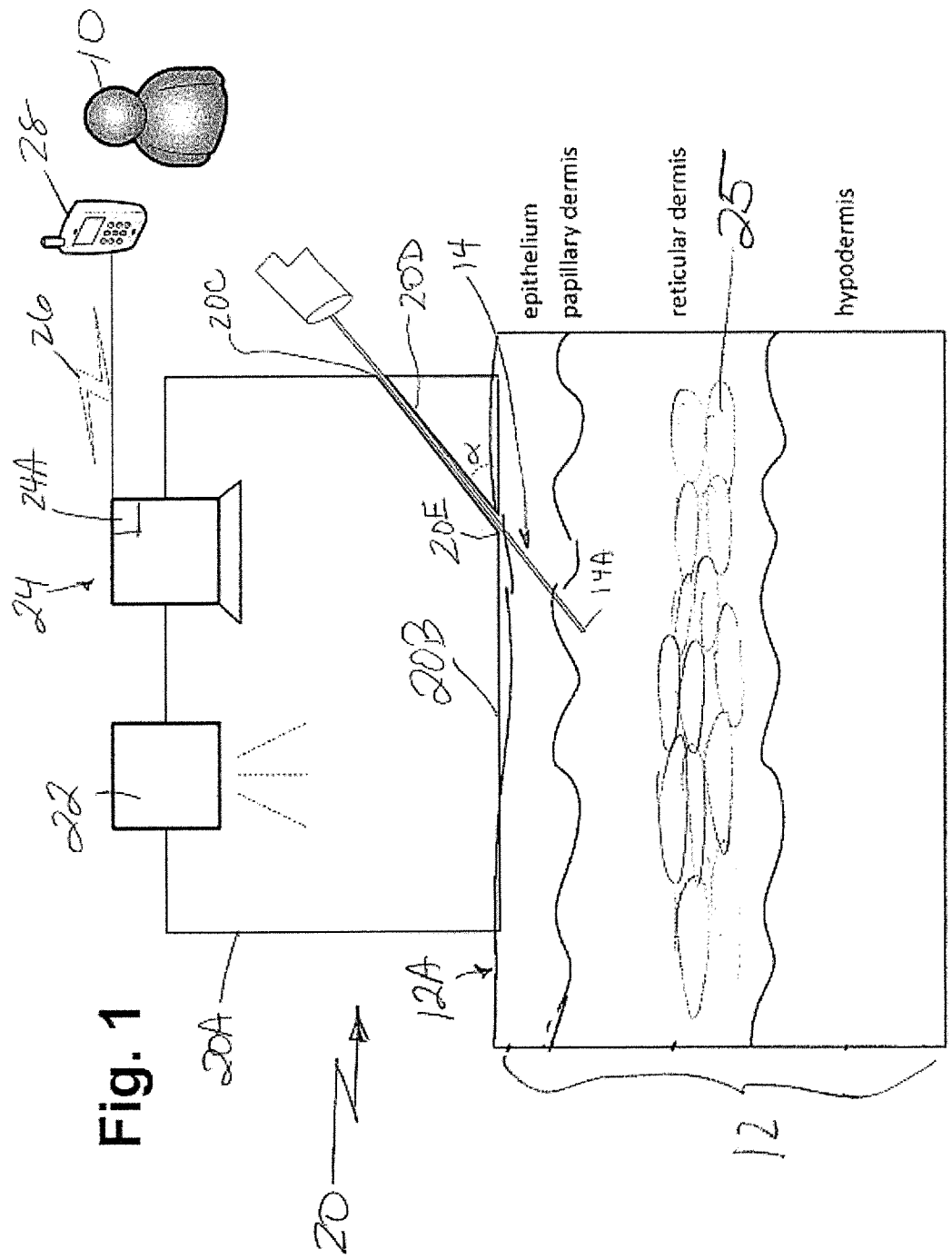
FIG. 1 depicts a diagrammatic view of a first embodiment of a device for guiding an implanting of a sensor within the skin of a subject and using a wireless connection between the confocal lens/camera and a user display.

As used herein, the term "dermal interstitial sinus" refers to the middle to lower region of the dermis, i.e., the reticular dermis which communicates directly with the systemic lymphatic circulation and, from there, into the vascular system, from which, in a closed circuit derives the interstitial sinus derives its fluid.

As used herein, "intradermal" refers to administration of a biologically active agent into the dermis in such a manner that the agent readily reaches the dermal interstitial sinus. Such can result from placement of the agent in the middle to lower region of the dermis, i.e., the reticular dermis. In certain embodiments, the invention provides for the controlled delivery of a biologically active agent in this dermal compartment below the papillary dermis in the newly discovered interstitial sinus of the reticular dermis which communicates directly with the systemic lymphatic circulation and, from there, into the vascular system. In certain embodiments, the invention provides for sampling of the fluid in the interstitial sinus of the reticular dermis which communicates directly with the systemic lymphatic circulation and, from there, into the vascular system, and can therefore serve as a medium to test for biological, chemical, and/or pharmacological markers from the subject.

The term "administration" of the pharmaceutically active compounds and the pharmaceutical compositions defined herein. "Ameliorate" or "amelioration" means a lessening of the detrimental effect or severity of the disease in the subject receiving therapy, the severity of the response being determined by means that are well known in the art.

As used herein, the term "effective amount" refers to the amount of a therapy that is sufficient to result in the prevention of the development, recurrence, or onset of a disease or condition, such as neoplasia or infection, and one or more symptoms thereof, to enhance or improve the prophylactic effect(s) of another therapy, reduce the severity, the duration of a disease or condition, ameliorate one or more symptoms of a disease or condition prevent the advancement of a disease or condition, cause regression of a disease or condition, and/or enhance or improve the therapeutic effect(s) of another therapy. An amount is "effective" as used herein, when the amount provides an effect in the subject. As used herein, the term "effective amount" means an amount of a compound or composition sufficient to significantly induce a positive benefit, including independently or in combinations the benefits disclosed herein, but low enough to avoid serious side effects, i.e., to provide a reasonable benefit to risk ratio, within the scope of sound judgment of the skilled artisan. For those skilled in the art, the effective amount, as well as dosage and frequency of administration, may easily be determined according to their knowledge and standard methodology of merely routine experimentation based on the present disclosure.

By "compatible" herein is meant that the components of the compositions which comprise the present invention are capable of being commingled without interacting in a manner which would substantially decrease the efficacy of the pharmaceutically active compound under ordinary use conditions.

By "pharmaceutically acceptable" or "pharmacologically acceptable" is meant a material which is not biologically or otherwise undesirable, i.e., the material may be administered to an individual without causing undesirable biological effects or interacting in a deleterious manner with any of the components of the composition in which it is contained.

As used herein, a "pharmaceutically acceptable carrier" is a material that is relatively nontoxic and generally inert and does not affect the functionality of the active ingredients adversely. Examples of pharmaceutically acceptable carriers are well known and they are sometimes referred to as diluents, vehicles or excipients. The carriers may be organic or inorganic in nature. In addition, the formulation may contain additives such as flavoring agents, coloring agents, thickening or gelling agents, emulsifiers, wetting agents, buffers, stabilizers, and preservatives such as antioxidants.

As used herein, the terms "prevent," "preventing" and "prevention" in the context of the administration of a therapy to a subject refer to the prevention or inhibition of the recurrence, onset, and/or development of a disease or condition, or a symptom thereof in a subject resulting from the administration of a therapy (e.g., a prophylactic or therapeutic agent), or a combination of therapies (e.g., a combination of prophylactic or therapeutic agents).

The term "pharmaceutical composition" as used herein means a composition that is made under conditions such that it is suitable for administration to, for example, humans, e.g., it is made under GMP conditions and contains pharmaceutically acceptable excipients, e.g., without limitation, stabilizers, pH adjusting agents, bulking agents, buffers, carriers, diluents, vehicles, solubilizers, and binders.

As used herein, the term "subject" encompasses mammals and non-mammals. Examples of mammals include but are not limited to any member of the Mammalia class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include but are not limited to birds, fish and the like. The term does not denote a particular age or sex.

As used herein, the terms "treating" or "treatment" of a disease include preventing the disease, i.e. preventing clinical symptoms of the disease in a subject that may be exposed to, or predisposed to, the disease, but does not yet experience or display symptoms of the disease; inhibiting the disease, i.e., arresting the development of the disease or its clinical symptoms, such as by suppressing or relieving the disease, i.e., causing regression of the disease or its clinical symptoms.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent depending on the context in which it is used. If there are uses of the term which are not clear to persons of ordinary skill in the art given the context in which it is used, "about" will mean up to plus or minus 10% of the particular term.

As used herein, "targeted sampling" means the use of intradermal sampling from particular specific tissues and/or organs and/or a biological entity not otherwise accessed or understood to be accessed by the conventional sampling methods.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The term "analyte" as used herein is a broad term, and is to be given its ordinary and customary meaning to a person of ordinary skill in the art (and is not to be limited to a special or customized meaning), and refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-.beta. hydroxycholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free .beta.-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, .beta.); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidum, Trypanosoma cruzi/rangeli*, vesicular *stomatis* virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), histamine, Advanced Glycation End Products (AGEs) and 5-hydroxyindoleacetic acid (FHIAA).

The terms "sensor" and "sensor system" as used herein are broad terms, and are to be given their ordinary and customary meaning to a person of ordinary skill in the art (and are not to be limited to a special or customized meaning), and refer without limitation to a device, component, or region of a device by which an analyte can be quantified.

The term "sensing region" as used herein is a broad term, and is to be given its ordinary and customary meaning to a person of ordinary skill in the art (and is not to be limited to a special or customized meaning), and refers without limitation to the region of a monitoring device responsible for the detection of a particular analyte. The sensing region generally comprises a non-conductive body, a working electrode (anode), and can include a reference electrode (optional), and/or a counter electrode (cathode) forming electrochemically reactive surfaces on the body.

The terms "continuous" and "continuously" as used herein are broad terms, and are to be given their ordinary and customary meanings to a person of ordinary skill in the art (and are not to be limited to a special or customized meaning), and refer without limitation to the condition of being marked by substantially uninterrupted extension in space, time or sequence. In one embodiment, an analyte concentration is measured continuously or continually, for example at time intervals ranging from fractions of a second up to, for example, 1, 2, or 5 minutes, or longer. It should be understood that continuous glucose sensors generally continually measure glucose concentration without required user initiation and/or interaction for each measurement. These terms include situations wherein data gaps can exist (e.g., when a continuous glucose sensor is temporarily not providing data).

Skin

The skin comprises two layers, the outer or upper surface called the epidermis, and the internal surface referred to as the dermis. The epidermis does not contain any blood vessels and it is dependent on the underlying dermis for nutrient delivery and waste disposal via diffusion. The inner layer, the dermis, is composed of two layers, the more superficial papillary dermis and the deeper reticular dermis. The papillary dermis is thinner and consists primarily of loose connective tissue containing small capillaries, elastic fibers, reticular fibers and some collagen. The deeper reticular dermis consists of a thicker connective tissue containing larger blood vessels, interlaced elastic fibers and core spindles of collagen fibers arranged in layers parallel to the surface. The reticular layer also contains many antigen-presenting cells, fibroblasts, mast cells, nerve endings, and lymphatics. Because of the high amount of blood vessels, lymphatics, and antigen presenting cells in the dermis, this is an ideal site as a medium to test for biological, chemical, and/or pharmacological markers from the subject.

Intradermal Sampling

As used herein, sampling from the intradermal compartment is intended to mean sampling of the dermis in such a manner that the sample is a fluid from the richly vascularized reticular dermis and and/or lymphatic vessels. Such can result from placement of the applicator and/or sensor and/or cannula and/or needle in the reticular region of the dermis, i.e., the upper portion of the reticular dermis. In exemplary embodiments, the applicator is a cannula. The controlled sampling in this dermal compartment below the papillary dermis in the reticular dermis, but sufficiently above the interface between the dermis and the subcutaneous tissue, should enable an efficient (outward) migration of the lymphatic fluid from the lymphatic microcapillary bed (in the papillary dermis), where it can be sampled. In some embodiments, placement of a trocar predominately at a depth of at least about 0.3 mm, more preferably, at least about 0.4 mm and most preferably at least about 0.5 mm up to a depth of no more than about 2.5 mm, more preferably, no more than about 2.0 mm and most preferably no more than about 1.7 mm will result in efficient sampling of the lymphatic fluid.

In accordance with the invention micro needle-based systems or any other means known to one skilled in the art to sample the intradermal compartment. Micro-cannula- and microneedle-based methodology and devices may also be used. Standard steel cannula can also be used for intradermal sampling. These methods and devices include the sampling through narrow gauge (30G or narrower) "micro-cannula" with a limited depth of penetration (typically ranging from 10 microm to 2 mm), as defined by the total length of the cannula or the total length of the cannula that is exposed beyond a depth-limiting hub feature.

The intradermal sampling in accordance with the present invention are particularly beneficial in the diagnosis of the diseases including chronic and acute diseases which include but are not limited to lymphoma, melanoma, leukemia, breast cancer, colorectal cancer, cancer metastasis, diseases of the lymphatic system, any disease affecting the lymph-nodes, e.g., axillary, politeal, lingual, viral diseases, e.g., HIV, immune disorders such as rejection, metabolic disorders, diabetes, and infectious diseases. The present invention is useful for diagnostic procedures including, but not limited to, surgical methods, biopsies, non-invasive screening and image-guided biopsies.

Imaging Agents

The present invention encompasses delivering imaging agents suitable for imaging by one or more imaging techniques, for example to identify the target area of the skin. Any imaging agent known in the art is contemplated within the methods and compositions of the invention. In some embodiments, the contrast agents are in particulate form and are adapted to be preferentially taken up by the lymphatic system upon administration. These contrast agents can be radiopaque materials, MRI imaging agents, ultrasound imaging agents, and any other contrast agent suitable for a device that images an animal body. Contrast agents for use in the methods of the invention are preferably nontoxic and/or non-radioactive. There are two major classes of contrast agents: paramagnetic and superparamagnetic; each of which is contemplated within the methods of the invention. Paramagnetic agents have unpaired electron spins that facilitate relaxation of nuclei, usually water protons, that can closely approach them (within 1 nm). These agents decrease both T1 and T2, are effective in uM concentrations, and can be incorporated in chelates with favorable biodistribution and toxicity profiles. Schering's patented product, GdDTPA (gadolinium diethylenetriaminepentaacetic acid), is an outstanding example of several commercially available such agents. In some embodiments the contrast agents are incorporated into macromolecules to avoid uptake by the systemic circulation. Combination with albumin, other biological molecules of appropriate size, latex, dextran, polystyrene or other nontoxic natural or synthetic polymer, or encapsulation in liposomes, can be accomplished using methods known to those skilled in the art.

The invention further encompasses non-specific contrast agents including but not limited to: MRI contrast agents (e.g., gadolinium, paramagnetic particles, super-paramagnetic particles), ultrasound contrast agents (e.g., microbubbles), CT contrast agents (e.g., radiolabels), X-Ray contrast agents (e.g., Iodine), PET contrast agents (e.g., any 2 photon emitter, F19, Fluoro-deoxy-glucose), Photoacoustic contrast agents (e.g., dyes, various light absorbing molecules), Optical contrast agents (e.g., Fluorescent: CY5, squaraines, near infrared dyes, i.e. indocyanine green, lanthanide fluors (e.g., Europium, Turbium).

In a particular example, microbubble ultrasound contrast agent is delivered as described herein. An ultrasound probe is positioned either at the injection site or at a regional lymph node site. Although not intending to be bound by a particular mechanism of action the contrast agent is delivered to the intradermal compartments and immediately travels through the lymphatic vessels and to the lymph node. The ultrasound probe detects the contrast agent as it passes beneath the probe. Both diagnostic flow rate and architecture information, including obstructions, can be obtained. In this embodiment, the images can be obtained continuously (real time) or in an episodic manner.

In some embodiments, magnetic resonance images further comprise an additional step of making sure to pre-image the subject prior to injection of the agent, e.g., contrast agent. In some embodiments, Multiple images post injection are obtained over time and compared to the pre-image. The invention encompasses methods for detection and location of lymph nodes, as well as information concerning other tissues, organs and biological entities using methods disclosed herein and known to those skilled in the art, e.g., CT, PET, SPECT, Optical (e.g., Fluorescent, Chemiluminescent), Confocal, and X-Ray imaging.

Presence of the imaging agent can be detected in the subject using methods known in the art for in vivo scanning. These methods depend upon the type of label used. Skilled artisans will be able to determine the appropriate method for detecting a particular label. Methods and devices that may be used in the diagnostic methods of the invention include but are not limited to computed tomography (CT), whole body scan such as position emission tomography (PET), magnetic resonance imaging (MRI), single photon emission computer tomography (SPECT), X-Ray, Optical (spectrophotometric) imaging, confocal imaging, and sonography.

Confocal Laser Scanning Microscopy

One of the preferred embodiments of detecting the target area of the skin relies on the use of confocal laser scanning microscopy, which in a further preferred embodiment may use UV light sources. Confocal microscopy offers several advantages over conventional optical microscopy, one of the most important being the elimination of out-of-focus information that distorts the image, controllable depth of field and sub-micron resolution. A further advantage of confocal microscopy is that fluorescence of various portions of the specimen that are out-of-focus can be filtered out and so do not interfere with the portions or sections that are in-focus thereby yielding an image that is considerably sharper and shows a better resolution than a comparable image obtained by classical light microscopy.

The basic principle of confocal scanning microscopy is the use of a screen with a pinhole at the focal point of the microscope lens system which is "conjugate" to the point at which the objective lens is focused. Only light coming from the focal point of the objective is focused at the pinhole and can pass through to the detector, which e.g. may be a charge couple device (CCD). Light coming from an out-of-focus section of the sample will be nearly completely filtered out.

Thus, a confocal microscope has a significantly better resolution than a conventional microscope for the x- and y-direction. Furthermore, it has a smaller depth of field in the z-direction. By scanning the focal point through the sample, it is thus possible to view different planes of a sample and to then rebuild a 3-dimensional image of the sample. Furthermore, confocal microscopy is compatible with different wavelengths of light.

If a confocal laser-scanning microscope is integrated in e.g. an endoscopic device, an actuator may be used to scan the confocal microscope over the tissue of interest. A first coarse scan can then be used to determine the morphology of the tissue and the tissue in which an up-regulation of e.g. TERT is seen can be identified from this screen.

For confocal scanning microscope one may use monochromatic or polychromatic light however, monochromatic UV light with a wavelength between 240 nm and 280 nm may be preferred. As a confocal laser scanning microscope one may use a microscope such as LEICA DMLM and having a Qimaging Retiga 2000R FASTCooled Mono 12-bit camera unit (www.qimaging.com) for measuring the signal intensity of the fluorescence signal. A Leica DM6000 may be particularly preferred.

For the purposes of the present invention where the reticular dermis is to be targeted, the confocal laser-scanning microscope may be integrated or relied upon. Systems, which are known for this purpose, differ mostly in the manner in which the image is scanned. Two rather advanced commercial systems are available, e.g. from Optiscan and Mauna Kir Technology. The Mauna Kir instrument is a proximally scanned system where the image is transferred down the endoscope with a coherent fibre optic bundle. A selected point or fibre is imaged into the sampled tissue at the distal end. This confocal endomicroscope may be delivered through the working channel of an endoscope. Since the field of view of the endomicroscope is small, placement of the probe is guided by standard video endoscopy. Hence, the endoscope platform must include both a video imager and the confocal microscope. Of course, the endoscope unit may also comprise or be coupled to computer devices and software packages that allow processing of the obtained images.

Detection units may e.g. be Optronics DEI-700 CE three-chip CCD camera connected via a BQ6000 frame-grabber board to a computer. Alternatively one may use a Hitachi HV-C20 three-chip CCD camera. Software packages for image analysis may e.g. be the Bioquant True Color Windows 98 v3.50.6 image analysis software package (R&M Biometrics, Nashville, Tenn.) or Image-Pro Plus 3.0 image analysis software. Another system that may be used is the BioView Duet system (BioView Ltd, Rehovot, Israel which is based on a dual mode, fully automated microscope (Axioplan 2, Carl Zeiss, Jena, Germany), an XY motorized 8-slides stage (Marzhauscr, Wetzler, Germany) a 3CCD progressive scan color camera (DXC9000, Sony, Tokyo, Japan) and a computer for control and analysis of the system and the data. Optiscan has developed an endomicroscope employing distal scanning.

Microscopy

Microscopy methods that may be used with this invention include but are not limited to bright field, oblique illumination, dark field, dispersion staining, phase contrast, differential interference contrast (DIC), polarized light, epifluorescence, interference reflection, fluorescence, confocal (including CLASS), confocal laser scanning microscopy (CLSM), structured illumination, stimulated emission depletion, electron, scanning probe, infrared, laser, widefield, light field microscopy, lensless on-chip holographic microscopy, digital and conventional holographic microscopy, extended depth-of-field microscopy, optical scatter imaging microscopy, deconvolution microscopy, defocusing microscopy, quantitative phase microscopy, diffraction phase microscopy, confocal Raman microscopy, scanning acoustic microscopy and X-ray microscopy. Magnification levels used by microscopy may include, as non limiting examples, up to 2×, 5×, 10×, 20×, 40×, 60×, 100×, 100×, 1000×, or higher magnifications. Feasible magnification levels will vary with the type of microscopy used.

Fluorescence Microscopy

Fluorescence microscopy generally involves labeling of cells or other samples with fluorescent labels, described in more detail below. Microscopic imaging of fluorescently labeled samples may gather information regarding the presence, amounts, and locations of the target that is labeled at a given moment in time or over a period of time. Fluorescence may also be used to enhance sensitivity for detecting cells, cellular structures, or cellular function. In fluorescence microscopy, a beam of light is used to excite the fluorescent molecules, which then emit light of a different wavelength for detection. Sources of light for exciting fluorophores are well known in the art, including but not limited to xenon lamps, lasers, LEDs, and photodiodes. Detectors include but are not limited to PMTs, CCDs, and cameras.

Fluorimetry refers to measuring the light emitted by a fluorescent molecule coupled to a subject upon exciting the fluorescent molecule with incident light. Fluorimetry may use any of the fluorescent molecules, labels, and targets. In some embodiments, fluorimetry uses substrate molecules that change in fluorescence based on an enzymatic activity, such as converting NAD+ to NADH or vice versa or producing beta-galactosidase from a precursor molecule. Fluorimetry may be used with a polarized excitation source to measure fluorescence polarization or anisotropy of a subject, which may provide information about the size and/or binding state.

Illuminator

An illuminator or light source may be any device capable of emitting energy along the electromagnetic spectrum. A light source may emit light along a visible spectrum. In one example, a light source may be a light-emitting diode (LED) (e.g., gallium arsenide (GaAs) LED, aluminum gallium arsenide (AlGaAs) LED, gallium arsenide phosphide (GaAsP) LED, aluminum gallium indium phosphide (AlGaInP) LED, gallium(III) phosphide (GaP) LED, indium gallium nitride (InGaN)/gallium(III) nitride (GaN) LED, or aluminum gallium phosphide (AlGaP) LED). In another example, a light source can be a laser, for example a vertical cavity surface emitting laser (VCSEL) or other suitable light emitter such as an Indium-Gallium-Aluminum-Phosphide (InGaAlP) laser, a Gallium-Arsenic Phosphide/Gallium Phosphide (GaAsP/GaP) laser, or a Gallium-Aluminum-Arsenide/Gallium-Aluminum-Arsenide (GaAlAs/GaAs) laser. Other examples of light sources may include but are not limited to electron stimulated light sources (e.g., Cathodoluminescence, Electron Stimulated Luminescence (ESL light bulbs), Cathode ray tube (CRT monitor), Nixie tube), incandescent light sources (e.g., Carbon button lamp, Conventional incandescent light bulbs, Halogen lamps, Globar, Nernst lamp), electroluminescent (EL) light sources (e.g., Light-emitting diodes—Organic light-emitting diodes, Polymer light-emitting diodes, Solid-state lighting, LED lamp, Electroluminescent sheets Electroluminescent wires), gas discharge light sources (e.g., Fluorescent lamps, Inductive lighting, Hollow cathode lamp, Neon and argon lamps, Plasma lamps, Xenon flash lamps), or high-intensity discharge light sources (e.g., Carbon arc lamps, Ceramic discharge metal halide lamps, Hydrargyrum medium-arc iodide lamps, Mercury-vapor lamps, Metal halide lamps, Sodium vapor lamps, Xenon arc lamps). Alternatively, a light source may be a bioluminescent, chemiluminescent, phosphorescent, or fluorescent light source.

The light source may be capable of emitting electromagnetic waves in any spectrum. For example, the light source may have a wavelength falling between 10 nm and 100 microm. The wavelength of light may fall between 100 nm to 5000 nm, 300 nm to 1000 nm, or 400 nm to 800 nm. The wavelength of light may be less than, and/or equal to 10 nm, 100 nm, 200 nm, 300 nm, 400 nm, 500 nm, 600 nm, 700 nm, 800 nm, 900 nm, 1000 nm, 1100 nm, 1200 nm, 1300 nm, 1500 nm, 1750 nm, 2000 nm, 2500 nm, 3000 nm, 4000 nm, or 5000 nm.

One or more of a plurality of light sources may be provided. In some embodiments, each of the plurality of light sources may be the same. Alternatively, one or more of the light sources may vary. The light characteristics of the light emitted by the light sources may be the same or may vary. The light sources may be independently controllable.

Camera

The device may be used with any standard compact digital imaging device (e.g., a charge-coupled device (CCD) or complementary metal-oxide-semiconductor (CMOS) sensors) as the image acquisition device. The example device shown in a) has an external electrical power source, the two LED arrays for illuminating the object/surface to be imaged, and a commercially available digital camera securely fixed to lightweight metal frame equipped with a convenient handle for imaging. A multi-band filter is held in front of the digital camera to allow wavelength filtering of the detected optical signal emanating from the object/surface being imaged. The camera's video/USB output cables allow transfer of imaging data to a computer for storage and subsequent analysis. This example uses a commercially-available 8.1-megapixel Sony digital camera (Sony Cybershot DSC-T200 Digital Camera, Sony Corporation, North America). This camera may be suitable because of i) its slim vertical design which may be easily integrated into the enclosure frame, ii) its large 3.5-inch widescreen touch-panel LCD for ease of control, iii) its Carl Zeiss 5.times. optical zoom lens, and iv) its use in low light (e.g., ISO 3200). The device may have a built-in flash which allows for standard white light imaging (e.g., high-definition still or video with sound recording output). Camera interface ports may support both wired (e.g., USB) or wireless (e.g., Bluetooth, WiFi, and similar modalities) data transfer or 3.sup.rd party add-on modules to a variety of external devices, such as: a head-mounted display, an external printer, a tablet computer, laptop computer, personal desktop computer, a wireless device to permit transfer of imaging data to a remote site/other device, a global positioning system (GPS) device, a device allowing the use of extra memory, and a microphone. The digital camera is powered by rechargeable batteries, or AC/DC powered supply. The digital imaging device may include, but is not limited to, digital cameras, webcams, digital SLR cameras, camcorders/video recorders, cellular telephones with embedded digital cameras, Smartphones™, personal digital assistants (PDAs), and laptop computers/tablet PCs, or personal desktop computers, all of which contain/or are connected to a digital imaging detector/sensor.

This light signal produced by the excitation/illumination light sources may be detected by the imaging device using optical filter(s) (e.g., those available from Chroma Technology Corp, Rockingham, VT, USA) that reject the excitation light but allow selected wavelengths of emitted light from the tissue to be detected, thus forming an image on the display. There may for example be an optical filter holder attached to the enclosure frame in from of the digital camera lens which may accommodate one or more optical filters with different discrete spectral bandwidths, such as the device with the LED arrays turned on to emit bright violet/blue light, with a single emission filter in place or the device may use a multiple-optical filter holder used to select the appropriate filter for desired wavelength-specific imaging.

The device may be modified by using optical or variably oriented polarization filters (e.g., linear or circular combined with the use of optical wave plates) attached in a reasonable manner to the excitation/illumination light sources and the imaging detector device. In this way, the device may be used to image the tissue surface with polarized light illumination and non-polarized light detection or vice versa, or polarized light illumination and polarized light detection, with either white light reflectance and/or fluorescence imaging. This may permit imaging with minimized specular reflections (e.g., glare from white light imaging), as well as enable imaging of fluorescence polarization and/or anisotropy-dependent changes in connective tissues (e.g., collagens and elastin) within the target area and surrounding normal tissues.

All components of the imaging device may be integrated into a single structure, such as an ergonomically designed enclosed structure with a handle, allowing it to be comfortably held with one or both hands. The device may also be provided without any handle. The device may be light weight, portable, and may enable real-time digital imaging (e.g., still and/or video) of any target surface (for example, the skin and/or oral cavity, which is also accessible) using white light, fluorescence and/or reflectance imaging modes. The device may be scanned across the body surface for imaging by holding it at variable distances from the surface, and may be used in a lit environment/room to image white light reflectance/fluorescence. The device may be used in a dim or dark environment/room to optimize the tissue fluorescence signals, and minimize background signals from room lights. The device may be used for direct (e.g., with the unaided eye) or indirect (e.g., via the viewing screen of the digital imaging device) visualization of the target area and surrounding tissues.

The device may also be embodied as not being hand-held or portable, for example as being attached to a mounting mechanism (e.g., a tripod or stand) for use as a relatively stationary optical imaging device for white light, fluorescence and reflectance imaging of objects, materials, and surfaces (e.g., a body). This may allow the device to be used on a desk or table or for "assembly line" imaging of objects, materials and surfaces. In some embodiments, the mounting mechanism may be mobile.

Other features of this device may include the capability of digital image and video recording, possibly with audio, methods for documentation (e.g., with image storage and analysis software), and wired or wireless data transmission for remote telemedicine/E-health needs. For example, the device may be a mobile communication device such as a cellular telephone. The telephone may be fitted into the holding frame for convenient imaging. The images from the camera, for example in a cellular telephone or a confocal camera, may be sent wirelessly to another cellular telephone, or wirelessly (e.g., via Bluetooth connectivity) to a personal electronic device or computer for image storage and analysis. This demonstrates the capability of the device to perform real-time hand-held fluorescence imaging and wireless transmission to a remote site/person as part of a telemedicine/E-health care infrastructure.

Analyte Sensor System

As shown in FIG. 1, the device 20 of the present invention comprises a housing 20A that is adapted to be placed against the skin 12A of the patient. An ultraviolet (UV) illuminator 22 is positioned on a top surface of the housing 20A to activate a fluorescent dye 25 that has been previously-injected within the patient and which ultimately is positioned within the reticular dermis of the patient's skin layers 12, in accordance with the preceding and following discussion. The housing 20A also comprises a camera (e.g., a confocal lens device, including focus adjustment) 24 that can image the skin that is beneath the bottom portion 20B of the housing 20A. In addition, the housing 20A comprises a cannula insertion port 20C and channel 20D that is Ruined within the housing 20A at a predetermined angle α, preferably a shallow angle. The distal end of the channel 20D comprises an exit port 20E that is in contact with the skin surface 12D. The confocal lens device 24 may also comprise a transponder 24A for effecting a wireless (e.g., (e.g., Bluetooth, WiFi, IRdA, ZigBee, WiMAX, LTE, etc.) communication 26 to a remote computer display 28 (e.g., a smartphone, imaging display, etc.) to permit a user 10 to see the illuminated fluorescent dye 25 within the reticular dermis; alternatively, as shown in FIG. 2, the confocal lens device 24 may be adaptable to be directly coupled to the computer display 28 without the need for any transponder 24A and wireless communication 26.

Figure 2:
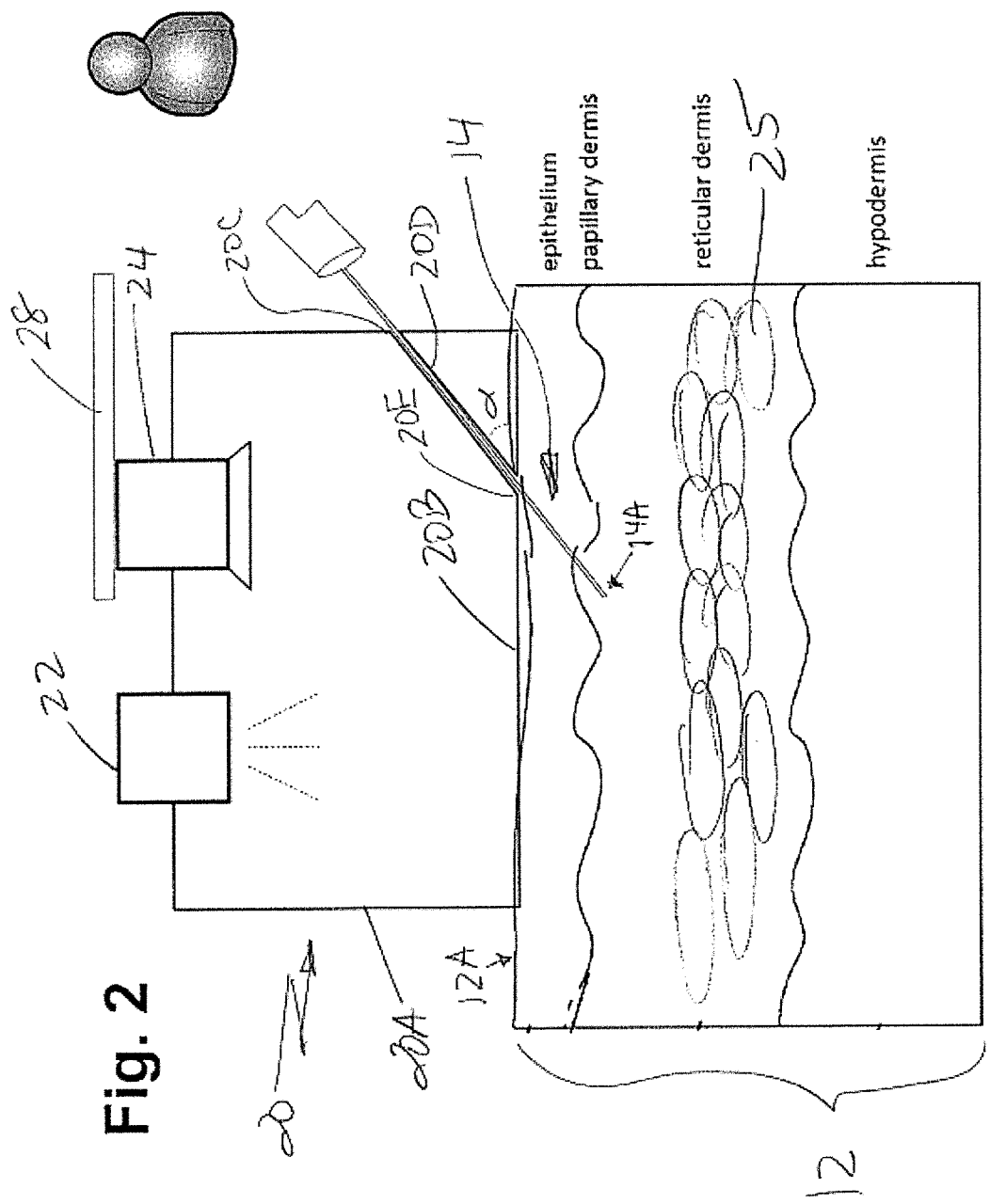
FIG. 2 depicts a diagrammatic view of a second embodiment of a device for guiding an implanting of a sensor within the skin of a subject and using a wired connection between the confocal lens/camera and a user display.
Figure 3:
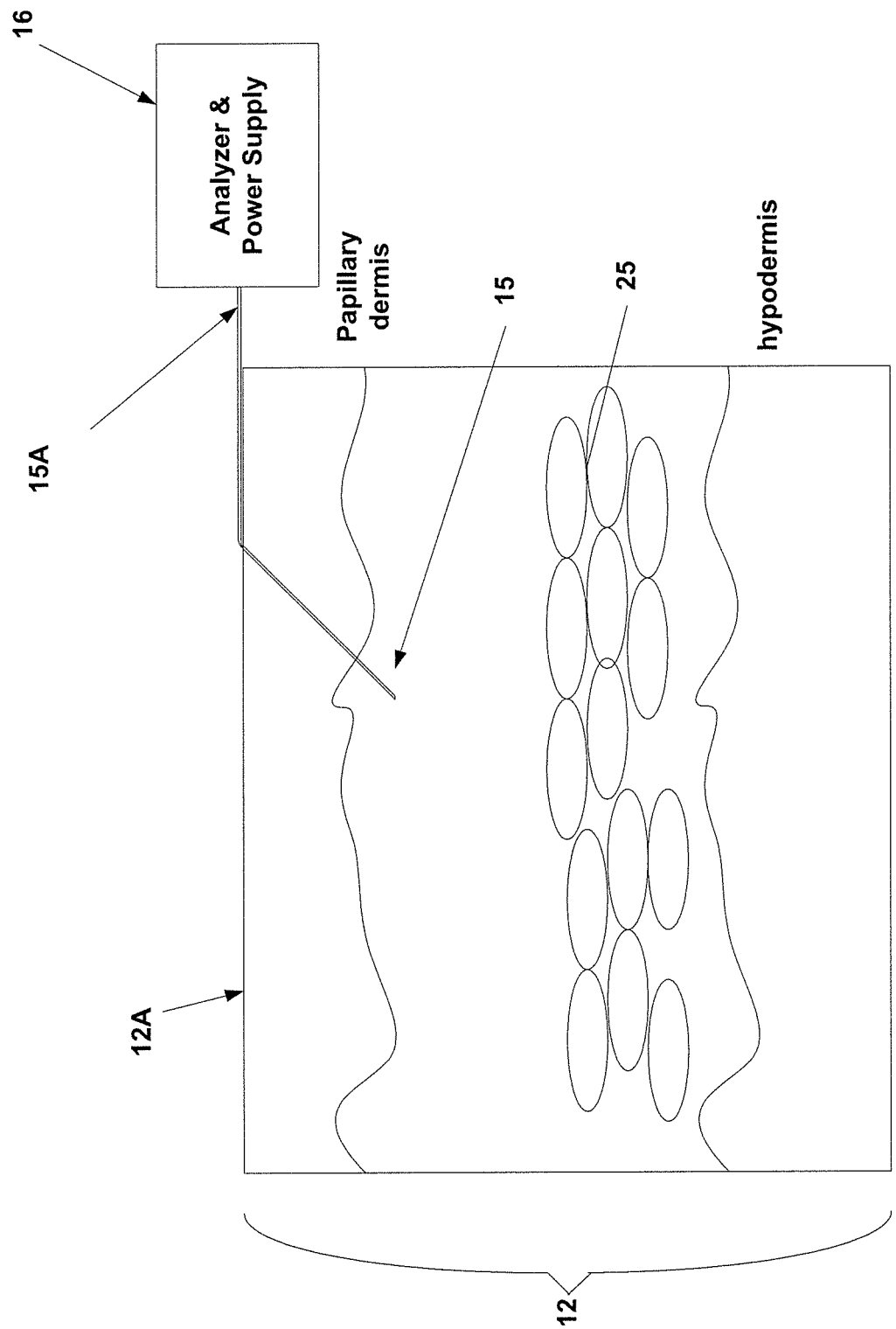
FIG. 3 depicts the condition of the implanted sensor once the first or second embodiment has been removed from the skin.

In operation, as shown in FIG. 1 or 2, the fluorescent dye 25 is injected within the patient and whereby this dye 25 makes its way within the reticular dermis, in accordance with the preceding and following discussion. The user 10 then places the housing 20A on the skin of the patient and activates the UV illuminator 22 and confocal lens device 24. The UV illuminator 22 illuminates the skin layers 12 and the fluorescent dye 25 then fluoresces. The confocal lens device 24 then transmits an image (either via the wireless transponder 24A or via direct coupling) which then appears in the user's computer display 28. While monitoring the display 28, the user 10 then inserts the cannula 14 (e.g., a needle comprising the sensor 15, etc.) into the insertion port 20C and down into the channel 20D, through the skin 12A and immediately stops the insertion as soon as the needle tip 14A appears in the fluorescent dye 25, thereby confirming that the needle tip 14A is properly disposed in the reticular dermis. The appearance of lymph fluid and/or fluorescent dye 25 within the transparent needle 14 provides another indicator that the proper location of the needle tip 14 within the reticular dermis. At that point, as shown in FIG. 3, the needle 14 is withdrawn, leaving the sensor 15 (e.g., a glucose sensor), hereinafter referred to as a "sampler" ideally positioned within the reticular dermis. The housing 20A is then removed from off of the skin 12A. The proximal end 15A of the sensor 15 is then coupled to the requisite analyzer and sensor excitation (if required) as shown by reference number 16.

Figure 4A:
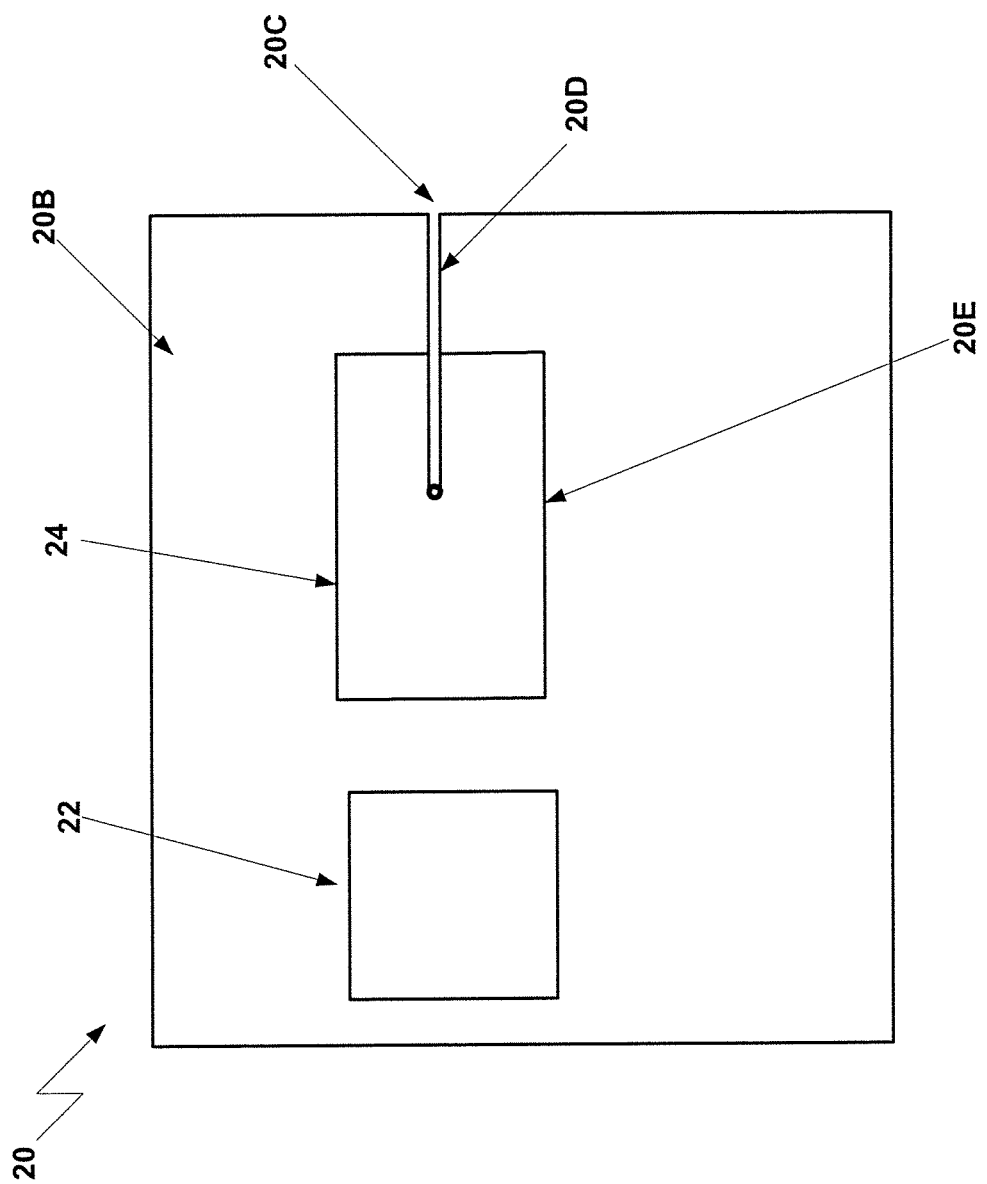
FIG. 4A is a diagrammatic bottom view of the first or second embodiment showing an open bottom.
Figure 4B:
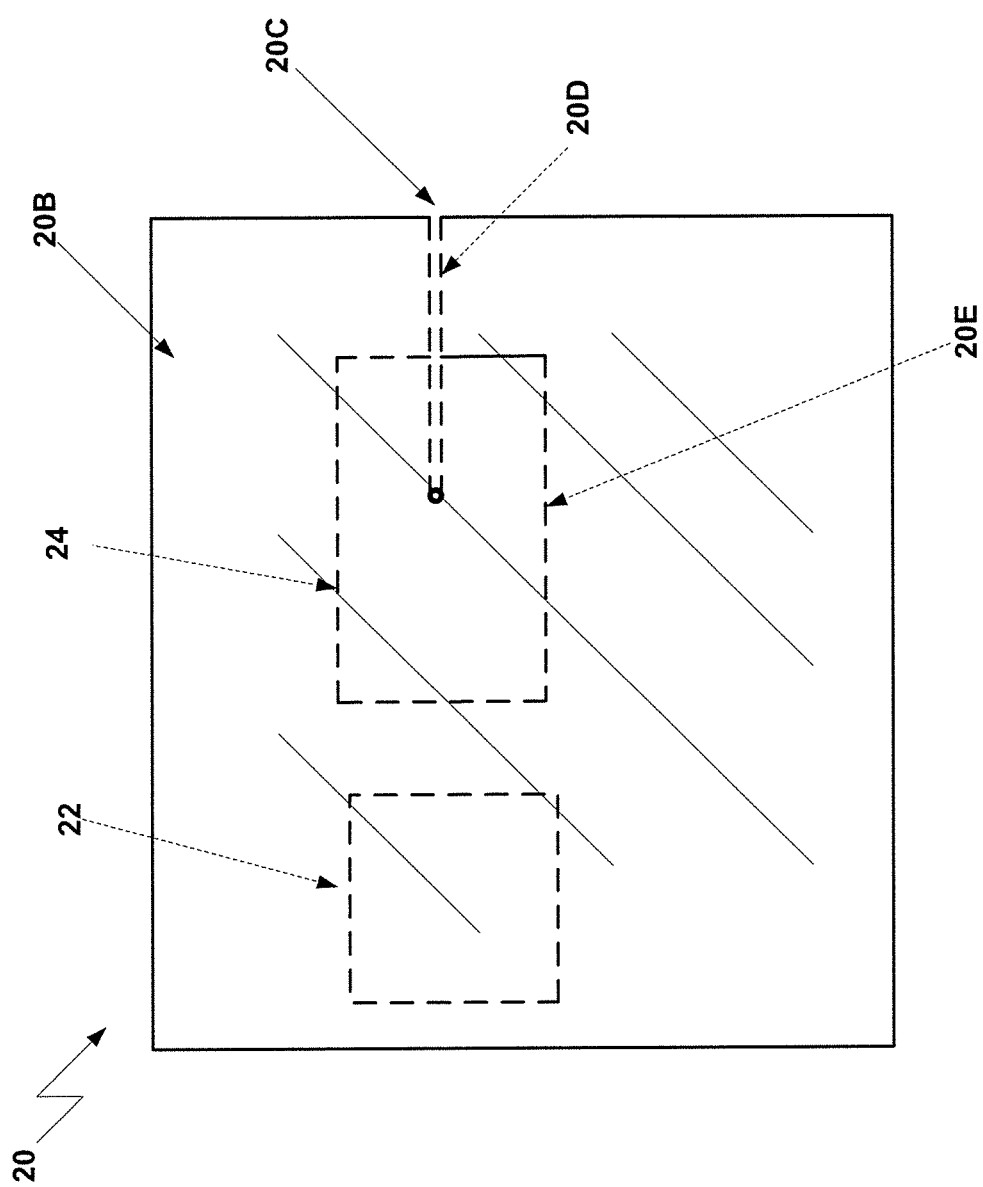
FIG. 4B is a diagrammatic bottom view of the first or second embodiment showing a translucent bottom surface.

It should be noted that the bottom portion 20B of the housing 20A may comprise an open bottom as shown in FIG. 4A or may comprise a translucent bottom layer as shown in FIG. 4B.

Thus, the present invention 20 provides a simple, reliable and repeatable means for gaining access and/or disposing of an item precisely within the reticular dermis.

In an exemplary system for monitoring a physiological analyte, the sensor system obtains a series of measurements relating to analyte levels in a user. The sensor system can be worn, for example, in the abdomen region of a patient. A small sensor can be placed on or into the patient to obtain readings of analyte values using, for example, subcutaneous analyte, lymphatic fluid analyte, reticular dermis analyte, or blood analyte readings. The sensor can be placed into the patient using a needle that extends into the patient, deposits the sensor, and then retracts and can be discarded. An applicator or other similar device can contain the needle and be used for inserting the sensor. The continuous analyte sensor system can also be a transdermal device, an intravascular device, or a non-invasive device.

The Continuous analyte sensor system may include a number of components to obtain analyte measurements, store the data, calculate analyte levels, communicate with dedicated display and perform other tasks. For example, although not illustrated, continuous analyte sensor system may include nonvolatile memory for storing historical data regarding analyte values, a processor, a battery, and a wireless transmitter. The wireless transmitter may provide any type of wireless communications, including a Bluetooth connection, WiFi connection, RF connection, and others. The wireless communications may occur, in some embodiments, between paired, authenticated devices, and may use encryption and other cryptographic techniques to ensure that communications remain confidential.

While illustrated as a single unit, the wireless transmitter may be removable from the continuous analyte sensor system and reusable with multiple sensors as the sensors are replaced. Further, the continuous analyte sensor system can include other components to facilitate data communications. For example, the continuous analyte sensor system may include wired ports, such as a USB port, Ethernet port, and others, for communicating with other devices and providing data relating to analyte levels. The continuous analyte sensor system may include the processing circuitry, such as a processor, memory, and a battery, as part of the sensor electronics. The sensor electronics may be included in the continuous analyte sensor system or the transmitter.

The sensor portion of the continuous analyte sensor system may be removable and replaceable, allowing a patient to change to a new sensor periodically, such as every week. Similarly, the transmitter may detach and be removable from the continuous analyte sensor system, allowing replacement as needed, such as every six months.

A Continuous analyte sensor system may obtain samples at predetermined intervals, such as every few seconds, every thirty seconds, every minute, or on demand in response to a command from a user. In one embodiment, the wireless transmitter can be turned off to conserve battery life, and measurements taken over a period of time can be wirelessly transmitted to a dedicated display in a batch transfer. For example, the continuous analyte sensor system can wake up the wireless transmitter every five minutes, transfer data relating to analyte measurements taken over the last five minutes, and transfer the data to the dedicated display. The wireless transmitter can then be turned off again to conserve battery life. While an example of transferring data every five minutes has been provided, it will be appreciated that longer or shorter time periods can be used, and the time period can be configured by a user via dedicated display.

The system may have a state determined by the continuous analyte sensor system and its transmitter. One exemplary system state includes not started, such as when a sensor has not yet been inserted into the subject or when the user has not yet activated the continuous analyte sensor system. Another example is a sensor warm-up period, which may last for a period of time, such as two hours, when the sensor is warming up and acclimating to insertion in the user's body. The sensor warm-up state may also include a calibration period. Other examples of system states include in calibration or out of calibration. A sensor and/or continuous analyte sensor system may be in calibration when it has been calibrated within a predetermined interval, such as within the last twelve hours, and out of calibration if a predetermined duration (e.g. twelve hours) has passed since the last calibration. Another exemplary system state is sensor stopped. The sensor stopped state may occur, for example, when a user seeks to replace the sensor portion of the analyte sensor system.

Implementations described herein can include a system for a subject, or in exemplary embodiments, one or more caretakers (e.g., a parent, spouse or healthcare practitioner) to remotely monitor health characteristics of one or more subjects. The health characteristics can include an analyte concentration of a subject, such as glucose, or a bodily function, such as heart rate, blood pressure, temperature and the like. In addition, other characteristics of a subject can be monitored to facilitate care of a subject, such as a location of the subject, state of a subject (e.g., exercising, sleeping, or working) and the like. The health characteristics and other characteristics can be gathered using a subject monitoring system that incorporates a computing device, such as a smartphone, and one or more sensors, such a continuous glucose sensor, heart-rate monitor, GPS device, etc. Additionally, a user can manually input information into the computing device, such as meal information, medication administration times and amounts, and the like. The information gathered by the subject monitoring system can then be transmitted to one or more remote monitors used by caretakers. The caretaker(s) can then receive information about the subject's health condition using a remote monitoring system. In some implementations, a monitoring system can transmit information directly to the one or more remote monitors and/or the subject monitoring system transmits information first to a remote server, which then transmits information to the subject monitor.

The analyte sensor system of the preferred embodiments can be designed with a variety of alternative configurations. In some embodiments, the sensor is connected to a fluid connection device. The fluid connection device in these embodiments can be any standard fluid connection device known in the art, such as a fluid coupler, or a fluid coupler custom manufactured to preferred specifications. On its first side, the fluid coupler is configured to couple to an existing catheter or cannula. The catheter (or cannula) is typically inserted into a vascular access device and/or into a hospital subject during a hospital stay. For example, the catheter can be inserted into an arterial line (e.g., for removing blood samples or for measuring blood pressure using a pressure transducer) or a venous line (e.g., for intravenous delivery of drugs and other fluids). In general practice, the catheter is inserted into the subject's blood vessel, for example, and maintained there for a period of time during the subject's hospital stay, such as part of the stay or during the entire stay (e.g., perioperatively). In one alternative embodiment, another vascular access device (e.g., other than a catheter) can be used to receive the sensor. In yet another alternative embodiment, the sensor system of the preferred embodiments can be inserted into a vascular access device (e.g., rather than the vascular system directly). Some examples of vascular access devices include but are not limited to catheters, shunts, automated blood withdrawal devices and the like.

In some embodiments, the sensor is inserted directly into, for example, the subject's reticular dermis system without a trocar or other medical device. In one such exemplary embodiment, a sheath covering the sensor is relatively rigid and supports the sensor during insertion. After the sensor has been inserted into the subject's skin, the supportive sheath is removed, leaving the exposed sensor in the subject's skin, such as the reticular dermis. In an alternative example, the sensor is inserted into, for example, a cannula and the cannula is removed, to leave the sensor in the subject's reticular dermis.

Sensors

Although the description herein refers to some implementations that include a continuous analyte sensor comprising a glucose sensor, the continuous analyte sensor may comprise other types of analyte sensors as well. Moreover, although some implementations refer to the glucose sensor as an implantable glucose sensor, other types of devices capable of detecting a concentration of glucose and providing an output signal representative of glucose concentration may be used as well. Furthermore, although the description herein refers to glucose as the analyte being measured, processed, and the like, other analytes may be used instead or as well including, for example, ketone bodies (e.g., acetone, acetoacetic acid and beta hydroxybutyric acid, lactate, etc.), glucagon, Acetyl Co A, triglycerides, fatty acids, intermediaries in the citric acid cycle, choline, insulin, cortisol, testosterone, and the like. In some implementations, other health characteristics of a host are monitored in addition to or instead of analyte monitoring described herein, including, but not limited to heart rate, blood pressure levels, blood oxygen levels, body temperature, caloric intake, medicament delivery and the like.

In an aspect, the sensor can include one or more optical sensors. An optical sensor can be configured to measure the optical absorption, optical emission, fluorescence, or phosphorescence, luminescence of an analyte or an associated tag or binding element, other tissues of interest, or combinations thereof. Such optical properties can be inherent optical properties of the analyte, e.g. autofluorescence, or can be optical properties of materials added or introduced into the body of the subject that interact with the analyte, other tissues of interest, or combinations thereof. Optical sensing of materials in blood, for example, is described in Mattley et al., "Blood characterization using UV/VIS spectroscopy" Proc. SPIE Advances in Fluorescence Sensing Technology II, Joseph R. Lakowicz; Ed. Vol. 2388, p. 462-470, 1995 and U.S. Pat. Nos. 5,589,932 and 7,027,134, each of which is incorporated herein by reference.

The devices may include one or more sensors configured to sense the blood glucose levels in the subject. The one or more sensors can include a glucose sensor that is either an integral part of the device, wherein the sensors is operably connected to the programmable microprocessor as described herein, or is in a separate device, for example a glucose sensing device in wireless communication with the programmable microprocessor in the device described herein. A number of different glucose monitors have been described using, for example, pin prick, transdermal, or implantable devices. See, e.g., U.S. Pat. Nos. 4,436,094; 4,953,552; 5,497,772; U.S. Patent Applications 2010/0049021; 2010/0081910; each of which is incorporated herein by reference. The one or more sensors can include one or more electrochemical- or photochemical-based sensors wherein a measurable chemical reaction occurs in response to the presence of one or more analyte. For example, many electrochemical sensors use enzymes as specifiers for the analyte. The enzymes cause a chemical reaction, such as a reduction reaction, and electrons released by the reaction are transferred to a mediator molecule, which itself is converted. The mediator then transfers the electrons to an electrode for electrochemical measurement or transfers the electrons to an indicator molecule for photochemical responses. Ferrocene derivatives and hexacyanoferrate are examples of one-electron mediators. Quinones are an example of two-electron mediators. A glucose sensor included in the device uses as the specifier an oxidoreductase that oxidizes glucose to gluconolactone. Electrons from the glucose are then transferred to the oxidized form of a mediator molecule, which in turn delivers the electrons to an electrode. The amount of electric current generated is proportional to the amount of glucose in the sample, and electronics within the sensor convert the signal, and the signal is communicated to the programmable microprocessor or the electronics module that is operably connected to the programmable microprocessor. See, e.g., Hones, et al., Diabetes Techn & Therap, 10: Supplement 1 S10-S26, 2008. Examples of commercially available glucose monitors using such technology in measuring blood glucose levels of a subject include but are not limited to OneTouch® blood glucose monitors (LifeScan-Johnson & Johnson, Milpitas, CA), Accu-Chek® blood glucose monitors (F. Hoffmann-Roche AG, Basel, Switzerland), and Ascensia® blood glucose monitors (Bayer HealthCare LLC, Tarrytown, NY). In an aspect, the glucose sensor for measuring blood glucose levels of a subject can include a continuous monitoring system, examples of which include but are not limited to Freestyle. Navigator® glucose monitor (Abbott Diabetes Care, Alameda, CA), Guardian® Real-Time glucose monitor (Medtronic MiniMed, Northridge, CA), and DexCom® SEVEN® glucose monitor (DexCom, San Diego, CA). See, e.g., Hermanides & DeVries, Diabetologia, 53: 593-596, 2010, which is incorporated herein by reference. The FreeStyle Navigator® glucose monitor, for example, is a biocompatible chip implanted into the abdomen or back of the upper arm of a subject and includes an external receiver. Similarly, blood glucose sensor-enabled radio frequency identification (RFID) devices have been described for active monitoring of glucose. See, e.g., Moore, J. Diabetes Sci. Technol. 3: 180-183, 2009, which is incorporated herein by reference. Miniaturized (0.5.times.0.5.times.5 mm) implantable glucose sensors can include the GLUCOWIZZARD® implantable glucose sensor that senses glucose levels and transmits the information to a proximal communicator. See, e.g., BIORASIS Storrs/Mansfield, Conn. A bio-sensor chip can include a passive transponder, glucose sensor, and integrated circuitry. See, e.g., U.S. Pat. No. 7,125,382 to Zhou entitled "Embedded Bio-sensor System," which is incorporated herein by reference. See, e.g., Digital Angel Corporation, St. Paul, MN Other methods for continuous monitoring of blood glucose levels of a subject include transcutaneous fluorescence lifetime-based microsensors or subcutaneous microelectromechanical systems (MEMS)-based sensors. See, e.g., U.S. Pat. No. 6,304,766; Nielsen, et al., J. Diabetes Sci. Technol. 3: 98-109; Li, et al., J. Diabetes Sci. Technol. 2: 1066-1074, 2008, each of which is incorporated herein by reference.

The one or more sensors can be configured to include an assembly for in vivo microdialysis. In vivo microdialysis allows for continuous sampling from the interstitial fluid of a tissue with minimal influence on surrounding tissues and/or whole body function. A microdialysis probe can be inserted into a tissue of interest, and perfused at a constant flow rate with a physiological buffer, e.g., saline. The tip of the probe consists of a semi-permeable membrane through which compounds in the interstitial fluid of the tissue can diffuse and subsequently be sampled from the outlet tubing of the probe.

In an aspect, the one or more analytes can include but are not limited to utilizable glucose, produced and/or released glycerol, free fatty acids, cAMP (indicative of beta-adrenergic receptor stimulation), hexokinase and phosphofructokinase or their enzymatic activities or products.

The device can include one or more sensors configured to sense one or more other physiological conditions of the subject including, but not limited to, pH, pCO2, blood flow, blood pressure, skin temperature, core temperature, tissue temperature, or blood oxygenation. The one or more sensors can also be configured to sense measures of physical activity of the subject as a means for estimating daily energy expenditure. Measures of physical activity of a subject include but are not limited to body temperature, heart rate, skin resistance, motion/acceleration, and velocity.

The one or more sensors can include one or more temperature sensors configured to measure temperature in one or more tissues. The temperature sensor can be a thermistor, a thermocouple, or a resistive temperature detector.

The one or more sensors can include one or more sensors that are calorimeters configured to measure caloric intake and/or energy expenditure. In an aspect, the one or more calorimeter can include an indirect calorimeter configured to assess the physical activity of the subject by periodically monitoring heart rate, body temperature, skin resistance, motion/acceleration sensing, velocity and providing an estimate of caloric intake/energy expenditure. The indirect calorimeter can include one or more of a temperature sensor, a heart rate sensor, an accelerometer, a global positioning system, or a combination thereof. See, e.g., U.S. Patent Application 2009/0240113, which is incorporated herein by reference. An example of a wireless patch system configured for estimating energy expenditure has been described and includes sensors, electrodes, and accelerometers. This system measures a variety of physiological conditions including temperature, heart rate, respiratory rate, and skin conductivity and uses this information in an algorithm to calculate the number of calories consumed, the number of calories burned, and the net yield. See, e.g., U.S. Patent Application 2010/0049004, which is incorporated herein by reference. Other examples of calorie counters based on activity measurements have been described. See, e.g., U.S. Pat. Nos. 4,100,401; 4,159,416; 5,815,954; and 7,334,472, each of which is incorporated herein by reference. Other means for performing calorimetry include but are not limited to the Haldane gravimetric method, open-circuit calorimeter with mask, spirographic method, assessment of heat loss and oxygen consumption.

The one or more sensors can be configured to detect an analyte that includes, but is not limited to, a biological marker, an antibody, an antigen, a peptide, a polypeptide, a neuropeptide, a protein, a complex, an enzyme, a hormone, a neurotransmitter, a nucleic acid, a cell (and, in some cases, a cell of a particular type, e.g. by methods used in flow cytometry), a cell fragment, a cellular component, a platelet, an organelle, a gamete, a pathogen, a lipid, a lipoprotein, an alcohol, an acid, an ion, an immunomodulator, a sterol, a carbohydrate, a saccharide, a polysaccharide, a glycoprotein, a metal, an electrolyte, a metabolite, an organic compound, an organophosphate, a drug, a therapeutic, a gas, a pollutant, or a tag. The one or more sensors can include one or more binding elements configured to interact with an analyte including, but not limited to, binding molecules, recognition elements, antibodies or fragments thereof, oligonucleotide or peptide based aptamers (see, e.g., Mok & Li Sensors 8: 7050-7084, 2008, which is incorporated herein by reference), receptors or ligands, artificial binding substrates (e.g. those formed by molecular imprinting), or any other examples of molecules and/or substrates capable of interacting with an analyte.

The one or more sensors can include a single sensor or an array of sensors, and is not limited to a particular number or type of sensor. The one or more sensors can be very small, comprising a sensor or array of sensors, having, for example, a biosensor, a chemical sensor (Snow Science, 2005, 307: 1942-1945), a gas sensor (Hagleitner et al., Nature, 2001 414:293-296), an electronic nose, a nuclear magnetic resonance imager (Yusa et al., Nature, 2005, 343:1001-1005). The foregoing references are each incorporated herein by reference. Further examples of sensors are provided in The Biomedical Engineering Handbook, Second Edition, Volume I, J. D. Bronzino, Ed., Copyright 2000, CRC Press LLC, pp. V-1-51-9; Morrison et al., "Clinical Applications of Micro- and Nanoscale Biosensors" in Biomedical Nanostructures. Edited by K. E. Gonsalves, C. L. Laurencin, C. R. Halberstadt, L. S, Nair. 2008, John Wiley & Sons, Inc.; and U.S. Pat. No. 6,802,811, each of which is incorporated herein by reference.

The one or more sensors operably connected with the electronics module and/or programmable microprocessor can include but are not limited to one or more biosensors, chemical sensors, pressure sensors, temperature sensors, flow sensors, viscosity sensors, shear sensors (e.g., for measuring the effective shear modulus of the fluid at a frequency or strain-rate), pH sensors, optical sensors (e.g., charged couple device (CCD) array), optical waveguide sensors, acoustic sensors, surface acoustic wave sensors, quartz microbalance sensors, metal oxide sensors, bulk acoustic wave sensors, plate acoustic wave sensors, electrical sensors, magnetic sensors, interdigitated microelectrode sensors, electrochemical sensors, electrically conducting sensors, artificial noses, electronic noses, electronic tongues, semiconductive gas sensors, mass spectrometers, near infrared and infrared spectrometers, ultraviolet sensors, visible light-based sensors, fluorescence spectrophotometers, conductive-polymers, gas-fluorescence spectrophotometers, impedance spectrometers, aptamer-based biosensors, ion mobility spectrometry, photo-ionization detectors, amplifying fluorescent polymer sensors, ion mobility spectrometry, electrical impedance, microgravimetric sensors, cantilever and microcantilever sensors, accelerometers, global positioning devices, clocks or time-keeping devices. See, e.g., U.S. Pat. Nos. 5,522,394; 5,873,835; 6,409,674; 6,111,520; 6,278,379; 6,475,639; 6,802,811; 6,855,115, 6,517,482; 6,675,030; 6,836,678; 6,954,662; 7,184,810; 7,299,080, and U.S. Patent Application 2005/0277839, each of which is incorporated herein by reference.

The one or more sensors of the device can be configured to send data regarding a physiological condition in the subject to the programmable microprocessor of the device or to an electronics module operably connected to the programmable microprocessor. Conversely, the electronics module can be configured to instruct the one or more sensors to collect and transmit data or other information regarding one or more physiological conditions or indicators thereof at specified regular intervals and/or when triggered by sensed events or by initiation of particular device activity. The device may further include information storage. For example, measurement of one or more physiological conditions may be collected and stored at specified times on a daily basis with an associated time stamp. More than one physiological condition may be measured simultaneously and associated with one another during processing. For example, measurement of temperature, or a localized temperature of an associated nerve tissue or circulatory tissue, can be assessed at the same time as measurement of blood glucose levels. A temperature measurement can also be triggered by other sensor activity such as when a measured exertion level reaches a specified limit value or immediately following caloric intake.

Detection

In some embodiments, the target area is identified by administering an imaging agent, such as a fluorescent dye, to a subject, which is then detected. In general, an imaging agent label provides a detectable signal. Non-limiting examples of labels useful in the invention include fluorescent dyes (e.g., fluorescein isothiocyanate, Texas red, rhodamine, and the like), enzymes (e.g., LacZ, CAT, horseradish peroxidase, alkaline phosphatase, I 2-galactosidase, .beta.-galactosidase, and glucose oxidase, acetylcholinesterase and others, commonly used as detectable enzymes), quantum dot-labels, chromophore-labels, enzyme-labels, affinity ligand-labels, electromagnetic spin labels, heavy atom labels, probes labeled with nanoparticle light scattering labels or other nanoparticles, fluorescein isothiocyanate (FITC), TRITC, rhodamine, tetramethylrhodamine, R-phycoerythrin, Cy-3, Cy-5, Cy-7, Texas Red, Phar-Red, allophycocyanin (APC), epitope tags such as the FLAG or HA epitope, and enzyme tags such as and hapten conjugates such as digoxigenin or dinitrophenyl, or members of a binding pair that are capable of forming complexes such as streptavidin/biotin, avidin/biotin or an antigen/antibody complex including, for example, rabbit IgG and anti-rabbit IgG; magnetic particles; electrical labels; thermal labels; luminescent molecules; phosphorescent molecules; chemiluminescent molecules; fluorophores such as umbelliferone, fluorescein, rhodamine, tetramethyl rhodamine, eosin, green fluorescent protein, erythrosin, coumarin, methyl coumarin, pyrene, malachite green, stilbene, *lucifer* yellow, Cascade Blue, dichlorotriazinylamine fluorescein, dansyl chloride, phycoerythrin, fluorescent lanthanide complexes such as those including Europium and Terbium, molecular beacons and fluorescent derivatives thereof, a luminescent material such as luminol; light scattering or plasmon resonant materials such as gold or silver particles or quantum dots; radiolabels or heavy isotopes including 14C, 123I, 124I, 131I, 125I, Tc99m, 32P, 35S or 3H; spherical shells; and probes labeled with any other signal generating label known to those of skill in the art, as described, for example, in Principles of Fluorescence Spectroscopy, Joseph R. Lakowicz (Editor), Plenum Pub Corp, 2nd edition (July 1999) and the 6 th Edition of the Molecular Probes Handbook by Richard P. Hoagland. Two or more different labels may be used together to detect two or more analytes in a single assay.

The User interface could include indicators, displays, buttons, touchscreens, head-mounted displays, and/or other elements configured to present information about the imaging system to a user and/or to allow the user to operate the imaging system. Additionally or alternatively, the imaging system could be configured to communicate with another system (e.g., a cellphone, a tablet, a computer, a remote server) and to present elements of a user interface using the remote system. The user interface could be disposed proximate to the light source, first camera, SLM, MD6, second camera, stage actuator, controller, or other elements of the imaging system or could be disposed away from other elements of the imaging system and could further be in wired or wireless communication with the other elements of the imaging system. The user interface could be configured to allow a user to specify some operation, function, or property of operation of the imaging system. The user interface could be configured to present an image of the target area generated by the imaging system or to present some other information to a user. Other configurations and methods of operation of a user interface are anticipated.

Communication system(s) may also be operated by instructions within the program instructions, such as instructions for sending and/or receiving information via a wireless antenna, which may be disposed of or in the imaging system. The communication system(s) can optionally include one or more oscillators, mixers, frequency injectors, etc. to modulate and/or demodulate information on a carrier frequency to be transmitted and/or received by the antenna. In some examples, the imaging system is configured to indicate an output from the controller (e.g., one or more images of the target area) by transmitting an electromagnetic or other wireless signal according to one or more wireless communications standards (e.g., Bluetooth, WiFi, IRdA, ZigBee, WiMAX, LTE). In various implementations, the described aspects may communicate over wireless shared media in accordance with a number of wireless protocols. Examples of wireless protocols may include various wireless local area network (WLAN) protocols, including the Institute of Electrical and Electronics Engineers (IEEE) 802.xx series of protocols, such as TFEE 802.11a/b/g/n, IEEE 802.16, IEEE 802.20, and so forth. Other examples of wireless protocols may include various wireless wide area network (WWAN) protocols, such as GSM cellular radiotelephone system protocols with GPRS, CDMA cellular radiotelephone communication systems with 1×RTT, EDGE systems, EV-DO systems, EV-DV systems, HSDPA systems, and so forth. Further examples of wireless protocols may include wireless personal area network (PAN) protocols, such as an Infrared protocol, a protocol from the Bluetooth Special Interest Group (SIG) series of protocols, including Bluetooth Specification versions v1.0, v1.1, v1.2, v2.0, v2.0 with Enhanced Data Rate (EDR), as well as one or more Bluetooth Profiles, and so forth. Yet another example of wireless protocols may include near-field communication techniques and protocols, such as electro-magnetic induction (EMI) techniques. An example of EMI techniques may include passive or active radio-frequency identification (RFID) protocols and devices. Other suitable protocols may include Ultra Wide Band (UWB), Digital Office (DO), Digital Home, Trusted Platform Module (TPM), ZigBee, and so forth.

In various implementations, the described aspects may comprise part of a cellular communication system. Examples of cellular communication systems may include CDMA cellular radiotelephone communication systems, GSM cellular radiotelephone systems, North American Digital Cellular (NADC) cellular radiotelephone systems, Time Division Multiple Access (TDMA) cellular radiotelephone systems, Extended-TDMA (E-TDMA) cellular radiotelephone systems, Narrowband Advanced Mobile Phone Service (NAMPS) cellular radiotelephone systems, third generation (3G) systems such as WCDMA, CDMA-2000, UMTS cellular radiotelephone systems compliant with the Third-Generation Partnership Project (3GPP), and so forth.

In various aspects, the electronics module includes the functionality to wirelessly receive and/or wirelessly transmit data, e.g., physiologic data, to a computer, such as a mobile computer.

Further, in various aspects, the electronics module may incorporate and/or be associated with, e.g., communicate with, various devices. Such devices may generate, receive, and/or communicate data, e.g., physiologic data. The devices include, for example, "intelligent" devices such as cellular phones, personal data assistants, or devices configured to be used by a health care provider or a patient to receive or transmit data to and from the analyte devices.

The mobile computer may be implemented as a mobile telephone. For example, the mobile computer may be implemented as a short-range, portable electronic device used for mobile voice or data communication over a network of specialized cell site base stations. The mobile telephone is sometimes known as or referred to as "mobile," "wireless," "cellular phone," "cell phone," or "hand phone (HP)."

In some examples, the communication system(s) could include one or more wired communications interfaces and the imaging system could be configured to indicate an output from the controller by operating the one or more wired communications interfaces according to one or more wired communications standards (e.g., USB, FireWire, Ethernet, RS-232). Wireless communication modes include any mode of communication between points that utilizes, at least in part, wireless technology including various protocols and combinations of protocols associated with wireless transmission, data, and devices. The points include, for example, wireless devices such as wireless headsets, audio and multimedia devices and equipment, such as audio players and multimedia players, telephones, including mobile telephones and cordless telephones, and computers and computer-related devices and components, such as printers.

Vehicles of communication include a network. In various aspects, the network may comprise local area networks (LAN) as well as wide area networks (WAN) including without limitation Internet, wired channels, wireless channels, communication devices including telephones, computers, wire, radio, optical or other electromagnetic channels, and combinations thereof, including other devices and/or components capable of/associated with communicating data. For example, the communication environments include in-body communications, various devices, various modes of communications such as wireless communications, wired communications, and combinations of the same.

The computer readable data storage may further contain other data or information, such as contain calibration data corresponding to a configuration of the imaging system, a calibration target, or some other information. Calibration, imaging, and/or other data may also be generated by a remote server and transmitted to the imaging system via communication system(s).

Preventing Fibrosis

The present invention provides for a proprietary device platform to optimize placement of the needle wholly within the dermal interstitium providing accurate data. Moreover, knowing the cellular and matrix components of the interstitium in ways previously unappreciated, allows for our proprietary materials that will not trigger interstitial fibrosis or other interfering reactions. These changes should lead to a more durable and optimized placement of needles and sensors.

Liquid Biopsies, Bio Markers

Sampling of interstitial fluid for purpose of liquid biopsies by doing that potentially for types of cancer, determining drug therapies, accessing bio markers, chemical toxins including insecticides and bio threats, chemical exposures, environmental exposures, carcinogens or neuro toxins, allergens, analytical components.

Biomarkers for many diseases are found in the blood. As subsequently disclosed, biomarkers detected in a liquid biopsy sample are used to generate antibodies against them using known methods in the art. The anti-tumor antibodies are used to coat nanoparticles in the inventive method, where a lesion can be imaged regardless of the lesion size or location in the body. The method is not limited to tumor detection and/or therapy. As only one example, detecting an antibody against anti-beta-amyloid protein present in Alzheimer's disease in a liquid biopsy specimen, the method renders the plaque visible with the nanoparticles and accessible to the inventive treatment. As another example, the method can also be used to detect and/or treat inflammatory processes, etc.

A liquid biopsy, the collection of, for example, interstitial fluid, blood, or other liquids from a patient with primary or recurrent disease and the analysis of biomarkers in the sample is increasingly being recognized as a viable, noninvasive method of monitoring a patient's disease progression, regression, recurrence, and/or response to treatment.

A relatively recent concept is the use of free circulating tumor DNA that is released from the tumor for example into the blood for methylation analysis as an indicator for tumor load in the body of the patient. This ability to isolate and to characterize extracellular nucleic acids from tumor patients with very sensitive and highly specific methods led to the term "liquid biopsy". As a result, physicians no longer depend exclusively on a single examination of tissue biopsies and body scans. The detection of small amounts of methylated tumor DNA with high backgrounds of unmethylated non-tumor DNA in such a liquid biopsy greatly challenges the sensitivity of the detection methods.

One of the main strengths of microscale techniques for biology is the reduced volumes of reagents needed per assay. This benefit is typically discussed as being a source of significant and direct cost savings per endpoint. In the context of cell-based assays, more endpoints can be obtained per cell sample, a fact which is a particularly important point in the area of primary cell analysis. Further, by obtaining more endpoints per cell sample, the statistical relevance of results can be directly impacted, specifically in analyses that involve rare cell types or samples with small cell numbers. In the area of clinical diagnostics and monitoring, biopsies and tissue sampling are being pushed to be less invasive. As a result, these procedures typically result in smaller and smaller cell samples. Various types of liquid biopsies often fall into this category such as, for example, interstitial fluid or blood samples from patients with lung, prostate, or breast cancer for analysis of circulating tumor cells (CTCs) or the fluid from bronchoalveolar lavages to diagnose lung cancer. Depending upon the extent of disease and volume of fluid sampled, these types of liquid biopsies may only procure hundreds or thousands of the cell type desired for analysis. With such low numbers of cells, it can be difficult to achieve a robust readout and perform replicates using macroscale techniques. In one embodiment one obtains a liquid biopsy sample. Such a sample may be obtained from, e.g., interstitial fluid, blood, urine, cerebrospinal fluid (CFS), aqueous or vitreous or abdominal cavity fluid, lymph node fluid, bladder fluid, milk duct fluid, sputum, gastric fluid, bile duct fluid, sinus fluid, etc. The patient may or may not have any clinical symptoms. The patient may or may not have history of a family disposition for tumors in and/or cancer of the breast, brain, lung, prostate, ovary, pancreas, etc., or a genetic abnormality leading to progression in diseases such as, e.g., Alzheimer's, Parkinson's, post traumatic brain syndrome, brain tumor, other neurological disease, age related macular degeneration, an infectious disease, an immune response, etc. The method evaluates the components of the sample for cell free nucleic acid-based biomarkers including but not limited to micoRNA and microDNA; protein-based biomarkers, extracellular vesicle (EV)-based biomarkers that are contained within exosomes, extracellular vesicles, or microvesicles, and circulating tumor cell (CTC)-based biomarkers. The method uses methodologies such as next generation sequencing (NGS) or recombinant affinity reagents fabricated into nanostructures such as carbon nanotubes, nanowires, quantum dots, or gold nanoshells, to enhance their detection with the use of, e.g., surface-enhanced Raman scattering (SERS), as known in the art.

Using the Interstitium for Injection

The invention provides, for example, injection of active pharmaceutical ingredients into the interstitium. The invention provides a needle delivery system for Interstitial, injection, that is, directly into the interstitial fluid. A proprietary needle system with the proprietary guide to find that pocket for better injection of insulin; Microbiome area skin microbiome; Community of bacteria live under the skin, Imbalances cause issues that can be monitored; deliver probiotics—live bacterial into interstitium; bioactive compounds and monitor release onto skin as well as allergy shots-targeting the "Mast Cells".

Examples of active pharmaceutical ingredient compounds which may be injected into the interstitium by the technology of the invention includes, for example, any therapy (e.g., therapeutic or prophylactic agent) which is useful, has been used, is currently being used, or may be used for the prevention, treatment and/or management of cancer can be used to prevent, treat, and/or manage the patient whose neoplasia and/or cancer stem cells are monitored in accordance with the compounds and methods of the invention. Also, such neoplasia and/or cancer stem cell monitoring can be employed in conjunction with any therapy for cancer according to the instant invention. Therapies (e.g., therapeutic or prophylactic agents) include but are not limited to peptides, polypeptides, fusion proteins, nucleic acid molecules, small molecules, mimetic agents, synthetic drugs, inorganic molecules, and organic molecules. Non-limiting examples of cancer therapies include chemotherapies, radiation therapies, hormonal therapies, anti-angiogenesis therapies, targeted therapies, and/or biological therapies including immunotherapies and surgery. In certain embodiments, a prophylactically and/or therapeutically effective regimen comprises the administration of a combination of therapies. In certain embodiments, ORG34517, PT150, TPR-1, OR-1, MR-1, TCY1, PT157, PT158, PT159, PT160, PT162, PT163, PT164, PT165, PT166, PT167, combinations thereof, and pharmaceutically acceptable salts thereof can be administered as an agent, alone or in combination with other active agents and/or other therapies, to treat and/or prevent neoplasia. In certain embodiments, RU486 (mifepristone) can be administered as an agent to treat or prevent neoplasia.

Examples of cancer therapies which may be administered alone or in combination, include but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthracyclin; anthramycin; asparaginase; asperlin; azacitidine (Vidaza); azetepa; azotomycin; batimastat; benzodepa; bicalutamide; bisantrene hydrochloride; bisnafide dimesylate; bisphosphonates (e.g., pamidronate (Aredria), sodium clondronate (Bonefos), zoledronic acid (Zometa), alendronate (Fosamax), etidronate, ibandornate, cimadronate, risedromate, and tiludromate); bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine (Ara-C); dacarbazine; dactinomycin; daunorubicin hydrochloride; decitabine (Dacogen); demethylation agents, dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; EphA2 inhibitors; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; histone deacetylase inhibitors (HDAC-Is) hydroxyurea; idarubicin hydrochloride; ifosfamide; ilmofosine; imatinib mesylate (Gleevec, Glivec); interleukin II (including recombinant interleukin II, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; lenalidomide (Revlimid); letrozole; leuprolide acetate; liarozole hydrochloride; lometrexol sodium; lomustine; losoxantrone hydrochloride; masoprocol; maytansine; mechlorethamine hydrochloride; anti-CD2 antibodies (e.g., siplizumab (MedImmune Inc.; International Publication No. WO 02/098370, which is incorporated herein by reference in its entirety)); megestrol acetate; melengestrol acetate; melphalan; menogaril; mercaptopurine; methotrexate; methotrexate sodium; metoprine; meturedepa; mifepristone; mitindomide; mitocarcin; mitocromin; mitogillin; mitomalcin; mitomycin; mitosper; mitotane; mitoxantrone hydrochloride; mycophenolic acid; nocodazole; nogalamycin; ORG 34517; ormaplatin; oxaliplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; RU486; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other examples of cancer therapies include but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-I; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, dioxamycin; diphenyl spiromustine; docetaxel; docosanol; dolasetron; doxifluridine; droloxifene; dronabinol; duocarmycin SA; ebselen; ecomustine; edelfosine; edrecolomab; eflomithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; HMG CoA reductase inhibitors (e.g., atorvastatin, cerivastatin, fluvastatin, lescol, lupitor, lovastatin, rosuvastatin, and simvastatin); hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; LFA-3TIP (Biogen, Cambridge, Mass.; International Publication No. WO 93/0686 and U.S. Pat. No. 6,162,432); liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RH retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; gamma secretase inhibitors, single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; 5-fluorouracil; leucovorin; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; thalidomide; velaresol; veramine; verdins; verteporfin; vinorelbine; vinxaltine; anti-integrin antibodies (e.g., anti-integrin a.sub.vb.sub.3 antibodies); vorozole; zanoterone; zeniplatin; zilascorb; and zinostatin stimalamer.

A non-limiting list of compounds that could be used to target cancer stem cells includes: inhibitors of interleukin-3 receptor (IL-3R) and CD123 (including peptides, peptide-conjugates, antibodies, antibody-conjugates, antibody fragments, and antibody fragment-conjugates that target IL-3R or CD123); cantharidin; norcantharidin and analogs and derivatives thereof; Notch pathway inhibitors including gamma secretase inhibitors; sonic hedgehog/smoothened pathway inhibitors including cyclopamine and analogs thereof; antibodies to CD96; certain NF-kB/proteasome inhibitors including parthenolide and analogs thereof; certain triterpenes including celastrol; certain mTOR inhibitors; compounds and antibodies that target the urokinase receptor; sinefungin; certain inosine monophosphate dehydrogenase (IMPDH) inhibitors; PPAR-alpha and PPAR-gamma agonists and antagonists (including pioglitazone, tesaslitazar, muraglitazar, peliglitazar, lobeglitazone, balaglitazone, ragaglitazar, rosiglitazone, farglitazar, sodeiglitazar, reglitazar, naveglitazar, oxeglitazar, metaglidasen, netoglitazone, darglitazone, englitazone, thiazolidinediones, aleglitazar, edaglitazone, rivoglitazone, troglitazone, imiglitazar, and sipoglitazar); telomerase inhibitors; antibodies to EpCAM (ESA); GSK-3 beta agonists and antagonists (including Lithium, 6-bromoinirubin-3'-oxime (BIO), TDZD8); Wnt pathway inhibitors including antibodies to frizzled or small molecules that inhibit disheveled/frizzled or beta catenin; anti-CD20 antibodies and conjugates (e.g. Rituxan, Bexxar, Zevalin) for novel use in multiple myeloma or melanoma; anti-CD133 antibody; anti-CD44 antibody; antibodies to IL-4; certain differentiation agents such as versnarinone; compounds that target CD33 such as an antibody or betulinic acid; compounds that target lactadherin such as an antibody; small molecules or antibodies that target CXCR4 or SDF-1; small molecules or antibodies that target multi-drug resistance pumps; inhibitors of survivin; inhibitors of XIAP; small molecules that target Bcl-2; antibodies to CLL-1; and furin inhibitors (such as cucurbitacins).

An additional non-limiting list of compounds that could also be used to target cancer and/or cancer stem cells includes: i) antibodies, antibody fragments, and proteins that are either naked or conjugated to a therapeutic moiety that target certain cell surface targets on cancer stem cells, or ii) small molecules known in the art including ones that can be further optimized (e.g., via chemistry) or identified via a cancer stem cell-based screen (e.g., such as one that would determine whether a compound impairs proliferation or viability of a cancer stem cell through standard methods, the cell surface and intracellular targets including (not meant to be exhaustive) are: Rex1 (Zfp42), CTGF, Activin A, Wnt, FGF-2, HIF-1, AP-2gamma, Bmi-1, nucleostemin, hiwi, Moz-TIF2, Nanog, beta-arrestin-2, Oct-4, Sox2, stella, GDF3, RUNX3, EBAF, TDGF-1, nodal, ZFPY, PTNE, Evi-1, Pax3, Mc1-1, c-kit, Lex-1, Zfx, lactadherin, aldehyde dehydrogenase, BCRP, telomerase, CD133, Bcl-2, CD26, Gremlin, and FoxC2.

In some embodiments, the therapy(ies) is an immunomodulatory agent. Non-limiting examples of immunomodulatory agents include proteinaceous agents such as cytokines, peptide mimetics, and antibodies (e.g., human, humanized, chimeric, monoclonal, polyclonal, Fvs, ScFvs, Fab or F(ab)2 fragments or epitope binding fragments), nucleic acid molecules (e.g., antisense nucleic acid molecules and triple helices), small molecules, organic compounds, and inorganic compounds. In particular, immunomodulatory agents include but are not limited to methotrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamides (e.g., leflunamide), T cell receptor modulators, cytokine receptor modulators, and modulators mast cell modulators. Particularly preferred auxiliary immunomodulatory substances are cytokines, such as monokines, lymphokines, interleukins or chemokines, that further promote the innate immune response, such as IL-1, IL-1 receptor antagonist, IL-2, EL-3, EL-4, IL-5, IL-6, EL-7, IL-8, EL-9, ELIO, IL-12, EL-13, EL-14, EL-15, EL-16, IL-17, EL-18, IL-19, EL-20, EL-21, EL-22, DL-23, EL-24, IL-25, EL-26, EL-27, EL-28, EL-29, EL-30, EL-31, EL-32, EL-33, INF-alpha, EFN-beta, INF-gamma, GM-CSF, G-CSF, M-CSF, LT-beta or TNF-alpha, growth factors, such as hGH. Other examples of immunomodulatory agents can be found, e.g., in U.S. Publication No. 2005/0002934 A1 at paragraphs 259-275 which is incorporated herein by reference in its entirety. In one embodiment, the immunomodulatory agent is a chemotherapeutic agent. In an alternative embodiment, the immunomodulatory agent is an immunomodulatory agent other than a chemotherapeutic agent. In some embodiments, the therapy(ies) used in accordance with the invention is not an immunomodulatory agent.

In some embodiments, the therapy(ies) is an anti-angiogenic agent. Non-limiting examples of anti-angiogenic agents include proteins, polypeptides, peptides, fusion proteins, antibodies (e.g., human, humanized, chimeric, monoclonal, polyclonal, Fvs, ScFvs, Fab fragments, F(ab).sub.2 fragments, and antigen-binding fragments thereof) such as antibodies that specifically bind to TNF-alpha, nucleic acid molecules (e.g., antisense molecules or triple helices), organic molecules, inorganic molecules, and small molecules that reduce or inhibit angiogenesis. Other examples of anti-angiogenic agents can be found, e.g., in U.S. Publication No. 2005/0002934 A1 at paragraphs 277-282, which is incorporated by reference in its entirety. In other embodiments, the therapy(ies) is not an anti-angiogenic agent.

In certain embodiments, the therapy(ies) is an alkylating agent, a nitrosourea, an antimetabolite, and anthracyclin, a topoisomerase II inhibitor, or a mitotic inhibitor. Alkylating agents include but are not limited to busulfan, cisplatin, carboplatin, chlorambucil, cyclophosphamide, ifosfamide, decarbazine, mechlorethamine, mephalen, and themozolomide. Nitrosoureas include, but are not limited to carmustine (BCNU) and lomustine (CCNU). Antimetabolites include but are not limited to 5-fluorouracil, capecitabine, methotrexate, gemcitabine, cytarabine, and fludarabine. Anthracyclins include but are not limited to daunorubicin, doxorubicin, epirubicin, idarubicin, and mitoxantrone. Topoisomerase II inhibitors include, but are not limited to, topotecan, irinotecan, etopiside (VP-16), and teniposide. Mitotic inhibitors include but are not limited to taxanes (paclitaxel, docetaxel), and the *vinca* alkaloids (vinblastine, vincristine, and vinorelbine). In some embodiments of the invention, the therapy(ies) includes the administration cantharidin or an analog thereof. The invention includes the use of agents that target cancer stem cells. In certain embodiments, the agent acts alone. In other embodiments, the agent is attached directly or indirectly to another therapeutic moiety. Non-limiting examples of therapeutic moieties include, but are not limited to alkylating agents, antimetabolites, plant alkaloids, cytotoxic agents, chemotherapeutic agents (e.g., a steroid, cytosine arabinoside, fluoruracil, methotrexate, aminopterin, mitomycin C, demecolcine, etoposide, mithramycin, calicheamicin, CC-1065, chlorambucil or melphalan), radionuclides, therapeutic enzymes, cytokines, toxins including plant-derived toxins, fungus-derived toxins, bacteria-derived toxin (e.g., deglycosylated ricin A chain, a ribosome inactivating protein, alpha-sarcin, aspergillin, restirictocin, a ribonuclease, a diphtheria toxin, *Pseudomonas* exotoxin, a bacterial endotoxin or the lipid A moiety of a bacterial endotoxin), growth modulators and RNase. In some embodiments, the agent used is an agent that binds to a marker, e.g., an antigen on a cancer stem cell. In a specific embodiment, the agent binds to an antigen that is expressed at a greater level on cancer stem cells than on normal stem cells. In a specific embodiment, the agent binds specifically to a cancer stem cell antigen that is not a normal stem cell. In other embodiments, the therapy(ies) is an agent that binds to a marker on cancer stem cells. In one embodiment, the agent that binds to a marker on cancer stem cells is an antibody or an antibody conjugated to a therapeutic moiety or an antibody fragment conjugated to a therapeutic moiety.

For example, in a specific embodiment, the agent binds specifically to the IL-3 Receptor (IL-3R). In some embodiments, the agent that binds to the IL-3R is an antibody or an antibody fragment that is specific for IL-3R. In some embodiments, the antibody or antibody fragment is conjugated either chemically or via recombinant technology to a therapeutic moiety (e.g., a chemotherapeutic agent, a plant-, fungus- or bacteria-derived toxin, a radionuclide) using a linking agent to effect a cell killing response. In certain embodiments, the antibody, antibody-conjugate, antibody fragment, or antibody fragment-conjugate binds to the .alpha.-subunit of IL-3R (i.e., the CD123 antigen). In other embodiments, the antibody, antibody-conjugate, antibody fragment, or antibody fragment-conjugate binds to the IL-3R, containing both the .alpha. and .beta. subunits. Methods for preparing antibodies to IL-3R and mimetics of antibodies to IL-3R are described in U.S. Pat. No. 6,733,743 B2, which is incorporated herein by reference in its entirety.

In other embodiments, the agent that binds to a marker on cancer stem cells is a ligand. In some embodiments, the ligand is a cytokine that binds to a cytokine receptor on cancer stem cells. In a particular embodiment, the ligand is interleukin-3 (IL-3) which can be conjugated to a therapeutic moiety that includes a chemotherapeutic agent, a plant-, fungus-, or bacteria-derived toxin, or a radionuclide. The IL-3-conjugate prophylactic and/or therapeutic therapy or regimen can be in the form of a recombinant fusion protein in embodiments where the conjugate is a toxin and the toxin is a protein, such as diphtheria toxin. Methods for preparing and isolating an IL-3-diphtheria toxin fusion protein (IL3DT) are described in Frankel et al., "Diphtheria toxin fused to human interleukin-3 is toxic to blasts from patients with myeloid leukemias," Leukemia 14:576 (2000) and Urieto et al., Protein Expression and Purification 33: 123-133 (2004), the disclosures of which are incorporated by reference in their entireties.

In certain embodiments, antibodies or fragments thereof that bind to a marker on cancer stem cells are substantially non-immunogenic in the treated subject. Methods for obtaining non-immunogenic antibodies include, but are not limited to, chimerizing the antibody, humanizing the antibody, and isolating antibodies from the same species as the subject receiving the therapy. Antibodies or fragments thereof that bind to markers in cancer stem cells can be produced using techniques known in the art. See, for example, paragraphs 539-573 of U.S. Publication No. 2005/0002934, which is incorporated by reference in its entirety.

In some embodiments, the therapy comprises the use of X-rays, gamma rays and other sources of radiation to destroy cancer stem cells and/or cancer cells. In specific embodiments, the radiation therapy is administered as external beam radiation or teletherapy, wherein the radiation is directed from a remote source. In other embodiments, the radiation therapy is administered as internal therapy or brachytherapy wherein a radioactive source is placed inside the body close to cancer stem cells, cancer cells and/or a tumor mass.

In some embodiments, the therapy used is a proliferation based therapy. Non-limiting examples of such therapies include chemotherapy and radiation therapy as described supra.

Currently available therapies and their dosages, routes of administration and recommended usage are known in the art and have been described in such literature as the Physician's Desk Reference (60th ed., 2006).

In a specific embodiment, cycling therapy involves the administration of a first cancer therapeutic for a period of time, followed by the administration of a second cancer therapeutic for a period of time, optionally, followed by the administration of a third cancer therapeutic for a period of time and so forth, and repeating this sequential administration, i.e., the cycle in order to reduce the development of resistance to one of the cancer therapeutics, to avoid or reduce the side effects of one of the cancer therapeutics, and/or to improve the efficacy of the cancer therapeutics.

When two prophylactically and/or therapeutically effective regimens are administered to a subject concurrently, the term "concurrently" is not limited to the administration of the cancer therapeutics at exactly the same time, but rather, it is meant that they are administered to a subject in a sequence and within a time interval such that they can act together (e.g., synergistically to provide an increased benefit than if they were administered otherwise). For example, the cancer therapeutics may be administered at the same time or sequentially in any order at different points in time; however, if not administered at the same time, they should be administered sufficiently close in time so as to provide the desired therapeutic effect, preferably in a synergistic fashion. The combination cancer therapeutics can be administered separately, in any appropriate form and by any suitable route. When the components of the combination cancer therapeutics are not administered in the same pharmaceutical composition, it is understood that they can be administered in any order to a subject in need thereof. For example, a first prophylactically and/or therapeutically effective regimen can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the second cancer therapeutic, to a subject in need thereof. In various embodiments, the cancer therapeutics are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the cancer therapeutics are administered within the same office visit. In another embodiment, the combination cancer therapeutics are administered at 1 minute to 24 hours apart.

In a specific embodiment, the combination therapies have the same mechanism of action. In another specific embodiment, the combination therapies each have a different mechanism of action.

Compounds which may be administered by the technology of the invention include, alone or in combination, at least one anti-anxiety drug, at least one antidepressant drug, and at least one neuroleptic medication and combinations thereof, wherein the at least one anti-anxiety drug is selected from the group consisting of alprazolam, bromazepam, diazepam, lorazepam, clonazepam, temazepam, oxazepam, flunitrazepam, triazolam, chlordiazepoxide, flurazepam, estazolam, nitrazepam, and pharmaceutically acceptable salts, isomers, and mixtures thereof; and/or at least one antidepressant drug selected from the group consisting of citalopram, escitalopram oxalate, fluoxetine, fluvoxamine, paroxetine, sertraline, dapoxetine; venlafaxine and duloxetine; harmaline, iproniazid, isocarboxazid, nialamide, pargyline, phenelzine, selegiline, toloxatone, tranylcypromine, brofaromine, moclobemide; amitriptyline, amoxapine, butriptyline, clomipramine, desipramine, dibenzepin, dothiepin, doxepin, imipramine, iprindole, lofepramine, melitracen, nortriptyline, opipramol, protriptyline, trimipramine; maprotiline, mianserin, nefazodone, trazodone, and pharmaceutically acceptable salts, isomers, and combinations thereof, and/or at least one neuroleptic drug selected from the group consisting of Haloperidol, Droperidol, Benperidol, Triperidol, Melperone, Lenperone, azaperone, Domperidone, risperidone, Chlorpromazine, Fluphenazine, Perphenazine, Prochlorperazine, Thioridazine, Trifluoperazine, Mesoridazine, Periciazine, Promazine, Triflupromazine, Levomepromazine, Promethazine, Pimozide, Cyamemazine, Chlorprothixene, Clopenthixol, Flupenthixol, Thiothixene, Zuclopenthixol, Clozapine, Olanzapine, Risperidone, Quetiapine, Ziprasidone, Amisulpride, Asenapine, Paliperidone, Iloperidone, Zotepine, Sertindole, Lurasidone, Aripiprazole, and pharmaceutically acceptable salts, isomers, and combinations thereof, in therapeutically effective amounts. In certain embodiments the agents are administered in the same dosage form. In certain embodiments the therapeutic agents are administered separately.

In particular embodiments, the invention provides a composition comprising therapeutic agents, alone or in combination, selected from the group consisting of at least one antianxiety drug, at least one antidepressant drug, and at least one neuroleptic medication and combinations thereof, wherein the at least one anti-anxiety drug is selected from the group consisting of alprazolam, bromazepam, diazepam, lorazepam, clonazepam, temazepam, oxazepam, flunitrazepam, triazolam, chlordiazepoxide, flurazepam, estazolam, nitrazepam, and pharmaceutically acceptable salts, isomers, and mixtures thereof; and/or at least one antidepressant drug selected from the group consisting of citalopram, escitalopram oxalate, fluoxetine, fluvoxamine, paroxetine, sertraline, dapoxetine; venlafaxine and duloxetine; hamialine, iproniazid, isocarboxazid, nialamide, pargyline, phenelzine, selegiline, toloxatone, tranylcypromine, brofaromine, moclobemide; amitriptyline, amoxapine, butriptyline, clomipramine, desipramine, dibenzepin, dothiepin, doxepin, imipramine, iprindole, lofepramine, melitracen, nortriptyline, opipramol, protriptyline, trimipramine; maprotiline, mianserin, nefazodone, trazodone, and pharmaceutically acceptable salts, isomers, and combinations thereof, and/or at least one neuroleptic drug selected from the group consisting of Haloperidol, Droperidol, Benperidol, Triperidol, Melperone, Lenperone, azaperone, Domperidone, Chlorpromazine, Fluphenazine, Perphenazine, Prochlorperazine, Thioridazine, Trifluoperazine, Mesoridazine, Periciazine, Promazine, Triflupromazine, Levomepromazine, Promethazine, Pimozide, Cyamemazine, Chlorprothixene, Clopenthixol, Flupenthixol, Thiothixene, Zuclopenthixol, Clozapine, Olanzapine, Risperidone, Quetiapine, Ziprasidone, Amisulpride, Asenapine, Paliperidone, Iloperidone, Zotepine, Sertindole, Lurasidone, Aripiprazole, and pharmaceutically acceptable salts, isomers, and combinations thereof. In certain embodiments the agents are in the same dosage form. In certain embodiments the therapeutic agents are in separate dosage forms.

The phrase "administering in combination" as used herein refers to any form of administration of one or more therapeutic agents selected from the group consisting of at least one anti-anxiety drug, at least one antidepressant drug, and at least one neuroleptic medication and combinations thereof, wherein the at least one anti-anxiety drug is selected from the group consisting of alprazolam, bromazepam, diazepam, lorazepam, clonazepam, temazepam, oxazepam, flunitrazepam, triazolam, chlordiazepoxide, flurazepam, estazolam, nitrazepam, and pharmaceutically acceptable salts, isomers, and mixtures thereof; and/or at least one antidepressant drug selected from the group consisting of citalopram, escitalopram oxalate, fluoxetine, fluvoxamine, paroxetine, sertraline, dapoxetine; venlafaxine and duloxetine; harmaline, iproniazid, isocarboxazid, nialamide, pargyline, phenelzine, selegiline, toloxatone, tranylcypromine, brofaromine, moclobemide; amitriptyline, amoxapine, butriptyline, clomipramine, desipramine, dibenzepin, dothiepin, doxepin, imipramine, iprindole, lofepramine, melitracen, nortriptyline, opipramol, protriptyline, trimipramine; maprotiline, mianserin, nefazodone, trazodone, and pharmaceutically acceptable salts, isomers, and combinations thereof, and/or at least one neuroleptic drug selected from the group consisting of Haloperidol, Droperidol, Benperidol, Triperidol, Melperone, Lenperone, azaperone, Domperidone, risperidone, Chlorpromazine, Fluphenazine, Perphenazine, Prochlorperazine, Thioridazine, Trifluoperazine, Mesoridazine, Periciazine, Promazine, Triflupromazine, Levomepromazine, Promethazine, Pimozide, Cyamemazine, Chlorprothixene, Clopenthixol, Flupenthixol, Thiothixene, Zuclopenthixol, Clozapine, Olanzapine, Risperidone, Quetiapine, Ziprasidone, Amisulpride, Asenapine, Paliperidone, Iloperidone, Zotepine, Sertindole, Lurasidone, Aripiprazole, and pharmaceutically acceptable salts, isomers, and combinations thereof; in therapeutically effective amounts. In certain embodiments the agents are in the same dosage form. In certain embodiments the therapeutic agents are in separate dosage forms.

The compositions and methods of the invention may also make use of one or more androgen receptor antagonists, such as in a combination with the glucocorticoid receptor antagonist of the invention. For example, the invention provides with at least one glucocorticoid receptor antagonist in combination with at least one androgen receptor antagonist, such as for example, ARN 509 (4-{7-[6-Cyano-5-(trifluoromethyl)-3-pyridinyl]-8-oxo-6-thioxo-5,7-diazaspiro[3.4]oct-5-yl}-2-fluoro-N-methylbenzamide). ARN-509 is a novel androgen receptor (AR) antagonist for the treatment of castration-resistant prostate cancer (CRPC). ARN-509 inhibits AR nuclear translocation and AR binding to androgen response elements and, unlike bicalutamide, does not exhibit agonist properties in the context of AR overexpression.

Another exemplary antiadrogen is bicalutamide, which has the chemical name (R,S)—N-(4-cyano-3-(4-fluorophenylsulfonyl)-2-hydroxy-2-methyl-3-(t-riflu-oromethyl)propanamide, Flutamide (brand name Eulexin), nilutamide (brand names Anandron and Nilandron) and bicalutamide (brand name Casodex) are nonsteroidal, "pure" antiandrogens; 5-alpha-reductase inhibitors such as finasteride (brand names Proscar and Propecia), dutasteride (brand name Avodart), bexlosteride, izonsteride, turosteride, and epristeride are antiandrogenic as they prevent the conversion of testosterone to dihydrotestosterone (DHT); Spironolactone (brand names Aldactone and Spirotone), a synthetic 17-spirolactone corticosteroid; Cyproterone acetate (brand names Androcur, Climen, Diane 35, and Ginette 35) is a synthetic steroid, a potent antiandrogen that also possesses progestational properties. Hydroxyflutamide.

In some embodiments, steroidal or nonsteroidal androgen receptor antagonists include but are not limited to flutamide, hydroxyflutamide, enzalutamide bicalutamide, nilutamide, or hydroxysteroid dehydrogenase inhibitor.

In one embodiment, the androgen receptor antagonist is enzalutamide (marketed as Xtandi® Astellas Pharma US, Inc.), also known as and referred to herein as MDV3100, having the chemical name 4-(3-(4-cyano-3-(trifluoromethyl)phenyl)-5,5-dimethyl-4-oxo-2-thioxoimida-zolidin-1-yl)-2-fluoro-N-methylbenzamide.

The compositions and methods of the invention may also make use of one or more androgen receptor antagonist, such as in a combination with the glucocorticoid receptor antagonist of the invention. The androgen receptor antagonist may be selected from the group consisting of, for example, flutamide, nilutamide, enzalutamide, bicalutamide, ketonazole, abiraterone, abiraterone acetate, orteronel, finasteride, dutasteride, bexlosteride, izonsteride, turosteride, episteride, dexamethasone, prednisone, leuprolide, goserelin, triptorelin, histrelin, estrogen, MDV3100, Cyproterone acetate, Spironolactone, flutamide, hydroxyflutamide, enzalutamide and combinations thereof.

The selective androgen receptor (AR) antagonists embodied herein have utility for numerous conditions and diseases such as but not limited to male contraception; treatment of a variety of male hormone-related conditions such as hypersexuality and sexual deviation; treatment of conditions including benign prostatic hyperplasia, acne vugaris, androgenetic alopecia, and hirsutism; purposefully preventing or counteracting masculinisation in the case of transsexual women undergoing sex reassignment therapy; an antineoplastic agent and palliative, adjuvant or neoadjuvant hormonal therapy in prostate cancer; and decreasing the incidence of, halting or causing a regression of prostate cancer.

Suitable PARP inhibitors for use in the compositions and methods of the invention include, but are not limited to, 4-[[3-[4-(cyclopropanecarbonyl)piperazine-1-carbonyl]-4-fluorophenyl]-methyl]-2H-phthalazin-1-one (Compound B, i.e., Olaparib), 4-iodo-3-nitrobenzamide (Iniparib), 2-[(2R)-2-methylpyrrolidin-2-yl]-1H-benzimidazole-4-carboxamide (ABT-888), 8-Fluoro-2-{4-[(methylamino)methyl]-phenyl}-1,3,4,5-tetrahydro-6H-azepino-[5,4,3-cd]indol-6-one (AGO 14699), 4-methoxy-carbazole (CEP 9722), 2-[4-[(3S)-piperidin-3-yl]phenyl]indazole-7-carboxamide hydrochloride (MK 4827), and 3-aminobenzamide, or a pharmaceutically acceptable salt thereof.

In some embodiments, the Glucocorticoid receptor antagonists, e.g., ORG34517, PT150, TPR-1, OR-1, MR-1, TCY1, PT157, PT158, PT159, PT160, PT162, PT163, PT164, PT165, PT166, PT167, combinations thereof, and pharmaceutically acceptable salts thereof composition described herein, is administered in combination with a poly ADP-ribose polymerase (PARP) inhibitor (e.g., BSI201, Olaparib (AZD-2281), ABT-888, AG014699, CEP 9722, MK 4827, KU-0059436 (AZD2281), LT-673,3-aminobenzamide). Other example PARP inhibitors include, i.e., pharmacological inhibitors of the enzyme poly ADP ribose polymerase (PARP). Suitable PARP inhibitors maybe iniparib, olaparib, rucaparib, veliparib, or CEP 9722.

Current PARP inhibitors in clinical trials include: Iniparib (Sanofi), Olaparib (Astra7eneca), Rucaparib (Pfizer), Veliparib (Abbott), CEP-9722 (Cephalon), MK4827 (Merck), BMN-673 (Biomarin), among others.

at least one additional active agent selected from the group consisting of molecules with potential to bind viral PS, annexin-5, anti-PS monoclonal or polyclonal antibodies, bavituximab, and/or bind to viral glucocorticoid response elements (GREs), retinazone and RU486 or derivatives, cell entry inhibitors, uncoating inhibitors, reverse transcriptase inhibitors, integrase inhibitors, transcription inhibitors, antisense translation inhibitors, ribozyme translation inhibitors, prein processing and targeting inhibitors, protease inhibitors, assembly inhibitors, release phase inhibitors, immunosystem modulators and vaccines, including, but not limited to Abacavir, Ziagen, Trizivir, Kivexa/Epzicom, Aciclovir, Acyclovir, Adefovir, Amantadine, Amprenavir, Ampligen, Arbidol, Atazanavir, Atripla, Balvir, Cidofovir, Combivir, Dolutegravir, Darunavir, Delavirdine, Didanosine, Docosanol, Edoxudine, Efavirenz, Emtricitabine, Enfuvirtide, Entecavir, Ecoliever, Famciclovir, Fomivirsen, Fosamprenavir, Foscarnet, Fosfonat, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Nucleoside analogues, Novir, Oseltamivir (Tamiflu), Peginterferon alfa-2a, Penciclovir, Peramivir, Pleconaril, Podophyllotoxin, Protease inhibitor, Raltegravir, Reverse transcriptase inhibitor, Ribavirin, Rimantadine, Ritonavir, Pyrimidine, Saquinavir, Sofosbuvir, Stavudine, Synergistic enhancer, Tea tree oil, Telaprevir, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Zalcitabine, Zanamivir, Zidovudine, and combinations thereof; at least one pharmaceutically acceptable carrier; and optionally, and at least one blister package; a lidded blister; a blister card or packet; a clamshell; an intravenous (IV) package, IV packette or IV container; a tray or a shrink wrap comprising the pharmaceutical composition and instructions for use of the pharmaceutical composition.

Other Uses

Acupuncture is an alternative medicine that treats patients by insertion and manipulation of needles in the body at selected points. The locations where the acupuncture needles are inserted are referred to herein as "acupuncture points" or simply just "acupoints". The location of acupoints in the human body has been developed over thousands of years of acupuncture practice, and maps showing the location of acupoints in the human body are readily available in acupuncture books or online. For example, see, "Acupuncture Points Map," found online at: www.acupuncturehealing.org/acupuncture-points-map.html, Acupoints are typically identified by various letter/number combinations, e.g., L6, S37. The maps that show the location of the acupoints may also identify what condition, illness or deficiency the particular acupoint affects when manipulation of needles inserted at the acupoint is undertaken.

References to the acupoints in the literature are not always consistent with respect to the format of the letter/number combination. Some acupoints are identified by a name only, e.g., Tongli. The same acupoint may be identified by others by the name followed with a letter/number combination placed in parenthesis, e.g., Tongli (HT5). Alternatively, the acupoint may be identified by its letter/number combination followed by its name, e.g., HT5 (Tongli). The first letter(s) typically refers to a body organ, or other tissue location associated with, or affected by, that acupoint. However, usually only the letter(s), not the name of the body organ, is used in referring to the acupoint, but not always. Thus, for example, the acupoint SP4 is the same as acupoint Spleen 4 which is the same as SP-4 which is the same as SP 4 which is the same as Gongsun. For purposes of this patent application, unless specifically stated otherwise, all references to acupoints that use the same name, or the same first letter and the same number, and regardless of slight differences in second letters and formatting, are intended to refer to the same acupoint.

An excellent reference book that identifies all of the traditional acupoints within the human body is WHO STANDARD ACUPUNCTURE POINT LOCATIONS IN THE WESTERN PACIFIC REGION, published by the World Health Organization (WHO), Western Pacific Region, 2008 (updated and reprinted 2009), ISBN 978 92 9061 248 7 (hereafter "WHO Standard Acupuncture Point Locations 2008"). The Table of Contents, Forward (page v-vi) and General Guidelines for Acupuncture Point Locations (pages 1-21), as well as pages 66, 71 and 199 (which illustrate with particularity the location of acupoints ST40, SP4 and LR8, respectively) are incorporated herein by reference. Moreover, the above-cited portions of the WHO Standard Acupuncture Point Locations 2008 reference book, with the exception of pages 66, 71 and 199, may be found as Appendix D in Applicant's earlier-filed patent application, U.S. patent application Ser. No. 13/622,497, filed Sep. 19, 2012, which application is incorporated herein by reference. The relevant information from pages 66, 71 and 199 of the WHO Standard Acupuncture Point Locations 2008 book is presented herein as FIGS. 1A, 1B and 1C, and accompanying text, respectively.

Electroacupuncture is quite similar to traditional acupuncture in that the same points are stimulated during treatment. As with traditional acupuncture, needles are inserted on specific points along the body. The needles are then attached to a device that generates continuous electric pulses using small clips. These devices are used to adjust the frequency and intensity of the impulse being delivered, depending on the condition being treated. Electroacupuncture uses two needles at a time so that the impulses can pass from one needle to the other. Several pairs of needles can be stimulated simultaneously, usually for no more than minutes at a time." "Acupuncture Today: Electroacupuncture". 2004 Feb. 1 (www.acupuncturetoday.com/abc/electroacupuncture.php).

The invention provides for the devices and methods of the invention to be used for, for example, the placement of acupuncture needles or electroacupuncture needles.

Bio-Artificial Organ

A significant portion of health care spending is for recurrent treatments for chronic diseases. Given the liver's complexity, there are no simple or widely effective medical solutions to acute liver failure. The only long-term cure for acute liver failure is surgical transplantation. Regenerative medicine offers not only the potential to treat a variety of diseases, but more importantly, to potentially cure them.

The liver is an organ divided into two principal lobes made up of functional units called lobules. A lobule consists of cords of hepatic cells arranged radially around a central vein. Between these cords are sinusoid spaces lined with phagocytic cells known as Kupffer cells. Oxygenated blood is provided to the liver via the hepatic artery while deoxygenated blood leaves the liver via the hepatic portal vein. Branches of these vessels deliver blood to the sinusoids, where oxygen, most nutrients and certain toxins are extracted into the hepatic cells.

More specifically, as glucose-rich blood passes through the liver, excess glucose is removed and stored as the polysaccharide glycogen. When the level of glucose in the blood drops below normal, glycogen will be broken down into glucose which is released by the hepatic cells into the bloodstream. The liver also assists protein metabolism by extracting and storing excess amino acids in the bloodstream for use in the construction of many plasma proteins, such as albumin. Bile, a solution of salts, bilirubin, cholesterol and fatty acids which assists in the emulsification of fats and intestinal absorption of lipids, is also produced by hepatic cells. It is not, however, normally secreted into the bloodstream by these cells but is instead transported to, and stored in, the gallbladder.

Of greater importance to this invention is not the liver's role in digestion of food but its role in regulating the concentration of wastes and toxins in the blood. Hepatic cells contain enzymes which either break down toxins carried in the blood, transform them into less harmful substances or, failing either of those processes, stores them. For example, metabolism of amino acids will result in the release of free amino acids and nitrogenous wastes, the latter of which are converted by hepatic cells to urea. In moderate amounts, this urea is harmless and is easily excreted by the kidneys and sweat glands. "Old" red blood cells and certain bacteria can also be destroyed and, in the case of the former, recycled by the Kupffer cells.

In short, the liver is vital to maintaining the body's normal biochemical state. Impairment or loss of its function can, therefore, be fatal. The medical art has developed several approaches to the treatment of, or compensation for, liver disease, damage and failure. In addition, humans (as well as many other species) are capable of regenerating lost or damaged liver tissue.

However, although supportive and pharmaceutical treatments or transplantation may alleviate or reverse many symptoms of liver disease, these methods all require time which an actually ill patient may not have. Further, while undergoing treatment, support for any loss of normal liver function must be provided to maintain or approximate metabolic homeostasis. A means, therefore, is needed which can perform the cleaning functions of the liver when it cannot, thus increasing the time available for treatment.

Extracorporeal liver perfusion (i.e., pumping blood through foreign liver tissue) has been a proposed means for treatment and support for many years, with mixed success. However, despite attempts to use liver tissue from 5 different species, immunological and other biochemical reactions limited the use of the perfusions and the patient died before a suitable transplant donor could be found.

In contrast, extracorporeal methods of purifying blood and plasma; i.e., by hemodialysis, hemoperfusion or hemofiltration are well-known and established in the art for treatment of renal insufficiencies. The major goal of these methods is to maintain fluid and electrolyte balance and rid the body of waste products.

In renal hemodialysis, blood is pumped into a dialyzer containing an artificial semipermeable membrane suspended in a dialysis solution. With a concentration gradient established across the membrane for a particular substance, flow from the blood into the dialysis bath will occur. This method can be used to successfully lower the concentration in blood of urea and in plasma of potassium. Net removal of substances whose concentrations should not be altered in blood or plasma, such as sodium in the latter, can be removed by establishing a hydrostatic pressure gradient across the membrane, creating a convective pathway for movement of solutes across the membrane.

The invention consists of a device and method for using it to purify (i.e., detoxify) a biological fluid such as blood or plasma, whereby blood or separated plasma is circulated through a bioreactor having at least one semi-permeable membrane passing therethrough. The semipermeable membranes may be in tube, film or hollow fiber form (preferably the latter), and are surrounded by a sterile cell culture medium in solution for maintenance of hepatocytes and/or a hepatoma cell line (as explained further below, the term "hepatocyte" will, unless context otherwise requires, refer both to isolated hepatic cells and a combination of those cells which Kupffer bile duct epithelial and endothelial cells and, in some instances, fibroblasts). Soluble proteins, glucose and toxins in the blood or plasma diffuse across the membrane into the culture medium for metabolism by the hepatocytes.

Additional purification means such as a hemofiltration device, means for adsorption onto an activated charcoal column or other resin adsorbents and/or a conventional dialysis device may also be provided as needed to remove certain toxic drug or waste products not broken down or stored by the hepatocytes (such as urea excreted thereby into the culture medium). Means may also be provided in the device to remove any antibodies formed to the hepatocytes or, for example, to xenogeneic grafts of liver tissue in transplant patients not captured by the hepatocytes.

Figure 8:
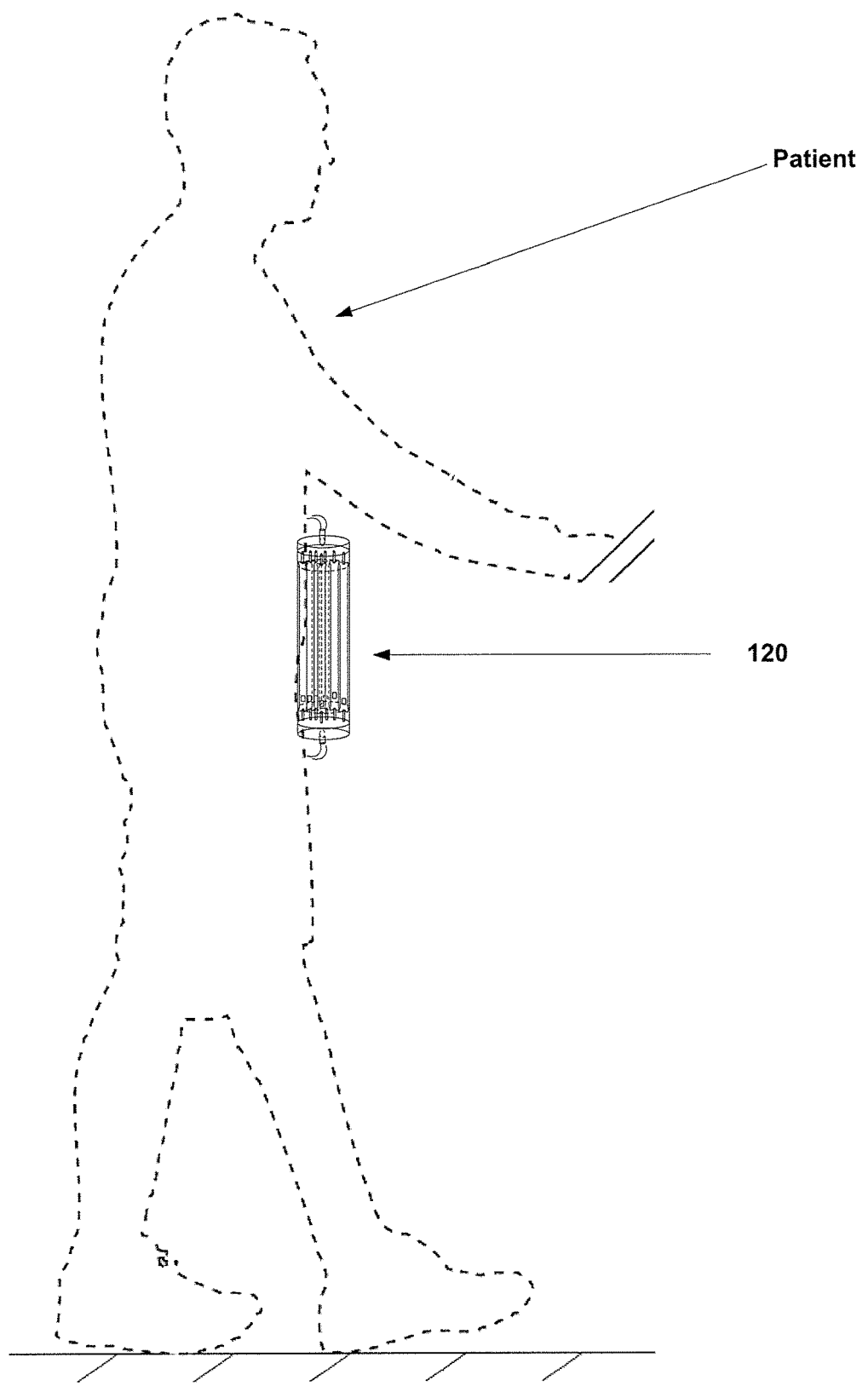
FIG. 8 is a functional diagram showing how the bio-artificial liver device may be worn by the patient.

The specification discloses a liver scaffold culture system which may be, for example, an early stage testing tool for drug companies to use before investing time and money in in vivo models. Once the drug company has gone through its initial "hit-to-lead" high-throughput screening, the living human hepatic tissue could be utilized to speed up the development of candidate compounds, allowing the company to examine the tissue using a variety of assays, such as histological, immune-histological and molecular markers. Unlike other recent technologies that are being evaluated, such as 3D tissue printing, the scaffolds as disclosed herein hold key components necessary to fully mimic hepatic tissue. Three-dimensional bioprinted tissue can be a powerful tool for making headway in areas where traditional animal models and 2D cell-culture methods aren't able to meet. However, the system as disclosed herein allows pharma to go beyond bio-printing technology, giving them more and better avenues to filter and reject an ineffective or dangerous drug in a matter of weeks to months. This will shorten the drug discovery process—which can take up to six years—and results in significant savings. Embodiments of the present disclosure include but are not limited to the following elements:

1) A fully functional 3D liver culture system which may be used, for example, for active compound screening in liver drug discovery.
2) A fully functional extracorporeal liver assist device 120 (see FIG. 8) for the treatment of patients in liver failure to bridge them to a whole organ transplant of allow their own liver to recover or in the treatment of chronic diseases.
3) An implantable, transplantable, personalized bio-liver, alleviating the excessive wait time for patients on the liver transplant list.
4) An implantable, transplantable, personalized bio-pancreatic islet with insulin production for treatment of type 1 diabetes.

Modularization

Figure 5A:
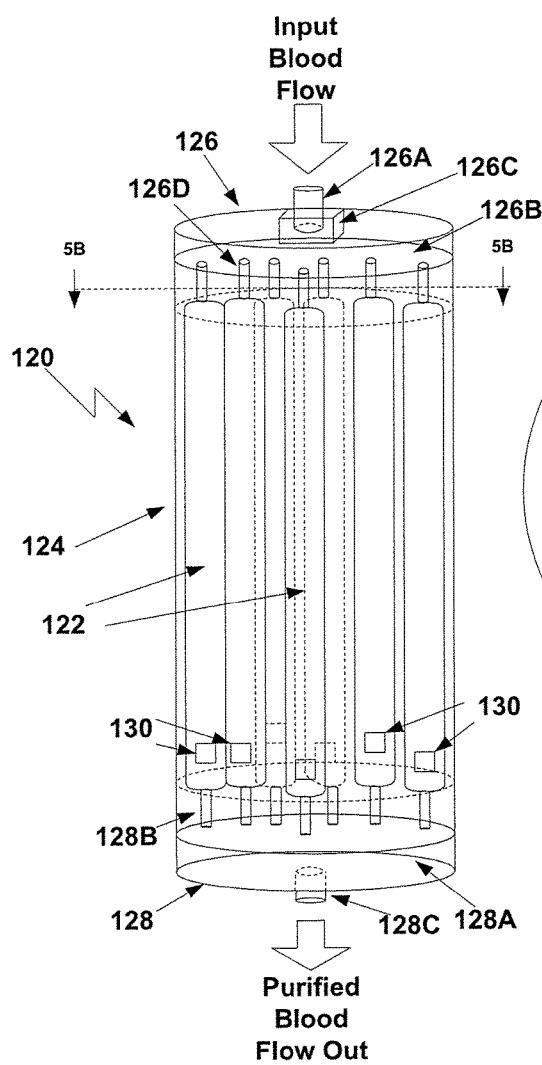
FIG. 5A is a functional diagram of a bio-artificial liver device comprising a plurality of columns for filtering a blood flow input.
Figure 5B:
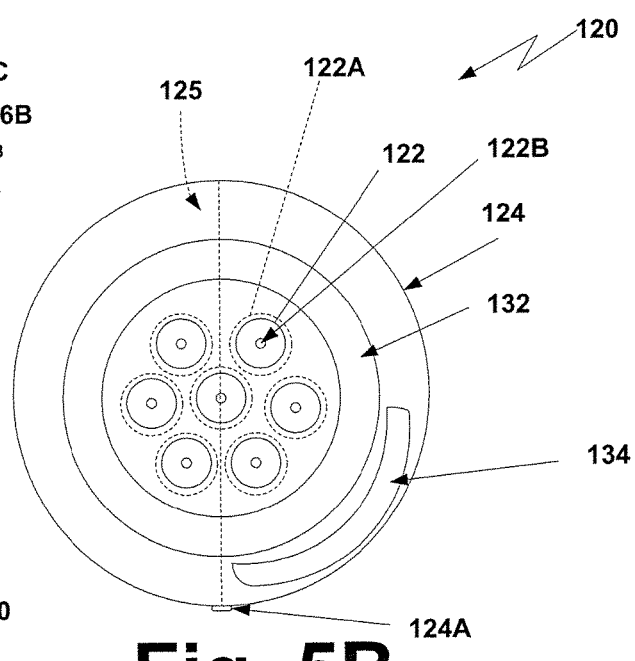
FIG. 5B is a top view of the device of FIG. 5A taken along line 5B-5B of FIG. 5A.
Figure 5C:
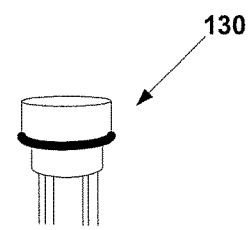
FIG. 5C is a side view of a sensor positioned in the lower portion of each column.
Figure 6:
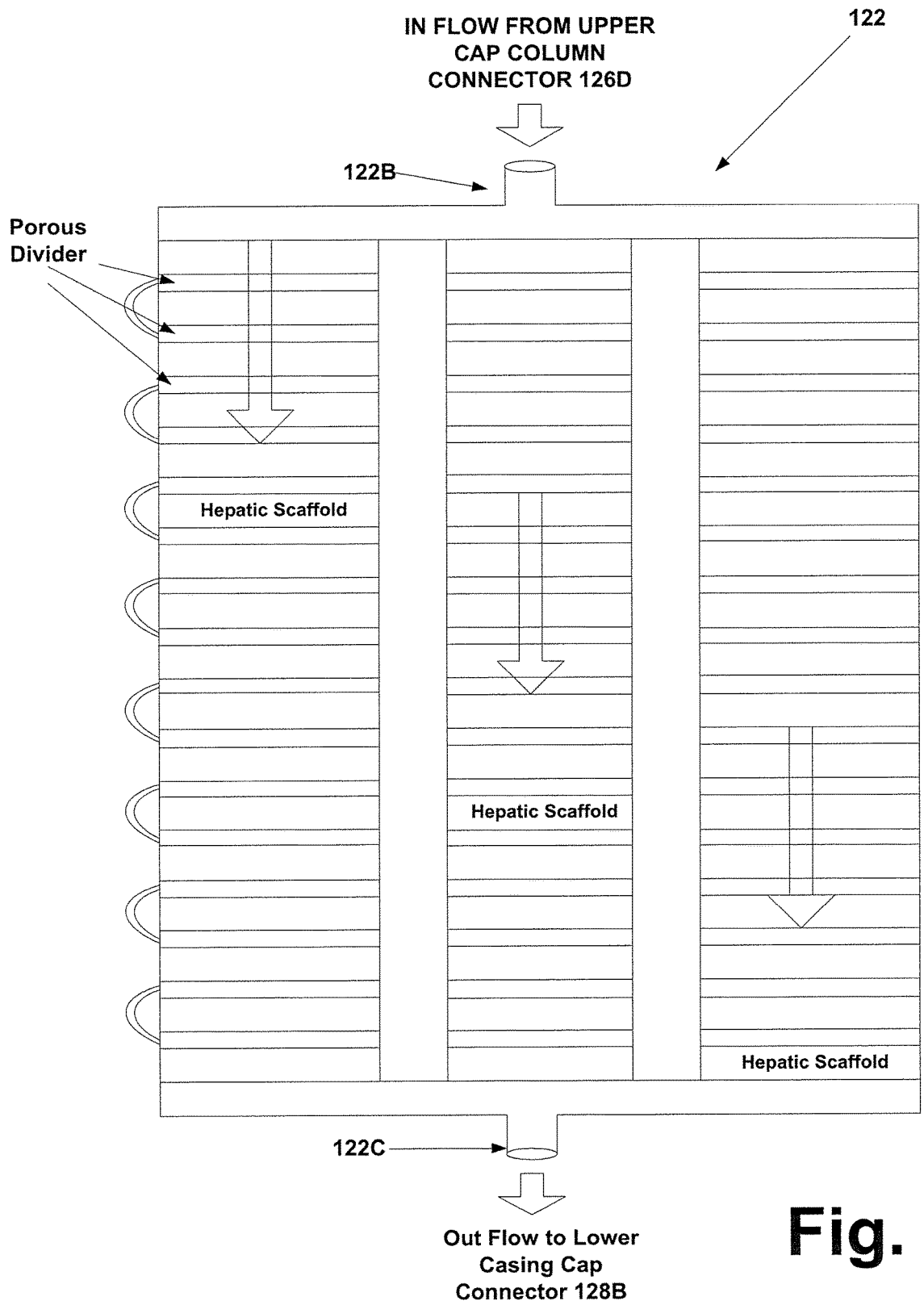
FIG. 6 is a functional diagram of one column of the bio-artificial liver device of FIG. 5A.
Figure 7:
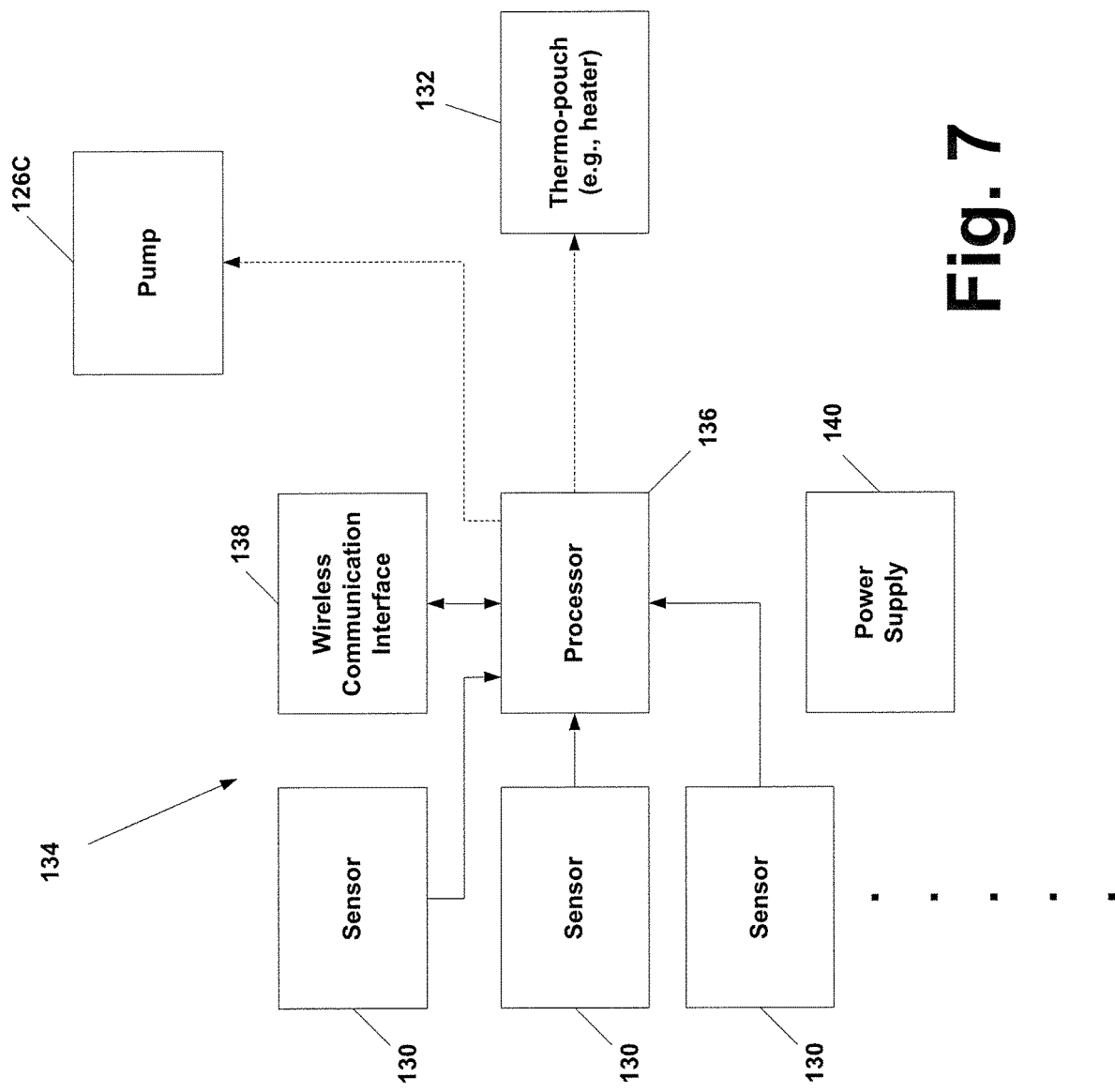
FIG. 7 is a block diagram of the components of the electrical suite portion of the bio-artificial liver device.

Exemplary embodiments are shown in FIGS. 5A-C and 6-8 though size and configuration may be more compact and smaller in production. The present disclosure focuses on modular components for use in an artificial organ, such as a liver or pancreas 120. In exemplary embodiments, the components may consist of:

1. Individual columns 122 containing decellularized, devitalized excellular matrix derived from neonate porcine liver or pancreas. (see FIGS. 5A-5B and 6)
2. a living cellular component of human hepatocytes or pancreatic islet beta cells derived from fetal or neonatal human liver or pancreas, pediatric, teenage or adult human liver or pancreas, cultured human hepatocytes or beta cells, stem cell derived hepatocytes or beta cells. As used herein, the term "hepatocyte" should be understood to encompass hepatic cells or fibroblasts alone or in combination with Kupffer cells, bile duct epithelial and endothelial cells. It may also be desirable to utilize cells which have been genetically altered to produce or metabolize liver specific products such as albumin or clotting factors. These cells could be used exclusively or in a cocktail with native hepatocytes.
3. Stem cell derived hepatocytes or beta cells may be derived from differentiation in vivo or ex vivo of embryonic, fetal, neonatal, pediatric or adult hepatobiliary or pancreatic stem cells, from embryonic, fetal, neonatal, pediatric or adult hematopoietic stem cells, from embryonic, fetal, neonatal, pediatric or adult mesenchymal stem cells, from undifferentiated embryonic stem cells, or from induced pluripotent stem cells.
4. The individual columns 122 are positioned within a casing 124 in respective holding devices 122A. The casing 124 may comprise two shells that are hinged together (via hinge 124A) which allows access to the individual columns 122 and then closed for use, as indicated by the closure line 125 (FIG. 5B). By way of example only, the column length may comprise approximately 7 inches and the overall length of the casing 124 may comprise 8 inches. Each column 122 comprises a cellularized scaffolds plasma flow. It should be noted that the number of columns 122 depicted in the device 120, namely, seven, is by way of example only is not in any way limited to that number.
5. As mentioned previously, each column 122 may be placed in a holding device 122A that is positioned within the casing 124. The holding device 122A may comprise a sleeve that allows for a friction-fit of the respective column 122 therein, thereby allowing the respective column 122 to be easily inserted or removed from the casing 124 while precisely positioning the upper and lower ends of the column 122 to align with a respective connector 126D in an upper casing cap 126 and a respective connector 128B in a lower casing cap 128 (FIG. 5A).
6. The upper casing cap 126 comprises a port 126A for receiving the input blood flow therein. The port 126A leads to a distribution chamber 126B in which a pump 126C is positioned for slightly pressurizing the input blood flow prior to entering the respective columns 122 via respective connectors 126D leading to corresponding ports 122B in each column 122. Similarly, the lower casing cap 128 comprises a collection chamber 128A for receiving the purified blood from the base of each column 122 via lower column connectors 122C (FIG. 6) with respective lower cap connectors 128B that are in fluid communication with the collection chamber 128A. An exit port 128C provides the output of the purified blood flow to the patient.
7. The columns 122 are independent from each other and each column will have sensors (for example, Bluetooth capable; see FIGS. 5A and 5C)) at the end of each column so each column can be monitored for metabolic and functional activity. This monitoring will allow for assessment of each column 122 to replace if necessary.
8. The bio-artificial liver device 120 will need to hold approximately 500-700 grams of cellularized tissue in order to provide sufficient tissue to function to keep the body in homeostasis.
9. In addition, in exemplary embodiments, the device 120 may comprise a thermo-pouch 132 that surrounds the plurality of columns (see FIG. 5B) in order to help maintain optimal temperature for the cells within the device 120. By way of example only, the thermo-pouch 132 may comprise a heater with heat conductive sheet/layer.
10. In exemplary embodiments, the function of the bio-artificial liver or pancreas may be controlled by dedicated sensors, micro-controllers, wireless communication systems, micro-actuators and contactless identification tags (e.g., for identifying individual columns 122). By way of example only, the micro-controllers (e.g., a processor) and wireless communication system/interface, etc. may reside in an electronics suite 134 located between the thermo-pouch 132 and the outer wall of the casing 124. FIG. 7 comprises a block diagram of the contents of the electronic suite 134, showing a processor 136 that receives sensor inputs from sensors 130 while also controlling the pump 126C and the thermo-pouch 132. The processor 136 also communicates remotely via a wireless communication interface 138 (e.g., Bluetooth Smart/BLE module, etc.). The electronics are powered by an independent redundant battery power system 140.
11. In exemplary embodiments, the bio-artificial liver or pancreas contains an independent redundant battery power system, a hydraulic system and a thermal control system
12. In exemplary embodiments, sensors can be used to monitor the blood values before and after the columns including but not limited to glucose levels, electrolytes (e.g. sodium, potassium, chloride, and bicarbonate), pH, oxygenation level, ammonia level, lipid levels, the speed and cumulative volume of flow of the blood, temperature, blood pressure.
13. In exemplary embodiments, sensors can be used to monitor blood values such as hematocrit, iron saturation concentration, red blood cell balance.
14. In exemplary embodiments, sensors can alert clinical staff overseeing the use of the devices for deviations from normal that may require adjustment of the device or additional diagnostics or therapeutic adjustments for the patient.
15. In exemplary embodiments, sensors can detect potential or known and identified toxins (e.g. prescription or over the counter medications, herbal remedies, dietary supplements, ingested, topical or environmental toxins, bio-threats, chemical weapon threats).
16. In exemplary embodiments, sensors can detect infectious agents (e.g. bacterial, viral, fungal, and parasitic)
17. In exemplary embodiments, sensors can detect molecular or cellular breakdown products of infectious agents (e.g. endotoxins, organism membrane fragments, and membrane associated vesicles)
18. In exemplary embodiments, sensors can be used to monitor quality of flow in and out of the bio-artificial liver or pancreas, signal presence of toxins or infectious agents, both for contamination or for monitoring elimination though the device if the toxins or infections agents are known before administration of the device.
19. In exemplary embodiments, the micro-controller may supervise all the functionality, communicate the status and results of sensor measurements with a cloud based health monitoring system through a wireless connection, receive new/adjusted functional parameters to better adapt to the ongoing treatment.
20. In exemplary embodiments, the communication may be encrypted and data available only to the entitled entities.
21. In exemplary embodiments, the system might include a local user interface and/or a remote user interface, accessible through the wireless connection.
22. In exemplary embodiments, the contactless identification tab together with the micro controller and wireless communication enable the complete traceability as well as ensuring that only columns intended for the specific patient are used. They also include sensors and real time clock to ensure that the column was stored in appropriate conditions and the shelf life is respected.
23. In exemplary embodiments, the micro-actuators together with the hydraulic system insure the control of the blood flow. They also enable a column exchange without blood loss. They are also used for precisely flushing the column with isotonic solution before a column exchange in order to minimize the blood loss.
24. In exemplary embodiments, the thermal system keeps the bio-artificial liver at a constant temperature.
25. In exemplary embodiments, the redundant battery system powers all the functionality mentioned above and includes self-diagnosis, overheating and overcurrent protections.
26. In exemplary embodiments, the device will be simple in nature, with a central blood line out and a central blood line in.
27. In exemplary embodiments, blood flow can be either arterial derived or venous derived or can come from an implanted or surgically created fistula.
28. In exemplary embodiments, venous blood flow will be propelled by gravitational force and low pressure of the venous system; arterial blood flow will be propelled through arterial blood pressure with or without gravitational force.

Columns

In exemplary embodiments, columns will be packed with recellularized scaffolds as well polycarbonate spacers between scaffolds.

In exemplary embodiments, these scaffolds are of natural material derived from decellularized animal livers or pancreas.

In exemplary embodiments, animals would be mammals (including, but not limited to pigs, dogs, cats, sheep, and goats).

In exemplary embodiments, the column(s) will develop as separable and interchangeable cartridges in such a way that the column can be separated from the blood flow and then taken out and replaced with a new column and placed back into the blood flow without highly skilled medical training.

In exemplary embodiments, columns may connect to a manifold in such a way that the blood can only flow down the columns and will empty into a reservoir where it will back into the body.

Mobility

In exemplary embodiments, the device may give the patient freedom to move out of the hospital room. The process is simple in nature, unlike dialysis for the kidney, where the patient is tethered to a machine to clean the patient's blood, the bio-artificial liver device will act as dialysis for the liver or artificial insulin-producing islets for diabetics or cells productive of any other pancreas derived proteins such as hormones or enzymes. The device will be in a harness that the patient can easily slip on holding it close to the body (Figure ###). This gives the patient the ability to walk out of the hospital with a device that is, for example, Bluetooth connected giving the physician the ability to monitor the patient's health even if the patient was hundreds of miles away, as long as there is an internet or cell phone connection.

Sensors

The device as disclosed herein may be configured to receive one or more signals from one or more sensors. For example, where the one or more sensors are configured to emit an electromagnetic signal following detection of a condition of the device, the programmable microprocessor can include an EM signal detection device, such as a detection device configured to detect non-visible light or light of a specific wavelength.

In embodiments in which the one or more sensors are configured to emit optically detectable signals, the one or more sensors can include, in part or in whole, an optically permeable section (e.g. a window), and the one or more sensors or the programmable microprocessor can include, in part, a spectrophotometer and/or light source configured to elicit signals related to information regarding a physiological condition of the subject.

For example, the one or more sensors of the device as disclosed herein can include at least one of a chromogen, fluorescent agent, luminescent agent, a quantum dot, or a compound configured to exhibit alterable optical density. A light source associated with the one or more sensors can include, for example, a light emitting diode or a white light source, such as a source configured to provide light in a variable and/or specific wavelength, including infrared (IR) or ultraviolet (UV). See, for example, U.S. Pat. No. 5,183,740 to Ligler et al., titled "Flow immunosensor method and apparatus," U.S. Pat. No. 7,459,713 to Coates, titled "Integrated handheld sensing system approach for handheld spectral measurements having a disposable sample handling apparatus," U.S. Patent Application No. 2008/0265146 to Coates, titled "Integrated sensing module for handheld spectral measurements," which are herein incorporated by reference. For example, a sensor pair consisting of a light emitter and a light detector can be configured to be a part of the one or more sensors. The electronics module sensor can include a digital signal processor and/or software for converting the light signal into information able to be stored or communicated between the digital processing unit, programmable microprocessor, and sensors. See, for example: U.S. Pat. No. 6,623,698 to Kuo, titled "Saliva-monitoring biosensor head toothbrush;" U.S. Pat. No. 7,314,453 to Kuo, titled "Handheld diagnostic device with renewable biosensor;" U.S. Patent Application No. 2003/0023189 to Kuo, titled "Handheld diagnostic device with renewable biosensor;" and U.S. Patent Application No. 2002/0127143 to Kuo, titled "Saliva-monitoring biosensor electrical toothbrush," which are herein incorporated by reference. In some embodiments, the one or more sensors can use electric pulses to measure the conductivity of one or more tissues of the subject to measure a physiological condition of the subject, e.g., pH, pCO.sub.2, blood flow, blood pressure, skin temperature, core temperature, tissue temperature, or blood oxygenation. See, for example, U.S. Pat. Nos. 6,623,698 and 7,314,453 to Kuo.

The device as disclosed herein may comprise one or more sensors that can be operably connected to the electronics module. The electronics module can be operably connected to the programmable microprocessor and can be configured to receive information from the sensor, to process the information into at least one resulting instruction, and to provide the at least one resulting instruction to the programmable microprocessor. The one or more indicator of the one or more physiological conditions can include a plasma and/or localized tissue level of one or more analytes, e.g. a metabolic analyte, in the blood of the subject. In an aspect, the one or more analytes can include analytes associated with a disorder. In an aspect, the one or more metabolic analytes can include metabolic analytes associated with a metabolic disorder. The one or more metabolic analytes indicative of a metabolic disorder include, but are not limited to, glucose, free fatty acids, triglycerides, insulin, glucagon, pro-inflammatory molecules, cholesterol, low density lipoprotein (LDL), and high-density lipoprotein (HDL).

In an aspect, the one or more analytes can include, but are not limited to, utilizable glucose, produced and/or released glycerol, free fatty acids, cAMP (indicative of beta-adrenergic receptor stimulation), hexokinase and phosphofructokinase or their enzymatic activities or products.

The device can include one or more sensors configured to sense one or more other physiological conditions of the subject including, but not limited to, pH, pCO2, blood flow, blood pressure, skin temperature, core temperature, tissue temperature, or blood oxygenation. The one or more sensors can also be configured to sense measures of physical activity of the subject as a means for estimating daily energy expenditure. Measures of physical activity of a subject include, but are not limited to, body temperature, heart rate, skin resistance, motion/acceleration, and velocity.

The one or more sensors operably connected with an electronics module and/or programmable microprocessor can include but are not limited to one or more biosensors, chemical sensors, pressure sensors, temperature sensors, flow sensors, viscosity sensors, shear sensors (e.g., for measuring the effective shear modulus of the fluid at a frequency or strain-rate), pH sensors, optical sensors (e.g., charged couple device (CCD) array), optical waveguide sensors, acoustic sensors, surface acoustic wave sensors, quartz microbalance sensors, metal oxide sensors, bulk acoustic wave sensors, plate acoustic wave sensors, electrical sensors, magnetic sensors, interdigitated microelectrode sensors, electrochemical sensors, electrically conducting sensors, artificial noses, electronic noses, electronic tongues, semiconductive gas sensors, mass spectrometers, near infrared and infrared spectrometers, ultraviolet sensors, visible light-based sensors, fluorescence spectrophotometers, conductive-polymers, gas-fluorescence spectrophotometers, impedance spectrometers, aptamer-based biosensors, ion mobility spectrometry, photo-ionization detectors, amplifying fluorescent polymer sensors, ion mobility spectrometry, electrical impedance, microgravimetric sensors, cantilever and microcantilever sensors, accelerometers, global positioning devices, clocks or time-keeping devices. See, e.g., U.S. Pat. Nos. 5,522,394; 5,873,835; 6,409,674; 6,111,520; 6,278,379; 6,475,639; 6,802,811; 6,855,115, 6,517,482; 6,675,030; 6,836,678; 6,954,662; 7,184,810; 7,299,080, and U.S. Patent Application 2005/0277839, each of which is incorporated herein by reference.

The one or more sensors can include a single sensor or an array of sensors, and is not limited to a particular number or type of sensors. The one or more sensors can be very small, comprising a sensor or array of sensors, having, for example, a biosensor, a chemical sensor (Snow Science, 2005, 307: 1942-1945), a gas sensor (Hagleitner et al., Nature, 2001 414:293-296), an electronic nose, a nuclear magnetic resonance imager (Yusa et al., Nature, 2005, 343:1001-1005). The foregoing references are each incorporated herein by reference. Further examples of sensors are provided in The Biomedical Engineering Handbook, Second Edition, Volume I, J. D. Bronzino, Ed., Copyright 2000, CRC Press LLC, pp. V-1-51-9; Morrison et al., "Clinical Applications of Micro- and Nanoscale Biosensors" in Biomedical Nanostructures. Edited by K. E. Gonsalves, C. L. Laurencin, C. R. Halberstadt, L. S, Nair. 2008, John Wiley & Sons, Inc.; and U.S. Pat. No. 6,802,811, each of which is incorporated herein by reference.

The one or more sensors can be configured to detect an analyte that includes, but is not limited to, a biological marker, an antibody, an antigen, a peptide, a polypeptide, a neuropeptide, a protein, a complex, an enzyme, a hormone, a neurotransmitter, a nucleic acid, a cell (and, in some cases, a cell of a particular type, e.g. by methods used in flow cytometry), a cell fragment, a cellular component, a platelet, an organelle, a gamete, a pathogen, a lipid, a lipoprotein, an alcohol, an acid, an ion, an immunomodulator, a sterol, a carbohydrate, a saccharide, a polysaccharide, a glycoprotein, a metal, an electrolyte, a metabolite, an organic compound, an organophosphate, a drug, a therapeutic, a gas, a pollutant, or a tag. The one or more sensors can include one or more binding elements configured to interact with an analyte including, but not limited to, binding molecules, recognition elements, antibodies or fragments thereof, oligonucleotide or peptide based aptamers (see, e.g., Mok & Li Sensors 8: 7050-7084, 2008, which is incorporated herein by reference), receptors or ligands, artificial binding substrates (e.g. those formed by molecular imprinting), or any other examples of molecules and/or substrates capable of interacting with an analyte.

In an aspect, the device including the one or more sensors can include one or more optical sensors. An optical sensor can be configured to measure the optical absorption, optical emission, fluorescence, or phosphorescence, luminescence of an analyte or an associated tag or binding element, other tissues of interest, or combinations thereof. Such optical properties can be inherent optical properties of the analyte, e.g. autofluorescence, or can be optical properties of materials added or introduced into the body of the subject that interact with the analyte, other tissues of interest, or combinations thereof. Optical sensing of materials in blood, for example, is described in Mattley et al., "Blood characterization using UV/VIS spectroscopy" Proc. SPIE Advances in Fluorescence Sensing Technology II, Joseph R. Lakowicz; Ed. Vol. 2388, p. 462-470, 1995 and U.S. Pat. Nos. 5,589,932 and 7,027,134, each of which is incorporated herein by reference.

The ingestible drug delivery devices may include one or more sensors configured to sense the blood glucose levels in the subject. The one or more sensors can include a glucose sensor that is either an integral part of the device, wherein the sensors is operably connected to the programmable microprocessor as described herein, or is in a separate device, for example a glucose sensing device in wireless communication with the programmable microprocessor in the device described herein. A number of different glucose monitors have been described using, for example, pin prick, transdermal, or implantable devices. See, e.g., U.S. Pat. Nos. 4,436,094; 4,953,552; 5,497,772; U.S. Patent Applications 2010/0049021; 2010/0081910; each of which is incorporated herein by reference. The one or more sensors can include one or more electrochemical- or photochemical-based sensors wherein a measurable chemical reaction occurs in response to the presence of one or more analyte. For example, many electrochemical sensors use enzymes as specifiers for the analyte. The enzymes cause a chemical reaction, such as a reduction reaction, and electrons released by the reaction are transferred to a mediator molecule, which itself is converted. The mediator then transfers the electrons to an electrode for electrochemical measurement or transfers the electrons to an indicator molecule for photochemical responses. Ferrocene derivatives and hexacyanoferrate are examples of one-electron mediators. Quinones are an example of two-electron mediators. A glucose sensor included in the device uses as the specifier an oxidoreductase that oxidizes glucose to gluconolactone. Electrons from the glucose are then transferred to the oxidized form of a mediator molecule, which in turn delivers the electrons to an electrode. The amount of electric current generated is proportional to the amount of glucose in the sample, and electronics within the sensor convert the signal, and the signal is communicated to the programmable microprocessor or the electronics module that is operably connected to the programmable microprocessor. See, e.g., Hones, et al., Diabetes Techn & Therap, 10: Supplement 1 S10-S26, 2008. Examples of commercially available glucose monitors using such technology in measuring blood glucose levels of a subject include, but are not limited to, OneTouch® blood glucose monitors (LifeScan-Johnson & Johnson, Milpitas, Calif.), Accu-Chek® blood glucose monitors (F. Hoffman-Roche A G, Basel, Switzerland), and Ascencia® blood glucose monitors (Bayer HealthCare LLC, Tarrytown, N.Y.). In an aspect, the glucose sensor for measuring blood glucose levels of a subject can include a continuous monitoring system, examples of which include, but are not limited to Freestyle. Navigator® glucose monitor (Abbot Diabetes Care, Alameda, Calif.), Guardian® Real-Time glucose monitor (Medtronic MiniMed, Northridge, Calif.), and DexCom® SEVEN® glucose monitor (Dex-Com, San Diego, Calif.). See, e.g., Hermanides & DeVries, Diabetologia, 53: 593-596, 2010, which is incorporated herein by reference. The FreeStyle Navigator® glucose monitor, for example, is a biocompatible chip implanted into the abdomen or back of the upper arm of a subject and includes an external receiver. Similarly, blood glucose sensor-enabled radio frequency identification (RFID) devices have been described for active monitoring of glucose. See, e.g., Moore, J. Diabetes Sci. Technol. 3: 180-183, 2009, which is incorporated herein by reference. Miniaturized (0.5.times.0.5.times.5 mm) implantable glucose sensors can include the GLUCOWIZZARD® implantable glucose sensor that senses glucose levels and transmits the information to a proximal communicator. See, e.g., BIORASIS Storrs/Mansfield, Conn. A bio-sensor chip can include a passive transponder, glucose sensor, and integrated circuitry. See, e.g., U.S. Pat. No. 7,125,382 to Zhou entitled "Embedded Bio-sensor System," which is incorporated herein by reference. See, e.g., Digital Angel Corporation, St. Paul, Minn. Other methods for continuous monitoring of blood glucose levels of a subject include transcutaneous fluorescence lifetime-based microsensors or subcutaneous microelectromechanical systems (MEMS)-based sensors. See, e.g., U.S. Pat. No. 6,304,766; Nielsen, et al., J. Diabetes Sci. Technol. 3: 98-109; Li, et al., J. Diabetes Sci. Technol. 2: 1066-1074, 2008, each of which is incorporated herein by reference.

In an aspect, the one or more sensors can use a charged coupled device (CCD) or complementary metal-oxide-semiconductor (CMOS) sensor, for example, in combination with a binding element that exhibits altered optical properties, e.g., fluorescence, in response to binding an analyte. For example, glycerol and/or free fatty acids can be analyzed using one or more of the sensors. A sensor for measuring a free fatty acid can include an acyl-CoA-binding protein which exhibits an increased fluorescence yield in response to binding a fatty acid. See, e.g., Wadum, et al., Biochem. J., 365: 165-172, 2002, which is incorporated herein by reference.

In an aspect, the one or more sensor can include a binding element, e.g., an antibody or oligonucleotide aptamer, configured to exhibit Forster or fluorescence resonance energy transfer (FRET) in response to binding one or more analytes in the subject. FRET is a distance-dependent interaction between the excited states of two fluorophore molecules in which excitation is transferred from a donor molecule to an acceptor molecule without emission of a photon. For use in a sensor, one or more binding molecules, e.g., antibodies or oligonucleotide aptamers, associated with the one or more sensors are configured with at least one donor molecule and at least one acceptor molecule. The interaction of an analyte with the binding molecule of the sensor results in a conformation change in the binding molecule, leading to changes in the distance between the donor and acceptor molecules and changes in measurable fluorescence.

Donor and acceptor fluorophore pairs can be considered for FRET including, but not limited to, fluorescein and tetramethylrhodamine; IAEDANS and fluorescein; fluorescein and fluorescein; and BODIPY FL and BODIPY FL, and various Alexa Fluor pairings as described herein. The cyanine dyes Cy3, Cy5, Cy5.5 and Cy7, which emit in the red and far red wavelength range (>550 nm) as well as semiconductor quantum dots can also be used for FRET-based detection systems. Quenching dyes can also be used to quench the fluorescence of visible light-excited fluorophores, examples of which include DABCYL, the non-fluorescing diary rhodamine derivative dyes QSY 7, QSY 9 and QSY 21 (Molecular Probes, Carlsbad, Calif., USA), the non-fluorescing Black Hole Quenchers BHQ0, BHQ1, BHQ2, and BHQ3 (Biosearch Technologies, Inc., Novato, Calif., USA) and Eclipse (Applera Corp., Norwalk, Conn., USA). A variety of donor fluorophore and quencher pairs can be considered for FRET associated with the binding molecule including, but not limited to, fluorescein with DABCYL; EDANS with DABCYL; or fluorescein with QSY 7 and QSY 9. In general, QSY 7 and QSY 9 dyes efficiently quench the fluorescence emission of donor dyes including blue-fluorescent coumarins, green- or orange-fluorescent dyes, and conjugates of the Texas Red and Alexa Fluor 594 dyes. QSY 21 dye efficiently quenches all red-fluorescent dyes. A number of the Alexa Fluor (AF) fluorophores (Molecular Probes-Invitrogen, Carlsbad, Calif., USA) can be paired with quenching molecules as follows: AF 350 with QSY 35 or DABCYL; AF 488 with QSY 35, DABCYL, QSY7 or QSY9; AF 546 with QSY 35, DABCYL, QSY7 or QSY9; AF 555 with QSY7 or QSY9; AF 568 with QSY7, QSY9 or QSY21; AF 594 with QSY21; and AF 647 with QSY 21.

The one or more sensors for sensing one or more physiological conditions in the device as disclosed herein, or in certain embodiments of a subject can include surface plasmon resonance (for planar surfaces) or localized surface plasmon resonance (for nanoparticles). Surface plasmon resonance involves detecting changes in the refractive index on a sensor surface in response to changes in molecules bound to the sensor surface. In an aspect, the surface of the sensor is a solid support coated with a thin film of metal, e.g., gold. The one or more sensors include a matrix to which is immobilized one or more binding molecules, e.g., antibodies or aptamers, that recognize one or more analytes. The sensor is illuminated by monochromatic light. Resonance occurs at a specific angle of incident light. The resonance angle depends on the refractive index in the vicinity of the surface, which is dependent upon the concentration of analyte bound to the surface. See, e.g., Raghavan & Bjorkman Structure 3: 331-333, 1995, which is incorporated herein by reference.

The one or more sensors for sensing analytes can be one or more label-free optical biosensors that incorporate other optical methodologies, e.g., interferometers, waveguides, fiber gratings, ring resonators, and photonic crystals. See, e.g., Fan et al., Anal. Chim Acta 620: 8-26, 2008, which is incorporated herein by reference. The light-based signal or electrical signal to the sensor is converted by a transducer, e.g., within the digital processing unit, into within the digital processing unit, which then processes the data into information that can be stored, analyzed, and communicated, including, for example, at least one resulting instruction. The electronics module provides the at least one resulting instruction to the programmable microprocessor.

The one or more sensors configured to provide information regarding one or more physiological conditions of the subject can include one or more microcantilevers. A microcantilever can act as a biological sensor by detecting changes in cantilever bending or vibrational frequency in response to binding of one or more analytes to the surface of the sensor. See, e.g., Lavrik et al., Rev. Sci. Inst, 75:4: 2229-2253, 2004, which is incorporated herein by reference. In an aspect, the sensor can include a microcantilever or a microbead as in an immunoaffinity binding array. In another aspect, a biochip can be formed that uses microcantilever bi-material, e.g., formed from gold and silicon, as sensing elements. See, e.g. Vashist J. Nanotech Online 3: DO: 10.2240/azojono0115, 2007, which is incorporated herein by reference. The gold component of the microcantilever can be coated with one or more binding molecules which upon binding one or more analytes causes the microcantilever to deflect. Aptamers or antibodies specific for one or more analytes can be used to coat microcantilevers. See, e.g., U.S. Pat. No. 7,097,662, which is incorporated herein by reference. The one or more sensors can incorporate one or more methods for microcantilever deflection detection including, but not limited to, piezoresistive deflection, optical deflection, capacitive deflection, interferometry deflection, optical diffraction grating deflection, and charge coupled device. The deflection is measured and transmitted as data by a transducer, e.g., within the digital processing unit, which then processes the data into information that can be stored, analyzed, and communicated, including, for example, at least one resulting instruction. The electronics module provides the at least one resulting instruction to the programmable microprocessor. In some aspects, the one or more microcantilevers can be a nanocantilever with nanoscale components. The one or more microcantilevers and/or nanocantilevers can be arranged into arrays. Both microcantilevers and nanocantilevers can find utility in microelectromechnical systems (MEMS) and/or nanoelectromechnical systems (NEMS).

The one or more sensors for sensing analytes can include a field effect transistor (FET) based biosensor. In this aspect, interaction of one or more analytes with one or more binding elements of the sensor induces an electrical change that is detected by the transistor. See, e.g., U.S. Pat. No. 7,303,875, which is incorporated herein by reference. The signal is processed by the electronics module into at least one resulting instruction. The electronics module provides the at least one resulting instruction to the programmable microprocessor.

The one or more sensors for sensing one or more analytes can incorporate electrochemical impedance spectroscopy. Electrochemical impedance spectroscopy can be used to measure impedance across a natural and/or artificial lipid bilayer. The sensor can incorporate an artificial bilayer that is tethered to the surface of a solid electrode. One or more receptor can be embedded into the lipid bilayer. The one or more receptors can be ion channels that open and close in response to binding of a specific analyte. The open and closed states can be quantitatively measured as changes in impedance across the lipid bilayer. The changes in impedance are measured and transmitted as data by a transducer. See, e.g., Yang, et al., IEEE SENSORS 2006, EXCO, Daegu, Korea/Oct. 22-25, 2006, which is incorporated herein by reference. The signal is processed by the electronics module into at least one resulting instruction. The electronics module provides the at least one resulting instruction to the programmable microprocessor.

The one or more sensors can include cells with binding molecules that induce a measurable or detectable change in the cells, e.g., a luminescent signal, when bound to analytes. For example, one can use a bioluminescent bioreporter integrated circuit in which binding of an analyte to an engineered cell induces expression of a reporter polypeptide linked to a luminescent response. See, e.g., U.S. Pat. No. 6,673,596; Durick & Negulescu Biosens. Bioelectron. 16: 587-592, 2001, each of which is incorporated herein by reference. Alternatively, the one or more cell can be engineered to emit an electrical signal in response to interacting with one or more analytes. In a further aspect, an implantable biosensor can include genetically modified cells that respond to binding analytes by emitting a measurable electrical signal in response to one or more intracellular second messenger molecules that in turn modulate the activity of one or more ion channels in the genetically modified cells. The genetically modified cells act as an implantable biosensor that can be coupled via an electrical or optical interface to an electronics module that processes the signal into at least one resulting instruction and provides the at least one resulting instruction to a programmable microprocessor. See U.S. Patent Application 2006/0234369 A1; which is incorporated herein by reference. In another aspect, a biosensor can include a microbial biosensor. For example, a microbial biosensor and an oxygen electrode can be used to sense free fatty acid. See, e.g., Schmidt, et al., Biosensors Bioelectronics 11: 1139-1145, 1996, which is incorporated herein by reference.

The one or more sensors can be configured to include an assembly for in vivo microdialysis. In vivo microdialysis allows for continuous sampling from the interstitial fluid of a tissue with minimal influence on surrounding tissues and/or whole body function. A microdialysis probe can be inserted into a tissue of interest, and perfused at a constant flow rate with a physiological buffer, e.g., saline. The tip of the probe consists of a semi-permeable membrane through which compounds in the interstitial fluid of the tissue can diffuse and subsequently be sampled from the outlet tubing of the probe.

The one or more sensors can include one or more temperature sensors configured to measure temperature in one or more tissues. The temperature sensor can be a thermistor, a thermocouple, or a resistive temperature detector. In an aspect, the temperature sensor is an integral component of a self-contained, fully ingestible device.

The one or more sensors can include one or more sensors that are calorimeters configured to measure caloric intake and/or energy expenditure. In an aspect, the one or more calorimeter can include an indirect calorimeter configured to assess the physical activity of the subject by periodically monitoring heart rate, body temperature, skin resistance, motion/acceleration sensing, velocity and providing an estimate of caloric intake/energy expenditure. The indirect calorimeter can include one or more of a temperature sensor, a heart rate sensor, an accelerometer, a global positioning system, or a combination thereof. See, e.g., U.S. Patent Application 2009/0240113, which is incorporated herein by reference. An example of a wireless patch system configured for estimating energy expenditure has been described and includes sensors, electrodes, and accelerometers. This system measures a variety of physiological conditions including temperature, heart rate, respiratory rate, and skin conductivity and uses this information in an algorithm to calculate the number of calories consumed, the number of calories burned, and the net yield. See, e.g., U.S. Patent Application 2010/0049004, which is incorporated herein by reference. Other examples of calorie counters based on activity measurements have been described. See, e.g., U.S. Pat. Nos. 4,100,401; 4,159,416; 5,815,954; and 7,334,472, each of which is incorporated herein by reference. Other means for performing calorimetry include, but are not limited to, the Haldane gravimetric method, open-circuit calorimeter with mask, spirographic method, assessment of heat loss and oxygen consumption.

The one or more sensors of the device can be configured to send data regarding a physiological condition in the subject to the programmable microprocessor of the device or to a electronics module operably connected to the programmable microprocessor. Conversely, the electronics module can be configured to instruct the one or more sensors to collect and transmit data or other information regarding one or more physiological conditions or indicators thereof at specified regular intervals and/or when triggered by sensed events or by initiation of particular device activity. The device may further include information storage. For example, measurement of one or more physiological condition may be collected and stored at specified times on a daily basis with an associated time stamp. More than one physiological condition may be measured simultaneously and associated with one another during processing. For example, measurement of temperature, or a localized temperature of an associated nerve tissue or circulatory tissue, can be assessed at the same time as measurement of blood glucose levels. A temperature measurement can also be triggered by other sensor activity such as when a measured exertion level reaches a specified limit value or immediately following caloric intake.

Power Source

The device as disclosed herein can include at least one power source configured to power the components of the device. The device can further include one or more sensors.

The power source can be one or more of a wireless power source. A wireless power source includes stored power, a battery, or a fuel cell. For the device, the power source can be external, internal, or a combination thereof. The device can be coupled to an external power source through a radio-frequency link. Alternatively, the device can include a self-contained power source made using any means of generation or storage of energy, e.g., a primary battery, a replenishable or rechargeable battery, a thin film battery, a capacitor, or a supercapacitor. A replenishable or rechargeable self-contained power source can be replenished or recharged using a radio-frequency link, an optical link, or other energy-coupling link. See, e.g., U.S. Patent Application No. 2005/0143787, by B. Boveja, which is incorporated herein by reference. In an aspect, the power source for the device is supplied from an external power source via a transcutaneous inductive coupling. See, e.g., U.S. Patent Application 2010/0076524, which is incorporated herein by reference.

The power source can include electrical energy generated by mechanical energy of a subject's movement. For example, the power source can be a linear motion electric power generator that uses a rare earth magnet and a coil positioned to move linearly back and forth relative to one another. The movement of the coil in the field of the magnet generates a current in the coil. See, e.g., U.S. Pat. No. 5,347,186, which is incorporated herein by reference. In this instance, power can be generated as the device moves, e.g., bounces up and down while jogging or while doing other physical activity, as exemplified by the nPower® PEG (Personal Energy Generator, from Tremont Electric, Tremont, Ohio). In an aspect, the power source can be one or more solar panel attached to one or more component of the device such as, for example, a portable refrigeration unit in a backpack with affixed solar panels. See, e.g., U.S. Patent Application 2009/0015022 which is incorporated herein by reference.

In an aspect, the power source can include a rubber film configured to harness energy associated with natural body movements. For example, the power source can include a material made of a ceramic piezoelectric material, e.g., fabricated lead zirconate titanate that is embedded in silicone rubber sheets. The rubber film can harness natural body movements such as walking and breathing as electricity when flexed, converting approximately 80% of mechanical energy into electrical energy. See, e.g., Qi, et al., Nano Lett., 10: 524-528, 2010, which is incorporated herein by reference.

The power source can include one or more of a battery or microbattery, a fuel cell or biofuel cell, or a nuclear battery. One or more power sources of the same or different types can be included in the device, without limitation. Batteries for a device can include a microbattery, e.g., as available from Quallion LLC, Sylmar, Calif. (http://www.quallion.com), or one designed as a film (U.S. Pat. Nos. 5,338,625 and 5,705,293), each of which is incorporated herein by reference. Alternatively, the power source could be one or more fuel cell, for example, a biofuel cell, such as an enzymatic, microbial, or photosynthetic fuel cell (US2003/0152823A1; WO03/106966A2; or Chen T et al.," J. Am. Chem. Soc. 2001, 123: 8630-8631, each of which is incorporated herein by reference). The fuel cell can be of any size, including the micro- or nano-scale. In an aspect, the power source can include laterally packaged piezoelectric fine wires that convert biomechanical energy (e.g., stretching muscles, beating heart, walking) into electrical energy using a nanogenerator. See, e.g., Yang et al., Nature Nanotechnol., 4: 34-39, 2009; Yang et al., Nano Lett., 9: 1201-1205, 2009, each of which is incorporated herein by reference. In another aspect, the power source can include a pressure-rectifying mechanism that utilizes pulsatile changes in blood pressure or an acceleration-rectifying mechanism as used in self-winding watches, or other types of flow-rectifying mechanism capable of deriving energy from other flow parameters. In an embodiment, the power source can be a nuclear battery. See, e.g., Wacharasindhut et al., Appl. Phys. Lett. 2009, 95: 014103, which is incorporated herein by reference.

In an aspect, the power source can be a power receiver capable of receiving power from an acoustic source or electromagnetic source (e.g., infrared energy, or inductively coupled, as described in U.S. Pat. Nos. 6,170,485, and 7,212,110; U.S. Patent Application No. 2005/0228259; and Budgett et al., J. Appl. Physiol. 2007, 102: 1658-1663, each of which is incorporated herein by reference). The power source can include power generated from thermoelectric heating based on the differential between body temperature of a subject and the ambient temperature. See, e.g., U.S. Pat. No. 6,075,199; U.S. Patent Application 2009/0056328, each of which is incorporated herein by reference. In an aspect, the device can include a power transmitter capable of transmitting power (e.g., acoustic power, electrical power, or optical power) from the device to a secondary location. The secondary location can be, for example, one or more bioactive substance module and/or deactivation modules, one or more sensors, another device, or combinations thereof.

The premise behind the development of such a device is to provide a patient with an extracorporeal organ-like device to serve in place of their own organ (liver or pancreas). This device will clean and process the blood just as in a normal liver. As examples of this process could include but not limited to:
1. Acute liver failure brought on by exposure to a toxin such as acetaminophen or mushroom poisoning, by infection such as acute hepatitis A, B or E, by acute onset autoimmune hepatitis, acute alcoholic hepatitis or alcoholic foamy degeneration, by blunt or sharp trauma secondary to surgery, physical accidents, combat or other warzone related injuries.
2. Chronic liver disease like viral hepatitis (HBV or HCV), chronic alcoholic or non-alcoholic fatty liver disease, metabolic diseases (e.g. hereditary hemochromatosis, alpha-1-antitrypsin deficiency, Wilson disease), chronic cholestatic liver diseases (e.g. primary sclerosing cholangitis, primary biliary cholangitis, IgG4 cholangiopathy), autoimmune liver disease (e.g. autoimmune hepatitis).
3. Hereditary or acquired metabolic diseases such as Crigler-Najjar Syndrome (hyperbilirubinemia), glycogen storage disorders (GSD) or primary hyperoxaluria. Here the device can be utilized to act as an auxiliary liver providing the body the necessary proteins needed to bring the body into homeostasis.
4. The device could be utilized as a way to mitigate weapons of mass destruction such as chemical poisoning from the toxins abrin (rosary pea) or mytocitins (blue-green algae) both very powerful hepatic-toxins that could be weaponized against military and general populations alike.
5. The device could be utilized in civilian or military exposures to infectious bio-threats, including, but not limited to *F. tularensis, B. antrhacis, B. pseudomallei*. The device could offer hepatic function support in the case of severe infection, alone or in combination with administered antibiotic agents (e.g. PT159, PT160 and TPR1 (FIG. **

istered to a patient who is also using the device, could be administered via the flow lines into and from the device, or be contained within the device itself.
6. The bio-artificial liver device can be utilized in a variety of other ways, such as drug development or improving liver disease models for study.
7. The bio-artificial liver could be used to sustain a patient receiving highly liver toxic chemotherapeutic agents for malignancy or infection, allowing for higher levels of therapeutic compounds than would otherwise be tolerable, improving outcomes of the treatment.
8. In the case of pancreatic needs the biggest and most challenging disorder is diabetes and the loss of islets. The columns could be filled with islets and provide insulin to the body.
9. The artificial pancreas could be used in physical injury to the pancreas, by blunt or sharp trauma secondary to surgery, physical accidents, combat or other warzone related injuries.
10. The artificial pancreas could also be used in both drug development and disease models.

Commonalties Between Bio Artificial Liver Device and Pancreatic Device

The only commonality between the 2 devices is simple, the cartridge and the decellularized scaffold. However, the design of the device will allow a person to exchange one liver cartridge for a pancreatic cartridge changing the device from hepatic to pancreatic and vice-versa, if needed. The present invention can also be a hybrid of both pancreatic and hepatic tissue.

As for biological labor most of the tasks can be done via automated cultured techniques bringing down manufacturing cost. Even the de-cellularization of the liver can be automated to a degree. Once the liver is acquired and prepared for cannulation and tied on the rest could be automated using timed intervals to switch from detergents to washing procedures. Even the seeding of the empty scaffolds can be automated, if needed.

The Bio-Artificial Liver

Over the past few decades several different types of bio-artificial liver (BAL) devices have been tested on animals, but very few human trials have been conducted. The designs of the devices that did advance to a clinical trial demonstrated some ability to decrease levels of toxic substances in the patient's serum, but were statistically ineffective at improving survival rates among liver failure patients. These disappointing results were attributed to insufficient functional capacity of the liver device as compared to natural liver. Reports describing the deficiencies of current-generation of the liver device have identified two general properties of these BAL that contribute to the relatively poor level of function.

Some of the key factors that will enable ELAD improvement are cell sourcing, maintaining hepatocyte phenotype, and innovative bioreactor design. In light of the scarcity of human liver cells and their limited proliferative potential in vitro, new culture conditions that enhance expansion of primary cells, highly functional immortalized cell lines, or efficient differentiation of stem cell sources will be required. Furthermore, careful attention is required to the integration of the hepatocyte microenvironment and bioreactor design that will result in stable, scalable liver-specific function. As we move forward, it is imperative to integrate our collective past experiences in liver biology, bioreactor design, and clinical treatment of liver disease to develop effective BAL therapies for the future.

Bio-artificial livers are not a permanent alternative to liver transplant. Instead, they would be used to sustain a critically ill patient until a suitable donor organ became available, similar to what dialysis is done for kidney patients. These devices generally take the foim of closed systems containing functional liver cells grown on an artificial matrix. In theory, a patient's blood could be passed through these systems, allowing for the detoxification of drugs and ammonia as well as supplying plasma proteins and glucose to the body. While this concept may seem straightforward, complications in maintaining functional hepatocytes in a three-dimensional culture have limited the development of these systems. Synthetic matrices have proven to be sub-optimal in regards to both the extent of colonization as well as the long-term maintenance of cell functionality and viability.

The discovery that liver stem cells may be derived from bone marrow opens the possibility of colonizing a matrix scaffold with a patient's own cells. We have developed a method for removing all of the cells from an intact liver. This process leaves behind the extracellular matrix (scaffold-building structure) that can be utilized to rebuild the organ. We feel that these intact decellularized livers (IDL) represent an exceptional tool for studies related to building a liver assist device. Having this new tool gives us a remarkable opportunity to advance the field of tissue engineering to the next generation of human treatment.

Extracellular Matrix

Methods are provided herein for the control of cell distribution in the bio-artificial liver by modification of a growth surface with a growth controlling extracellular matrix ("ECM") (or components thereof) alone or in combination with a growth controlling physical matrix or other growth regulating substances.

In living tissue, the ECM is formed from a variety of proteins and polysaccharides which are secreted by cells and assembled into a network in proximity to the cells that secreted them. ECM molecules include glycosaminoglycans and proteoglycans, such as chrondroitin sulfate, fibronectin, heparin sulfate, hyaluron, dermatan sulfate, keratin sulfate, laminin, collagen, heparan sulfate proteoglycan (HSPG) and elastin. In particular, collagen is a major component of ECM in vivo. ECM molecules are known to cause decreased cell proliferation and increased cell differentiation. In addition, acellular ECM when used in the methods of this invention may influence the spatial location of cells encapsulated in the BAL.

ECM may be obtained by culturing cells known to deposit ECM, including cells of mesenchymal or astrocyte origin. Schwann cells can be induced to synthesize ECM when treated with ascorbate and cAMP. These ECM components resemble a precursor form of the basement membrane which support Schwann cell proliferation. Furthermore, naturally produced ECM from endothelial cells and a reconstituted basement membrane gel from Engelbreth Holm-Swarm tumor cells (EHS) supports the growth and differentiation of various epithelial and endothelial cells.

The schematic illustrates how the device will work. Unlike current devices where the plasma/blood flows outside the hepatic cells, which only provides a small percentage of effectiveness. The proposed construct of the device will work in a manner similar to how the native liver functions. In our model the blood/plasma will pass over the hepatic tissue allowing direct contact, which mimics the natural liver environment. By implementing this difference we feel the functional output of our device will be superior in function and mobility.

The Need for the Project

The U.S. Department of Health and Human Services (HHS) calls regenerative medicine the "next evolution of medical treatments" and the "vanguard of 21st century healthcare" in its report, "2020: A New Vision—A Future for Regenerative Medicine". Regenerative medicine encompasses a variety of technologies and approaches for the treatment of diseased or damaged cells and tissues, ranging from cell, biomaterial, and drug therapy for the promotion of regeneration to whole organ/tissue replacement with laboratory grown organs (i.e., tissue engineering).

The applications of regenerative medicine for tissue transplantation alone are staggering. Demand for replacement organs continues to far exceed supply in all cases and for the purposes of this application (FIG. 1 above), on average, 20 people die each day while waiting for a transplant and every ten minutes a new patient is added to the transplant list The numbers would be even higher if one estimates the total number of patients who would benefit from a spectrum of potential regenerative medicine therapies. A significant portion of health care spending is for recurrent treatments of chronic diseases. Given the liver's complexity, there are no simple or widely effective medical solutions to acute liver failure. The only long-term cure for acute liver failure is surgical transplantation. In 2012, according to the United Network for Organ Sharing, fewer than 6,500 liver transplants were performed in the United States due to an insufficient number of available donor organs. In addition, the United Network for Organ Sharing states the average billable charge for a liver transplant in 2011, including the one month before surgery and six months after surgery, was approximately $577,100. There are approximately 16,000 patients currently on the transplant waiting list and approximately 1,500 patients die while waiting each year. Similarly, there are approximately 6,000 liver transplants performed each year in Europe. Outside of transplant, current therapy is defined by the treating facility and is mostly supportive and designed to manage the symptoms and complications associated with acute liver failure. Therefore, this field not only has obvious health benefits, but also offers the possibility to combat rising health care costs. Regenerative medicine offers not only the potential to treat a variety of diseases, but more importantly, to potentially cure them.

Also, the use of regenerative medicine and tissue engineering technologies to develop human tissue bioequivalents/biomimetics could increase the efficacy of preclinical studies. For instance, 3D culture systems could reduce the need for expensive and increasingly unpopular animal studies; thereby reducing the total investment of drug discovery, which is now estimated at $800 million in sales over 12 years. Based upon clinical trials, the current generations of ELAD/BAL have been in development for the past 25 years. To date, the largest randomized, controlled clinical trial (171 patients) failed to demonstrate any increase in patient survival. Outside of transplant, the current therapy is defined as mostly supportive and designed to manage the symptoms and complications associated with the organ failure. There is clearly a clinical need for such a device and a large market share to draw upon.

IHoP

Pancreatic cancer is hard to identify early. The pancreas is deep inside the body, so early tumors can't be seen or felt by health care providers during routine physical exams. People usually have no signs or symptoms until the cancer has already spread to other organs. At this time, no major professional groups recommend routine screening for pancreatic cancer in people who are at average risk due to a complete lack of proven screening tests. No previously evaluated screening test has been shown to lower the risk of dying from this cancer.

Sometimes when a person has pancreatic cancer, the levels of certain proteins in the blood go up. These proteins, called tumor markers, can be detected with blood tests. The tumor markers CA 19-9 and carcinoembryonic antigen (CEA) are the ones most closely tied to pancreatic cancer. But these proteins don't always go up when a person has pancreatic cancer, and even if they do, the cancer is often already advanced by the time this happens. Sometimes levels of these tumor markers can go up even when a person doesn't have pancreatic cancer. For these reasons, blood tests aren't used to screen for pancreatic cancer.

Likewise, the current technology for detecting T1D is only 75% effective in diagnosing and do not screen for pre-T1D states in children or in adults. Early detection of pre-T1D states or of early T1D could facilitate development of early interventions which might prevent full onset, delay on set, or diminish subsequent severity of disease.

Thus, a simple an effective diagnostic tool is desperately needed to aid physician in treating patients with various pancreatic disorders. Islet homeostasis protein ("IHoP") has been reported to be a potential new biomarker for early diagnosis of such conditions, as described above, including early detection of incipient or early stages of T1D, pancreatic malignancy, and other pancreatic disorders. (See Oh, S H et al. Characterization of a novel functional protein in the pancreatic islet: islet homeostasis protein regulation of glucagon synthesis in alpha cells. Pancreas. 2012 January; 41(1):22-30).

The present invention includes methods of detection of IHoP in body fluids, cells, and tissue samples. The nucleic acid sequence encoding IHoP is set forth in SEQ ID NO: 1, and the IHoP amino acid sequence is set forth in SEQ ID NO: 2; also see U.S. Pat. No. 9,109,042, the entirety of which is incorporated herein by reference, specifically FIG. 7 and FIG. 8.

IHoP may be detected in fluids, such as blood, plasma, serum, sweat, saliva, urine, interstitial fluid, lymph, or liquid contents of the esophagus, stomach, duodenum, jejunum or colon, or in stool.

IHoP may be detected intact cells (derived from fine needle aspirations, biopsies, cell isolation from tissues samples, including by flow cytometry) or in intact tissues (obtained from intraoperative biopsies, endoscopic biopsies, surgical resection specimens, autopsy specimens) of tumors or non-neoplastic pancreas.

IHoP may be detected and assessed as present vs. absent, semi quantitatively or quantitatively.

IHoP may be detected through chemical means (inclusive of wet and dry methodologies) or by immunodetection (such as lateral flow, immunostaining, immunofluorescent staining), by leptin labeling, or by in situ hybridization for IHoP mRNA.

IHoP levels may be assessed for above normal values or for rising values even if within normal limits.

Changes in IHoP from normal baseline may indicate a need for further work up to investigate incipient or pre-T1DM or established T1DM, in children and adults, both in patients without other diabetes or in patients with established type 2 diabetes mellitus (T2DM) with suspicion of concomitant, developing or developed T1DM.

Changes in IHoP from normal baseline may indicate the presence of benign or malignant neoplasia or tumor like conditions including acinar cell cystadenoma, serous cystadenoma, pancreatic intraepithelial neoplasia (PANIN) grade 3, intraductal papillary mucinous neoplasia with low or intermediate or high grade dysplasia, intraductal tubulopapillary neoplasm, mucinous cystic neoplasm with low or intermediate or high grade dysplasia, Ductal adenocarcinoma, adenosquamous carcinoma, colloid carcinoma, mucinous non-cystic carcinoma, hepatoid carcinoma, medullary carcinoma, signet ring cell carcinoma, undifferentiated carcinoma undifferentiated carcinoma with osteoclast like giant cells, acinar cell carcinoma acinar cell cystadenocarcinoma, intraductal papillary mucinous neoplasm with invasive carcinoma, mixed acinar-ductal carcinoma, mixed acinar-neuroendocrine carcinoma, mixed acinar-neuroendocrine-ductal carcinoma, mixed ductal neuroendocrine carcinoma, mucinous cystic neoplasm with invasive carcinoma, pancreatoblastoma, serous cystadenocarcinoma, solid-pseudopapillary neoplasm, pancreatic neuroendocrine microadenoma, neuroendocrine tumor grade 1 or grad 2, neuroendocrine carcinoma, large cell or small cell variants, EC cell, serotonin-producing NET (carcinoid), gastrinoma, glucagonoma, insulinoma, somatostatinoma, VIPoma, nesidioblastosis, mature teratoma, primary pancreatic mesenchymal tumors and lymphomas.

Changes in IHoP from normal baseline may indicate the presence of inflammatory pancreatic conditions such as acute and/or chronic pancreatitis, idiopathic or secondary to alcohol use, hypolipoproteinemia, hypercalcemia, drugs or toxins, mutations in genes encoding trypsin, trypsin regulators, or proteins that regulate calcium metabolism, gallstones, trauma iatrogenic injury, operative or endoscopy associated, shock, atheroembolism, vasculitis, cystic fibrosis or mumps.

Changes in IHoP from normal baseline may indicate pancreatitis do to the presence of inherited genetic disorders such as gene deletions/mutations/amplifications CFTR, PRSS1, SPINK1, CASSR, CTRC, and CPA1.

Changes in IHoP from normal baseline may indicate the presence of benign or malignant pancreatic cysts.

Changes in IHoP from normal baseline may indicate increased risk for development of T1DM, incipient T1DM, early stage T1DM, or advanced stage T1DM, in the absence of pre-existing or concomitant T2DM.

Changes in IHoP from normal baseline may indicated a risk of T2DM in association with MODY1, MODY2, or MODY3, maternally inherited diabetes and deafness syndrome, defects in proinsulin conversion, insulin gene mutations, type A insulin resistance, lipoatrophic diabetes, chronic pancreatitis, pancreatectomy or trauma, neoplasia, cystic fibrosis, hemochromatosis, fibrocalculous pancreatopathy, acromegaly, Cushing syndrome, hyperthyroidism, pheochromocytoma, glucagonoma, viral infections (e.g. cytomegalovirus, Coxsackie B virus, congenital rubella), drugs (e.g. glucocorticoids, thyroid hormone, interferon-alpha, protease inhibitors, beta-adrenergic agonists, thiazides, nicotinic acid, phenytoin, Vacor, Down syndrome, Klinefelter syndrome, Turner syndrome, Prader-Willi syndrome and gestational diabetes.

Changes in IHoP from normal baseline may be used to initiate further screening or diagnostic procedures appropriate to all the conditions named above.

Changes in IHoP between sequential values, from normal to abnormal, abnormal to normal, or within different abnormal ranges may be used to indicate disease progression or disease regression (either spontaneously or in response to treatment).

Biological Samples

Preferred biological samples in which the assays of the invention are performed include bodily fluids, pancreatic tissue and cells, and those tissues known to comprise cancer cells arising from a metastasis of a pancreatic cancer, such as, for example, in carcinomas of the ovary lung, prostate, breast, colon, placenta, or omentum, and in cells of brain anaplastic oligodendrogliomas.

Bodily fluids shall be taken to include urine, ascites, whole blood, serum, peripheral blood mononuclear cells (PBMC), or buffy coat fraction.

In the present context, the term "cancer cell" includes any biological specimen or sample comprising a cancer cell irrespective of its degree of isolation or purity, such as, for example, tissues, organs, cell lines, bodily fluids, or histology specimens that comprise a cell in the early stages of transformation or having been transformed.

As the present invention is particularly useful for the early detection and prognosis of cancer in the short term or in the medium-to-long term, the definition of "cancer cell" is not to be limited by the stage of a cancer in the subject from which said cancer cell is derived (i.e. whether or not the patient is in remission or undergoing disease recurrence or whether or not the cancer is a primary tumor or the consequence of metastases). Nor is the term "cancer cell" to be limited by the stage of the cell cycle of said cancer cell.

Preferably, the sample comprises pancreatic tissue, prostate tissue, kidney tissue, uterine tissue, placenta, a cervical specimen, omentum, rectal tissue, brain tissue, bone tissue, lung tissue, lymphatic tissue, urine, semen, blood, abdominal fluid, serum, or faeces, or a cell preparation or nucleic acid preparation derived therefrom. More preferably, the sample comprises serum or abdominal fluid, or a tissue selected from the group consisting of: pancreas, lymph, lung, liver, brain, placenta, brain, omentum, and prostate. Even more preferably, the sample comprises serum or abdominal fluid, pancreas, or lymph node tissue. The sample can be prepared on a solid matrix for histological analyses, or alternatively, in a suitable solution such as, for example, an extraction buffer or suspension buffer, and the present invention clearly extends to the testing of biological solutions thus prepared.

Detecting Expression

A variety of protocols for detecting and measuring the expression of a IHoP polypeptide, using either polyclonal or monoclonal antibodies specific for the polypeptide, are known in the art. Examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on a IHoP polypeptide can be used, or a competitive binding assay can be employed. These and other assays are described in Hampton et al., SEROLOGICAL METHODS: A LABORATORY MANUAL, APS Press, St. Paul, Minn., 1990) and Maddox et al., J. Exp. Med. 158, 12111216, 1983).

Expression and Purification of Polypeptides

Host cells transformed with nucleotide sequences encoding IHoP polypeptide can be cultured under conditions suitable for the expression and recovery of the protein from cell culture. The polypeptide produced by a transformed cell can be secreted or contained intracellularly depending on the sequence and/or the vector used. As will be understood by those of skill in the art, expression vectors containing polynucleotides which encode IHoP polypeptides can be designed to contain signal sequences which direct secretion of soluble IHoP polypeptides through a prokaryotic or eukaryotic cell membrane or which direct the membrane insertion of membrane-bound IHoP polypeptide.

Antibodies

Antibodies are referenced herein and various aspects of the subject invention utilize antibodies specific to IHoP polypeptide(s). As described above, one example of an therapeutic agent may pertain to an antibody. Any type of antibody known in the art can be generated to bind specifically to an epitope of a IHoP polypeptide. "Antibody" as used herein includes intact immunoglobulin molecules, as well as fragments thereof, such as Fab, F(ab').sub.2, and Fv, which are capable of binding an epitope of a IHoP polypeptide (SEQ ID NO: 2). Typically, at least 6, 8, 10, or 12 contiguous amino acids are required to form an epitope. However, epitopes which involve non-contiguous amino acids may require more, e.g., at least 15, 25, or 50 amino acids. Antibodies which target and bind the IHoP protein are exemplified in U.S. Pat. No. 9,109,042, the entirety of which is incorporated herein by reference, specifically FIG. 1, and column 2, lines 33-52.

An antibody which specifically binds to an epitope of a IHoP polypeptide can be used therapeutically, as mentioned, as well as in immunochemical assays, such as Western blots, ELISAs, radioimmunoassays, immunohistochemical assays, immunoprecipitations, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody which specifically binds to the immunogen. Antibodies useful for embodiments of the subject invention may be polyclonal, but are preferably monoclonal antibodies.

Accordingly, some examples of an agent having therapeutic activity, such as delaying the onset of diabetes, as described herein, or otherwise modulating activity of IHoP, include but are not limited to an antisense nucleic acid molecule, small molecule IHoP inhibitors, peptide inhibitors, a specific antibody, ribozyme, siRNA or a IHoP polypeptide binding molecule targeted to IHoP, or an antibody specific to IHoP. Agents can be used in an animal model to determine the efficacy, toxicity, or side effects of treatment with such an agent. In addition, compositions may include a conjunctive agent in addition to the therapeutic agents of the present invention.

The invention also provides monoclonal or polyclonal antibodies that bind specifically to polypeptides of the invention or fragments thereof. Thus, the present invention further provides a process for the production of monoclonal or polyclonal antibodies to polypeptides of the invention.

The phrase "binds specifically" to a polypeptide means that the binding of the antibody to the protein or peptide is determinative of the presence of the protein, in a heterogeneous population of proteins and other biologics. Thus, under designated immunoassay conditions, the specified antibodies bind to a particular protein at least two times the background and more typically more than 10 to 100 times background. Typically, antibodies of the invention bind to a protein of interest with a Kd of at least about 0.1 mM, more usually at least about 1 µM, preferably at least about 0.1 µM, and most preferably at least, 0.01 µM.

Reference herein to antibody or antibodies includes whole polyclonal and monoclonal antibodies, and parts thereof, either alone or conjugated with other moieties. Antibody parts include Fab and F(ab)$_2$ fragments and single chain antibodies. The antibodies may be made in vivo in suitable laboratory animals, or, in the case of engineered antibodies (Single Chain Antibodies or SCABS, etc) using recombinant DNA techniques in vitro.

In accordance with this aspect of the invention, the antibodies may be produced for the purposes, of immunizing the subject, in which case high titer or neutralizing antibodies that bind to a B cell epitope will be especially preferred. Suitable subjects for immunization will, of course, depend upon the immunizing antigen or antigenic B cell epitope. It is contemplated that the present invention will be broadly applicable to the immunization of a wide range of animals, such as, for example, farm animals (e.g. horses, cattle, sheep, pigs, goats, chickens, ducks, turkeys, and the like), laboratory animals (e.g. rats, mice, guinea pigs, rabbits), domestic animals (cats, dogs, birds and the like), feral or wild exotic animals (e.g. possums, cats, pigs, buffalo, wild dogs and the like) and humans.

Alternatively, the antibodies may be for commercial or diagnostic purposes, in which case the subject to whom the diagnostic/prognostic protein or immunogenic fragment or epitope thereof is administered will most likely be a laboratory or farm animal. A wide range of animal species are used for the production of antisera. Typically the animal used for production of antisera is a rabbit, a mouse, rat, hamster, guinea pig, goat, sheep, pig, dog, horse, or chicken. Because of the relatively large blood volume of rabbits, a rabbit is a preferred choice for production of polyclonal antibodies. However, as will be known to those skilled in the art, larger amounts of immunogen are required to obtain high antibodies from large animals as opposed to smaller animals such as mice. In such cases, it will be desirable to isolate the antibody from the immunized animal.

Preferably, the antibody is a high titer antibody. By "high titer" means a sufficiently high titer to be suitable for use in diagnostic or therapeutic applications. As will be known in the art, there is some variation in what might be considered "high titer". For most applications a titer of at least about $10^3$-$10^4$ is preferred. More preferably, the antibody titer will be in the range from about $10^4$ to about $10^5$, even more preferably in the range from about $10^5$ to about $10^6$.

More preferably, in the case of B cell epitopes from pathogens, viruses or bacteria, the antibody is a neutralizing antibody (i.e. it is capable of neutralizing the infectivity of the organism fro which the B cell epitope is derived).

To generate antibodies, the diagnostic/prognostic protein or immunogenic fragment or epitope thereof, optionally formulated with any suitable or desired carrier, adjuvant, BRM, or pharmaceutically acceptable excipient, is conveniently administered in the form of an injectable composition. Injection may be intranasal, intramuscular, sub-cutaneous, intravenous, intradermal, intraperitoneal, or by other known route. For intravenous injection, it is desirable to include one or more fluid and nutrient replenishers. Means for preparing and characterizing antibodies are well known in the art. (See, e.g., ANTIBODIES: A LABORATORY MANUAL, Cold Spring Harbor Laboratory, 1988, incorporated herein by reference).

The efficacy of the diagnostic/prognostic protein or immunogenic fragment or epitope thereof in producing an antibody is established by injecting an animal, for example, a mouse, rat, rabbit, guinea pig, dog, horse, cow, goat or pig, with a formulation comprising the diagnostic/prognostic protein or immunogenic fragment or epitope thereof, and then monitoring the immune response to the B cell epitope, as described in the Examples. Both primary and secondary immune responses are monitored. The antibody titer is determined using any conventional immunoassay, such as, for example, ELISA, or radio immunoassay.

The production of polyclonal antibodies may be monitored by sampling blood of the immunized animal at various points following immunization. A second, booster injection, may be given, if required to achieve a desired antibody titer. The process of boosting and titering is repeated until a suitable titer is achieved. When a desired level of immunogenicity is obtained, the immunized animal is bled and the serum isolated and stored, and/or the animal is used to generate monoclonal antibodies (Mabs).

For the production of monoclonal antibodies (Mabs) any one of a number of well-known techniques may be used, such as, for example, the procedure exemplified in U.S. Pat. No. 4,196,265, incorporated herein by reference.

For example, a suitable animal will be immunized with an effective amount of the diagnostic/prognostic protein or immunogenic fragment or epitope thereof under conditions sufficient to stimulate antibody producing cells. Rodents such as mice and rats are preferred animals, however, the use of rabbit, sheep, or frog cells is also possible. The use of rats may provide certain advantages, but mice are preferred, with the BALB/c mouse being most preferred as the most routinely used animal and one that generally gives a higher percentage of stable fusions.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer removed. Spleen lymphocytes are obtained by homogenizing the spleen with a syringe. Typically, a spleen from an immunized mouse contains approximately $5 \times 10^7$ to $2 \times 10^8$ lymphocytes.

The B cells from the immunized animal are then fused with cells of an immortal myeloma cell, generally derived from the same species as the animal that was immunized with the diagnostic/prognostic protein or immunogenic fragment or epitope thereof. Myeloma cell lines suited for use in hybridoma-producing fusion procedures preferably are non-antibody-producing, have high fusion efficiency and enzyme deficiencies that render them incapable of growing in certain selective media which support the growth of only the desired fused cells, or hybridomas. Any one of a number of myeloma cells may be used and these are known to those of skill in the art (e.g. murine P3-X63/Ag8, X63-Ag8.653, NS1/1.Ag 4 1, Sp210-Ag14, FO, NSO/U, MPC-11, MPC11-X45-GTG 1.7 and S194/5XX0; or rat R210.RCY3, Y3-Ag 1.2.3, IR983F and 4B210; and U-266, GM1500-GRG2, LICR-LON-HMy2 and UC729-6). A preferred murine myeloma cell is the NS-1 myeloma cell line (also termed P3-NS-1-Ag4-1), which is readily available from the NIGMS Human Genetic Mutant Cell Repository under Accession No. GM3573. Alternatively, a murine myeloma SP2/0 non-producer cell line that is 8-azaguanine-resistant is used.

To generate hybrids of antibody-producing spleen or lymph node cells and myeloma cells, somatic cells are mixed with myeloma cells in a proportion between about 20:1 to about 1:1, respectively, in the presence of an agent or agents (chemical or electrical) that promote the fusion of cell membranes. Fusion methods using Sendai virus have been described by Kohler and Milstein, Nature 256, 495-497, 1975; and Kohler and Milstein, Eur. I Immunol. 6, 511-519, 1976. Methods using polyethylene glycol (PEG), such as 37% (v/v) PEG, are described in detail by Gefter et al., Somatic Cell Genet 3, 231-236, 1977. The use of electrically induced fusion methods is also appropriate.

Hybrids are amplified by culture in a selective medium comprising an agent that blocks the de novo synthesis of nucleotides in the tissue culture media. Exemplary and preferred agents are aminopterin, methotrexate and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT, because only those hybridomas capable of operating nucleotide salvage pathways are able to survive in HAT medium, whereas myeloma cells are defective in key enzymes of the salvage pathway, (e.g., hypoxanthine phosphoribosyl transferase or HPRT), and they cannot survive. B cells can operate this salvage pathway, but they have a limited life span in culture and generally die within about two weeks. Accordingly, the only cells that can survive in the selective media are those hybrids formed from myeloma and B cells.

The amplified hybridomas are subjected to a functional selection for antibody specificity and/or titer, such as, for example, by immunoassay (e.g. radioimmunoassay, enzyme immunoassay, cytotoxicity assay, plaque assay, dot immunobinding assay, and the like).

The selected hybridomas are serially diluted and cloned into individual antibody-producing cell lines, which clones can then be propagated indefinitely to provide MAbs. The cell lines may be exploited for MAb production in two basic ways. A sample of the hybridoma is injected, usually in the peritoneal cavity, into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they are readily obtained in high concentrations. MAbs produced by either means may be further purified, if desired, using filtration, centrifugation and various chromatographic methods such as HPLC or affinity chromatography.

Monoclonal antibodies of the present invention also include anti-idiotypic antibodies produced by methods well-known in the art. Monoclonal antibodies according to the present invention also may be monoclonal heteroconjugates, (i.e., hybrids of two or more antibody molecules). In another embodiment, monoclonal antibodies according to the invention are chimeric monoclonal antibodies. In one approach, the chimeric monoclonal antibody is engineered by cloning recombinant DNA containing the promoter, leader, and variable-region sequences from a mouse anti-PSA producing cell and the constant-region exons from a human antibody gene. The antibody encoded by such a recombinant gene is a mouse-human chimera. Its antibody specificity is determined by the variable region derived from mouse sequences. Its isotype, which is determined by the constant region, is derived from human DNA.

In another embodiment, the monoclonal antibody according to the present invention is a "humanized" monoclonal antibody, produced by any one of a number of techniques well-known in the art. That is, mouse complementary determining regions ("CDRs") are transferred from heavy and light V-chains of the mouse Ig into a human V-domain, followed by the replacement of some human residues in the framework regions of their murine counterparts. "Humanized" monoclonal antibodies in accordance with this invention are especially suitable for use in vivo in diagnostic and therapeutic methods.

As stated above, the monoclonal antibodies and fragments thereof according to this invention are multiplied according to in vitro and in vivo methods well-known in the art. Multiplication in vitro is carried out in suitable culture media such as Dulbecco's modified Eagle medium or RPMI 1640 medium, optionally replenished by a mammalian serum such as fetal calf serum or trace elements and growth-sustaining supplements, e.g., feeder cells, such as normal mouse peritoneal exudate cells, spleen cells, bone marrow macrophages or the like. In vitro production provides relatively pure antibody preparations and allows scale-up to give large amounts of the desired antibodies. Techniques for large scale hybridoma cultivation under tissue culture conditions are known in the art and include homogenous suspension culture, (e.g., in an airlift reactor or in a continuous stirrer reactor or immobilized or entrapped cell culture).

Large amounts of the monoclonal antibody of the present invention also may be obtained by multiplying hybridoma cells in vivo. Cell clones are injected into mammals which are histocompatible with the parent cells, (e.g., syngeneic mice, to cause growth of antibody-producing tumors. Optionally, the animals are primed with a hydrocarbon, especially oils such as Pristane (tetramethylpentadecane) prior to injection.

In accordance with the present invention, fragments of the monoclonal antibody of the invention are obtained from monoclonal antibodies produced as described above, by methods which include digestion with enzymes such as pepsin or papain and/or cleavage of disulfide bonds by chemical reduction. Alternatively, monoclonal antibody fragments encompassed by the present invention are synthesized using an automated peptide synthesizers, or they may be produced manually using techniques well known in the art.

The monoclonal conjugates of the present invention are prepared by methods known in the art, e.g., by reacting a monoclonal antibody prepared as described above with, for instance, an enzyme in the presence of a coupling agent such as glutaraldehyde or periodate. Conjugates with fluorescein markers are prepared in the presence of these coupling agents, or by reaction with an isothiocyanate. Conjugates with metal chelates are similarly produced. Other moieties to which antibodies may be conjugated include radionuclides such as, for example, $^3$H, $^{125}$I, $^{32}$P, $^{35}$S, $^{14}$C, $^{51}$Cr, $^{36}$Cl, $^{57}$Co, $^{59}$Co, $^{59}$Fe, $^{75}$Se, and $^{152}$Eu.

Radioactively labeled monoclonal antibodies of the present invention are produced according to well-known methods in the art. For instance, monoclonal antibodies are iodinated by contact with sodium or potassium iodide and a chemical oxidizing agent such as sodium hypochlorite, or an enzymatic oxidizing agent, such as lactoperoxidase. Monoclonal antibodies according to the invention may be labeled with technetium$^{99}$ by ligand exchange process, for example, by reducing pertechnetate with stannous solution, chelating the reduced technetium onto a Sephadex column and applying the antibody to this column or by direct labeling techniques, (e.g., by incubating pertechnate, a reducing agent such as $SNCl_2$, a buffer solution such as sodium-potassium phthalate solution, and the antibody).

Any immunoassay may be used to monitor antibody production by the diagnostic/prognostic protein or immunogenic fragment or epitope thereof. Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and Western blotting, dot blotting, FACS analyses, and the like may also be used.

Most preferably, the assay will be capable of generating quantitative results.

For example, antibodies are tested in simple competition assays. A known antibody preparation that binds to the B cell epitope and the test antibody are incubated with an antigen composition comprising the B cell epitope, preferably in the context of the native antigen. "Antigen composition" as used herein means any composition that contains some version of the B cell epitope in an accessible form. Antigen-coated wells of an ELISA plate are particularly preferred. In one embodiment, one would pre-mix the known antibodies with varying amounts of the test antibodies (e.g., 1:1, 1:10 and 1:100) for a period of time prior to applying to the antigen composition. If one of the known antibodies is labeled, direct detection of the label bound to the antigen is possible; comparison to an unmixed sample assay will determine competition by the test antibody and, hence, cross-reactivity. Alternatively, using secondary antibodies specific for either the known or test antibody, one will be able to determine competition.

An antibody that binds to the antigen composition will be able to effectively compete for binding of the known antibody and thus will significantly reduce binding of the latter. The reactivity of the known antibodies in the absence of any test antibody is the control. A significant reduction in reactivity in the presence of a test antibody is indicative of a test antibody that binds to the B cell epitope (i.e., it cross-reacts with the known antibody).

In one exemplary ELISA, the antibodies against the diagnostic/prognostic protein or immunogenic fragment or B cell epitope are immobilized onto a selected surface exhibiting protein affinity, such as a well in a polystyrene microtiter plate. Then, a composition containing a peptide comprising the B cell epitope is added to the wells. After binding and washing to remove non-specifically bound immune complexes, the bound epitope may be detected. Detection is generally achieved by the addition of a second antibody that is known to bind to the B cell epitope and is linked to a detectable label. This type of ELISA is a simple "sandwich ELISA". Detection may also be achieved by the addition of said second antibody, followed by the addition of a third antibody that has binding affinity for the second antibody, with the third antibody being linked to a detectable label.

Antibodies of the invention may be bound to a solid support and/or packaged into kits in a suitable container along with suitable reagents, controls, instructions and the like.

Immunoassay Formats

In one embodiment, a cancer-associated protein or an immunogenic fragment or epitope thereof is detected in a patient sample, wherein the level of the protein or immunogenic fragment or epitope in the sample is indicative of pancreatic cancer or disease recurrence or an indicator of poor survival. Preferably, the method comprises contacting a biological sample derived from the subject with an antibody capable of binding to a cancer-associated protein or an immunogenic fragment or epitope thereof, and detecting the formation of an antigen-antibody complex.

In another embodiment, an antibody against a cancer-associated protein or epitope thereof is detected in a patient sample, wherein the level of the antibody in the sample is indicative of pancreatic cancer or disease recurrence or an indicator of poor survival. Preferably, the method comprises contacting a biological sample derived from the subject with a cancer-associated protein or an antigenic fragment e.g., a B cell epitope or other immunogenic fragment thereof, and detecting the formation of an antigen-antibody complex.

The diagnostic assays of the invention are useful for determining the progression of pancreatic cancer or a metastasis thereof in a subject. In accordance with these prognostic applications of the invention, the level of a cancer-associated protein or an immunogenic fragment or epitope thereof in a biological sample is correlated with the disease state e.g., as determined by clinical symptoms or biochemical tests.

Accordingly, a further embodiment of the invention provides a method for detecting a pancreatic cancer cell in a subject, said method comprising:
(i) determining the level of a pancreatic cancer-associate protein in a test sample from said subject; and
(ii) comparing the level determined at (i) to the level of said pancreatic cancer-associated protein in a comparable sample from a healthy or normal individual, wherein a level of said pancreatic cancer-associate protein at (i) that is modified in the test sample relative to the comparable sample from the normal or healthy individual is indicative of the presence of a pancreatic cancer cell in said subject.

In one embodiment of the diagnostic/prognostic methods described herein, the biological sample is obtained previously from the subject. In accordance with such an embodiment, the prognostic or diagnostic method is performed ex vivo.

In yet another embodiment, the subject diagnostic/prognostic methods further comprise processing the sample from the subject to produce a derivative or extract that comprises the analyte.

Preferred detection systems contemplated herein include any known assay for detecting proteins or antibodies in a biological sample isolated from a human subject, such as, for example, SDS/PAGE, isoelectric focusing, 2-dimensional gel electrophoresis comprising SDS/PAGE and isoelectric focusing, an immunoassay, a detection based system using an antibody or non-antibody ligand of the protein, such as, for example, a small molecule (e.g. a chemical compound, agonist, antagonist, allosteric modulator, competitive inhibitor, or non-competitive inhibitor, of the protein). In accordance with these embodiments, the antibody or small molecule may be used in any standard solid phase or solution phase assay format amenable to the detection of proteins. Optical or fluorescent detection, such as, for example, using mass spectrometry, MALDI-TOF, biosensor technology, evanescent fiber optics, or fluorescence resonance energy transfer, is clearly encompassed by the present invention. Assay systems suitable for use in high throughput screening of mass samples, particularly a high throughput spectroscopy resonance method (e.g. MALDI-TOF, electrospray MS or nano-electrospray MS), are particularly contemplated.

Immunoassay formats are particularly preferred, e.g., selected from the group consisting of, an immunoblot, a Western blot, a dot blot, an enzyme linked immunosorbent assay (ELISA), radioimmunoassay (RIA), enzyme immunoassay. Modified immunoassays utilizing fluorescence resonance energy transfer (FRET), isotope-coded affinity tags (ICAT), matrix-assisted laser desorption/ionization time of flight (MALDI-TOF), electrospray ionization (ESI), biosensor technology, evanescent fiber-optics technology or protein chip technology are also useful.

Preferably, the assay is a semi-quantitative assay or quantitative assay.

Standard solid phase ELISA formats are particularly useful in determining the concentration of a protein or antibody from a variety of patient samples.

In one form such as an assay involves immobilising a biological sample comprising antibodies against the cancer-associated protein or epitope, or alternatively a pancreatic cancer-associated protein or an immunogenic fragment thereof, onto a solid matrix, such as, for example a polystyrene or polycarbonate microwell or dipstick, a membrane, or a glass support (e.g. a glass slide).

In the case of an antigen-based assay, an antibody that specifically binds a pancreatic cancer-associated protein is brought into direct contact with the immobilised biological sample, and forms a direct bond with any of its target protein present in said sample. For an antibody-based assay, an immobilized pancreatic cancer-associated protein or an immunogenic fragment or epitope thereof is contacted with the sample. The added antibody or protein in solution is generally labelled with a detectable reporter molecule, such as for example, a fluorescent label (e.g. FITC or Texas Red) or an enzyme (e.g. horseradish peroxidase (HRP)), alkaline phosphatase (AP) or β-galactosidase. Alternatively, or in addition, a second labelled antibody can be used that binds to the first antibody or to the isolated/recombinant antigen. Following washing to remove any unbound antibody or antigen, as appropriate, the label is detected either directly, in the case of a fluorescent label, or through the addition of a substrate, such as for example hydrogen peroxide, TMB, or toluidine, or 5-bromo-4-chloro-3-indol-beta-D-galaotopyranbside (x-gal).

Such ELISA based systems are particularly suitable for quantification of the amount of a protein or antibody in a sample, such as, for example, by calibrating the detection system against known amounts of a standard.

In another form, an ELISA consists of immobilizing an antibody that specifically binds a pancreatic cancer-associated protein on a solid matrix, such as, for example, a membrane, a polystyrene or polycarbonate microwell, a polystyrene or polycarbonate dipstick or a glass support. A patient sample is then brought into physical relation with said antibody, and the antigen in the sample is bound or 'captured'. The bound protein can then be detected using a labeled antibody. For example if the protein is captured from a human sample, an anti-human antibody is used to detect the captured protein. Alternatively, a third labeled antibody can be used that binds the second (detecting) antibody.

It will be apparent to the skilled person that the assay formats described herein are amenable to high throughput formats, such as, for example automation of screening processes, or a microarray format as described in Mendoza et al, Biotechniques 27(4): 778-788, 1999. Furthermore, variations of the above described assay will be apparent to those skilled in the art, such as, for example, a competitive ELISA.

Alternatively, the presence of antibodies against the cancer-associate protein, or alternatively an ovarian cancer-associated protein or an immunogenic fragment thereof, is detected using a radioimmunoassay (RIA). The basic principle of the assay is the use of a radiolabelled antibody or antigen to detect antibody antigen interactions. For example, an antibody that specifically binds to a pancreatic cancer-associated protein can be bound to a solid support and a biological sample brought into direct contact with said antibody. To detect the bound antigen, an isolated and/or recombinant form of the antigen is radiolabeled is brought into contact with the same antibody. Following washing the amount of bound radioactivity is detected. As any antigen in the biological sample Inhibits binding of the radiolabeled antigen the amount of radioactivity detected is inversely proportional to the amount of antigen in the sample. Such an assay may be quantitated by using a standard curve using increasing known concentrations of the isolated antigen.

As will be apparent to the skilled artisan, such an assay may be modified to use any reporter molecule, such as, for example, an enzyme or a fluorescent molecule, in place of a radioactive label.

Western blotting is also useful for detecting a pancreatic cancer-associated protein or an immunogenic fragment thereof. In such an assay protein from a biological sample is separated using sodium dodecyl sulphate (SDS) polyacrylamide gel electrophoresis (SDS-PAGE) using techniques well known in the art and described in, for example, Scopes (In: Protein Purification: Principles and Practice, Third Edition, Springer Verlag, 1994). Separated proteins are then transferred to a solid support, such as, for example, a membrane or more specifically PVDF membrane, using methods well known in the art, for example, electrotransfer. This membrane may then be blocked and probed with a labeled antibody or ligand that specifically binds a pancreatic cancer-associated protein. Alternatively, a labeled secondary, or even tertiary, antibody or ligand can be used to detect the binding of a specific primary antibody.

High-throughput methods for detecting the presence or absence of antibodies, or alternatively pancreatic cancer-associated protein or an immunogenic fragment thereof are particularly preferred.

In one embodiment, MALDI-TOF is used for the rapid identification of a protein. Accordingly, there is no need to detect the proteins of interest using an antibody or ligand that specifically binds to the protein of interest. Rather, proteins from a biological sample are separated using gel electrophoresis using methods well known in the art and those proteins at approximately the correct molecular weight and/or isoelectric point are analysed using MALDI-TOF to determine the presence or absence of a protein of interest.

Alternatively, MALDI or ESI or a combination of approaches is used to determine the concentration of a particular protein in a biological sample, such as, for example sputum. Such proteins are preferably well characterised previously with regard to parameters such as molecular weight and isoelectric point.

Biosensor devices generally employ an electrode surface in combination with current or impedance measuring elements to be integrated into a device in combination with the assay substrate (such as that described in U.S. Pat. No. 5,567,301). An antibody or ligand that specifically binds to a protein of interest is preferably incorporated onto the surface of a biosensor device and a biological sample isolated from a patient (for example sputum that has been solubilised using the methods described herein) contacted to said device. A change in the detected current or impedance by the biosensor device indicates protein binding to said antibody or ligand. Some forms of biosensors known in the art also rely on surface plasmon resonance to detect protein interactions, whereby a change in the surface plasmon resonance surface of reflection is indicative of a protein binding to a ligand or antibody (U.S. Pat. Nos. 5,485,277 and 5,492,840).

Biosensors are of particular use in high throughput analysis due to the ease of adapting such systems to micro- or nano-scales. Furthermore, such systems are conveniently adapted to incorporate several detection reagents, allowing for multiplexing of diagnostic reagents in a single biosensor unit. This permits the simultaneous detection of several epitopes in a small amount of body fluids.

Evanescent biosensors are also preferred as they do not require the pretreatment of a biological sample prior to detection of a protein of interest. An evanescent biosensor generally relies upon light of a predetermined wavelength interacting with a fluorescent molecule, such as for example, a fluorescent antibody attached near the probe's surface, to emit fluorescence at a different wavelength upon binding of the diagnostic protein to the antibody or ligand.

To produce protein chips, the proteins, peptides, polypeptides, antibodies or ligands that are able to bind specific antibodies or proteins of interest are bound to a solid support such as for example glass, polycarbonate, polytetrafluoroethylene, polystyrene, silicon oxide, metal or silicon nitride. This immobilization is either direct (e.g. by covalent linkage, such as, for example, Schiff s base formation, disulfide linkage, or amide or urea bond formation) or indirect. Methods of generating a protein chip are known in the art and are described in for example U.S. Patent Application No. 20020136821, 20020192654, 20020102617 and U.S. Pat. No. 6,391,625. In order to bind a protein to a solid support it is often necessary to treat the solid support so as to create chemically reactive groups on the surface, such as, for example, with an aldehyde-containing silane reagent. Alternatively, an antibody or ligand may be captured on a microfabricated polyacrylamide gel pad and accelerated into the gel using microelectrophoresis as described in, Arenkov et al. *Anal. Biochem.* 278:123-131, 2000.

A protein chip is preferably generated such that several proteins, ligands or antibodies are arrayed on said chip. This format permits the simultaneous screening for the presence of several proteins in a sample.

Alternatively, a protein chip may comprise only one protein, ligand or antibody, and be used to screen one or more patient samples for the presence of one polypeptide of interest. Such a chip may also be used to simultaneously screen an array of patient samples for a polypeptide of interest.

Preferably, a sample to be analysed using a protein chip is attached to a reporter molecule, such as, for example, a fluorescent molecule, a radioactive molecule, an enzyme, or an antibody that is detectable using methods well known in the art. Accordingly, by contacting a protein chip with a labeled sample and subsequent washing to remove any unbound proteins the presence of a bound protein is detected using methods well known in the art, such as, for example using a DNA microarray reader.

Alternatively, biomolecular interaction analysis-mass spectrometry (BIA-MS) is used to rapidly detect and characterise a protein present in complex biological samples at the low- to sub-fmole level (Nelson et al. *Electrophoresis* 21: 1155-1163, 2000). One technique useful in the analysis of a protein chip is surface enhanced laser desorption/ionization-time of flight-mass spectrometry (SELDI-TOF- MS) technology to characterize a protein bound to the protein chip. Alternatively, the protein chip is analysed using ESI as described in U.S. Patent Application 2002/0139751.

As will be apparent to the skilled artisan, protein chips are particularly amenable to multiplexing of detection reagents. Accordingly, several antibodies or ligands each able to specifically bind a different peptide or protein may be bound to different regions of said protein chip. Analysis of a biological sample using said chip then permits the detecting of multiple proteins of interest, or multiple B cell epitopes of the pancreatic cancer-associated protein. Multiplexing of diagnostic and prognostic markers is particularly contemplated in the present invention.

In a further embodiment, the samples are analysed using ICAT, essentially as described in US Patent Application No. 2002/0076739. This system relies upon the labeling of a protein sample from one source (i.e. a healthy individual) with a reagent and the labeling of a protein sample from another source (i.e. a tuberculosis patient) with a second reagent that is chemically identical to the first reagent, but differs in mass due to isotope composition. It is preferable that the first and second reagents also comprise a biotin molecule. Equal concentrations of the two samples are then mixed, and peptides recovered by avidin affinity chromatography. Samples are then analysed using mass spectrometry. Any difference in peak heights between the heavy and light peptide ions directly correlates with a difference in protein abundance in a biological sample. The identity of such proteins may then be determined using a method well known in the art, such as, for example MALDI-TOF, or ESI.

As will be apparent to those skilled in the art a diagnostic or prognostic assay described herein may be a multiplexed assay. As used herein the term "multiplex", shall be understood not only to mean the detection of two or more diagnostic or prognostic markers in a single sample simultaneously, but also to encompass consecutive detection of two or more diagnostic or prognostic markers in a single sample, simultaneous detection of two or more diagnostic or prognostic markers in distinct but matched samples, and consecutive detection of two or more diagnostic or prognostic markers in distinct but matched samples. As used herein the term "matched samples" shall be understood to mean two or more samples derived from the same initial biological sample, or two or more biological samples isolated at the same point in time.

Accordingly, a multiplexed assay may comprise an assay that detects several antibodies and/or epitopes in the same reaction and simultaneously, or alternatively, it may detect other one or more antigens/antibodies in addition to one or more antibodies and/or epitopes. As will be apparent to the skilled artisan, if such an assay is antibody or ligand based, both of these antibodies must function under the same conditions.

Diagnostic Assay Kits

A further aspect of the present invention provides a kit for detecting a pancreactic cancer cell in a biological sample. In one embodiment, the kit comprises:
 (i) one or more isolated antibodies that bind to a pancreatic cancer-associated protein or an immunogenic fragment or epitope thereof; and
 (ii) means for detecting the formation of an antigen-antibody complex.

In an alternative embodiment, the kit comprises:
 (i) an isolated or recombinant pancreatic cancer-associated protein or an immunogenic fragment or epitope thereof; and
 (ii) means for detecting the formation of an antigen-antibody complex.

Optionally, the kit further comprises means for the detection of the binding of an antibody, fragment thereof or a ligand to a pancreatic cancer-associated protein. Such means include a reporter molecule such as, for example, an enzyme (such as horseradish peroxidase or alkaline phosphatase), a substrate, a cofactor, an inhibitor, a dye, a radionucleotide, a luminescent group, a fluorescent group, biotin or a colloidal particle, such as colloidal gold or selenium. Preferably such a reporter molecule is directly linked to the antibody or ligand. In yet another embodiment, a kit may additionally comprise a reference sample. Such a reference sample.

In another embodiment, a reference sample comprises a peptide that is detected by an antibody or a ligand. Preferably, the peptide is of known concentration. Such a peptide is of particular use as a standard. Accordingly various known concentrations of such a peptide may be detected using a prognostic or diagnostic assay described herein.

In yet another embodiment, a kit comprises means for protein isolation (Scopes (In: Protein Purification: Principles and Practice, Third Edition, Springer Verlag, 1994).

Ribozymes may be one category of compounds useful as therapeutic agents for modulating IHoP activity. Ribozymes are RNA molecules with catalytic activity. See, e.g., Cech, Science 236, 15321539; 1987; Cech, Ann. Rev. Biochem. 59, 543568; 1990, Cech, Curr. Opin. Struct. Biol. 2, 605609; 1992, Couture & Stinchcomb, Trends Genet. 12, 510515, 1996. Ribozymes can be used to inhibit gene function by cleaving an RNA sequence, as is known in the art (e.g., Haseloff et al., U.S. Pat. No. 5,641,673). The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences.

Accordingly, another aspect of the invention pertains to using the coding sequence of a IHoP polynucleotide to generate ribozymes which will specifically bind to mRNA transcribed from the IHoP polynucleotide. Methods of designing and constructing ribozymes which can cleave other RNA molecules in trans in a highly sequence specific manner have been developed and described in the art (see Haseloff et al. Nature 334, 585591, 1988). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201).

Specific ribozyme cleavage sites within a IHoP RNA target can be identified by scanning the target molecule for ribozyme cleavage sites which include the following sequences: GUA, GUU, and GUC. Once identified, short RNA sequences of between 15 and 20 ribonucleotides corresponding to the region of the target RNA containing the cleavage site can be evaluated for secondary structural features which may render the target inoperable. Suitability of candidate IHoP RNA targets also can be evaluated by testing accessibility to hybridization with complementary oligonucleotides using ribonuclease protection assays. Longer complementary sequences can be used to increase the affinity of the hybridization sequence for the target. The hybridizing and cleavage regions of the ribozyme can be integrally related such that upon hybridizing to the target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease IHoP expression. Alternatively, if it is desired that the cells stably retain the DNA construct, the construct can be supplied on a plasmid and maintained as a separate element or integrated into the genome of the cells, as is known in the art. A ribozyme-encoding DNA construct can include transcriptional regulatory elements, such as a promoter element, an enhancer or UAS element, and a transcriptional terminator signal, for controlling transcription of ribozymes in the cells.

As taught in Haseloff et al., U.S. Pat. No. 5,641,673, ribozymes can be engineered so that ribozyme expression will occur in response to factors which induce expression of a target gene. Ribozymes also can be engineered to provide an additional level of regulation, so that destruction of mRNA occurs only when both a ribozyme and a target gene are induced in the cells.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory Press, New York (1982) and Sambrook et al., Molecular Cloning: A Laboratory Manual, Cold Spring Harbor Laboratory Press, New York (1989); Methods in Plant Molecular Biology, Maliga et al, Eds., Cold Spring Harbor Laboratory Press, New York (1995); *Arabidopsis*, Meyerowitz et al, Eds., Cold Spring Harbor Laboratory Press, New York (1994) and the various references cited therein.

RNA Interference Molecules

IHoP can be inhibited by a number of means including RNA interference. As used herein, the terms "interfering molecule" refer to all molecules, e.g., DNA, RNA or RNA-like molecules, that can affect expression of an IHoP protein. One example of ma interference molecules pertains to antisense molecules targeting an IHoP RNA transcription. Examples of other interfering RNA molecules include siRNAs, short hairpin RNAs (shRNAs), single-stranded siRNAs, microRNAs (miRNAs), and dicer-substrate 27-mer duplexes. Examples of "RNA-like" molecules include, but are not limited to, siRNA, single-stranded siRNA, microRNA, and shRNA molecules that contain one or more chemically modified nucleotides, one or more non-nucleotides, one or more deoxyribonucleotides, and/or one or more non-phosphodiester linkages. "Interfering molecules" also may include PMOs. PMOs have the same nucleic acid bases naturally found in RNA or DNA (i.e. adenine, cytosine, guanine, uracil or thymine), however, they are bound to morpholine rings instead of the ribose rings used by RNA. They may also linked through phosphorodiamidate rather than phosphodiester or phosphorothioate groups. This linkage modification eliminates ionization in the usual physiological pH range, so PMOs in organisms or cells are uncharged molecules. The entire backbone of a PMO is made from these modified subunits. Thus, siRNAs, single-stranded siRNAs, shRNAs, miRNAs, and dicer-substrate 27-mer duplexes are subsets of "interfering RNAs" or "interfering RNA molecules."

In one embodiment, siRNA molecules can be prepared against a portion of IHoP according to the techniques provided in U.S. Patent Publication 2006/0110440 and used as therapeutic compounds. As discussed above, agents can be developed to silence IHoP genes to achieve a therapeutic affect. In certain embodiments, silencing of human IHoP genes should be based on the sequences for two isoforms of the enzyme:

In some cases of pancreatic malignancies, a method of detection of IHoP may be used as an enabler for initiation of chemotherapies (including but not limited to acivicin; aclarubicin; acodazole hydrochloride; acronine; adozelesin; aldesleukin; altretamine; ambomycin; ametantrone acetate; aminoglutethimide; amsacrine; anastrozole; anthracyclin; anthramycin; asparaginase; asperlin; azacitidine (Vidaza); azetepa; azotomycin; batimastat; benzodepa; bicalutamide; bisantrene hydrochloride; bisnafide dimesylate; bisphosphonates (e.g., pamidronate (Aredria), sodium clondronate (Bonefos), zoledronic acid (Zometa), alendronate (Fosamax), etidronate, ibandornate, cimadronate, risedromate, and tiludromate); bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine (Ara-C); dacarbazine; dactinomycin; daunorubicin hydrochloride; decitabine (Dacogen); demethylation agents, dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; EphA2 inhibitors; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; histone deacetylase inhibitors (HDAC-Is) hydroxyurea; idarubicin hydrochloride; ifosfamide; ilmofosine; imatinib mesylate (Gleevec, Glivec); interleukin II (including recombinant interleukin II, or rIL2), interferon alpha-2a; interferon alpha-2b; interferon alpha-nl; interferon alpha-n3; interferon beta-I a; interferon gamma-I b; iproplatin; irinotecan hydrochloride; lanreotide acetate; lenalidomide (Revlimid); letrozole; leuprolide acetate; liarozole hydrochloride; lometrexol sodium; lomustine; losoxantrone hydrochloride; masoprocol; maytansine; mechlorethamine hydrochloride; anti-CD2 antibodies (e.g., siplizumab (Medlmmune Inc.; International Publication No. WO 02/098370, which is incorporated herein by reference in its entirety)); megestrol acetate; melengestrol acetate; melphalan; menogaril; mercaptopurine; methotrexate; methotrexate sodium; metoprine; meturedepa; mifepristone; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxaliplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; RU486; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other examples of cancer therapies include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRestM3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclix-imab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; HMG CoA reductase inhibitors (e.g., atorvastatin, cerivastatin, fluvastatin, Lescol, lupitor, lovastatin, rosuvastatin, and simvastatin); hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-iroplact; irsogladine; isobengazole; isohomohalicondrin B; itasetron; jasplakinolide; kahalalideF; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; LFA-3TIP (Biogen, Cambridge, Mass.; International Publication No. WO 93/0686 and U.S. Pat. No. 6,162,432); liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; gamma secretase inhibitors, single chain antigen binding protein; sizofuran; sobuzoxane; sodium borocaptate; sodium phenylacetate; solverol; somatomedin binding protein; sonermin; sparfosic acid; spicamycinD; spiromustine; splenopentin; spongistatin 2; squalamine; stem cell inhibitor; stemcell division inhibitors; stipiamide; stromelysin inhibitors; sulfinosine; superactive vasoactive intestinal peptide antagonist; suradista; suramin; swainsonine; synthetic glycosaminoglycans; tallimustine; 5-fluorouracil; leucovorin; tamoxifen methiodide; tauromustine; tazarotene; tecogalan sodium; tegafur; tellurapyrylium; telomerase inhibitors; temoporfm; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin;

triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; thalidomide; velaresol; veramine; verdins; verteporfin; vinorelbine; vinxaltine; anti-integrin antibodies (e.g., anti-integrin a.sub.vb.sub.3 antibodies); vorozole; zanoterone; zeniplatin; zilascorb; and zinostatin stimalamer.

In some cases of pancreatic malignancies, a method of detection of IHoP may be used as an enabler for initiation of specific embodiments of such treatments in which the agent binds specifically to the IL-3 Receptor (IL-3R). In some embodiments, the agent that binds to the EL-3R is an antibody or an antibody fragment that is specific for IL-3R. In some embodiments, the antibody or antibody fragment is conjugated either chemically or via recombinant technology to a therapeutic moiety (e.g., a chemotherapeutic agent, a plant-, fungus- or bacteria-derived toxin, a radionuclide) using a linking agent to effect a cell killing response. In certain embodiments, the antibody, antibody-conjugate, antibody fragment, or antibody fragment-conjugate binds to the .alpha.-subunit of EL-3R (i.e., the CD123 antigen). In other embodiments, the antibody, antibody-conjugate, antibody fragment, or antibody fragment-conjugate binds to the IL-3R, containing both the .alpha, and .beta, subunits. Methods for preparing antibodies to IL-3R and mimetics of antibodies to IL-3R are described in U.S. Pat. No. 6,733,743 B2, which is incorporated herein by reference in its entirety.

In some cases of pancreatic malignancies, a method of detection of IHoP may be used as an enabler for initiation of treatment with glucocorticoid receptor antagonists and their derivatives, for use as primary anti-neoplastic agents or as chemo-sensitizers for other direct anti-neoplastic treatments such as those described above. These glucocorticoid receptor antagonists and therapeutics include but are not limited to PT150 (formerly ORG34517), PT155, PT156 and PT157, PT158, PT159, PT160, PT162, PT167, TPR1, TCY1 and RU486 (also known as mifepristone).

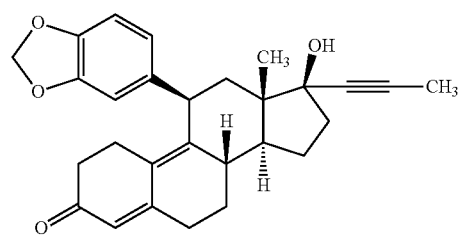
PT150

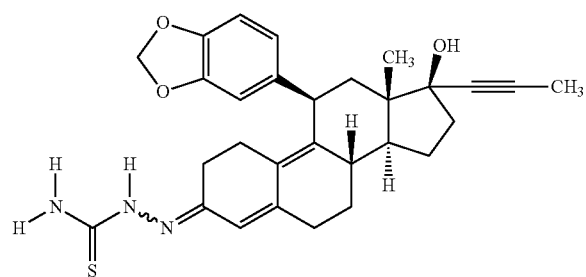
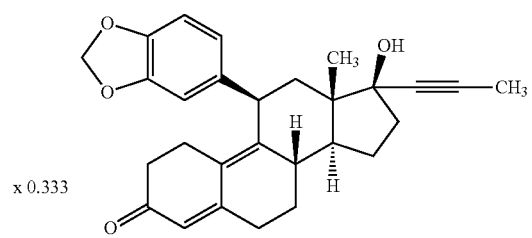
PT155
x 0.333

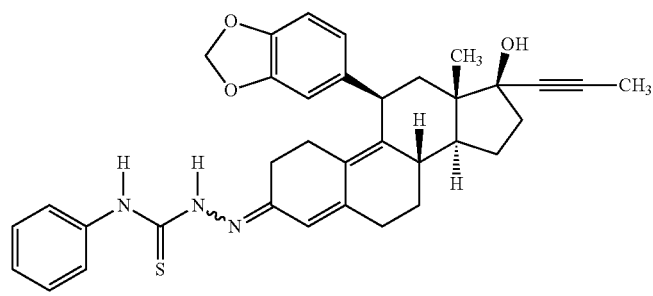
PT156
x 0.059

-continued
PT157
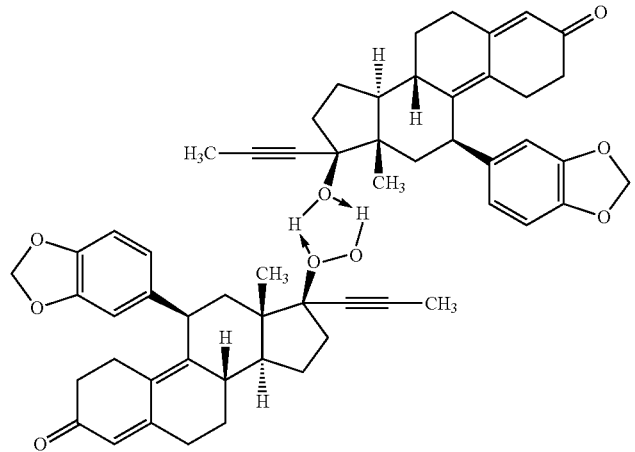
PT158
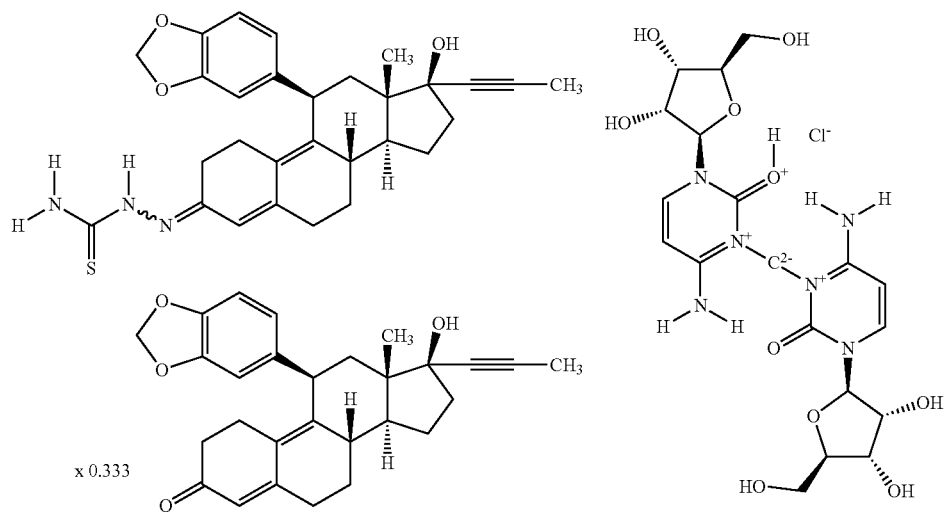
PT159
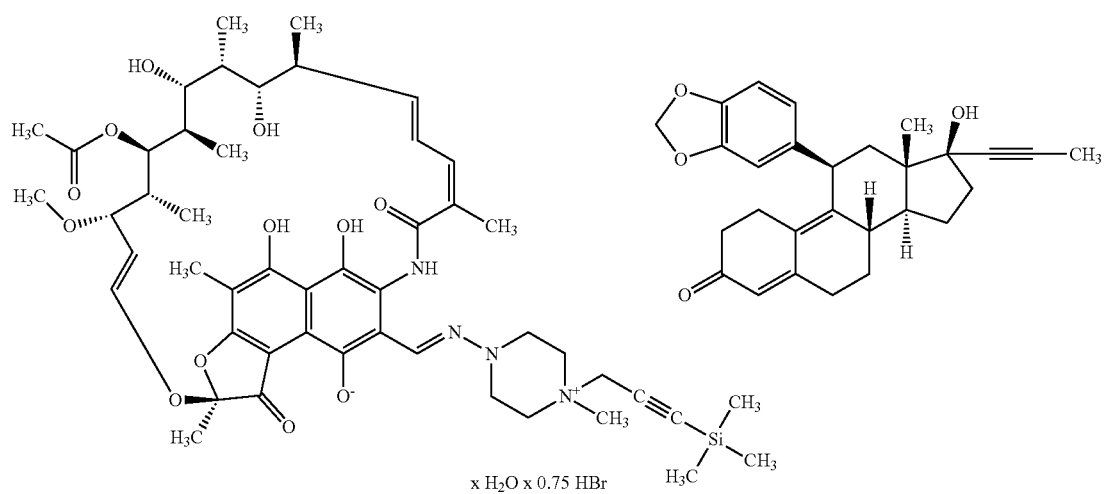

91 92
-continued
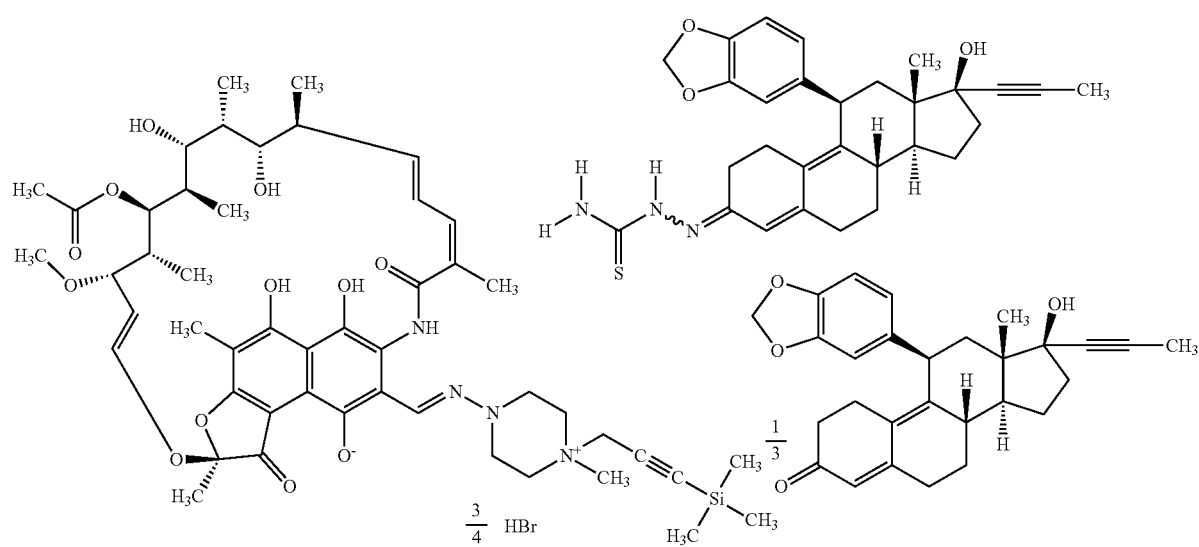
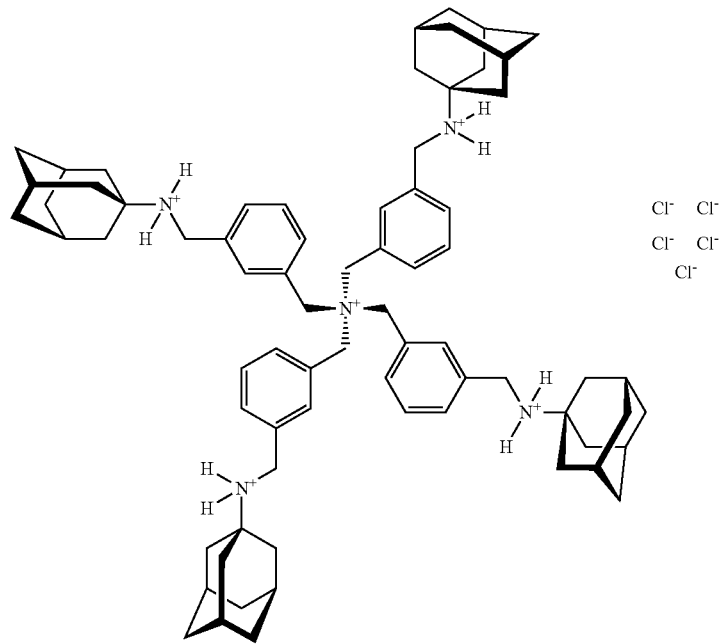

PT167
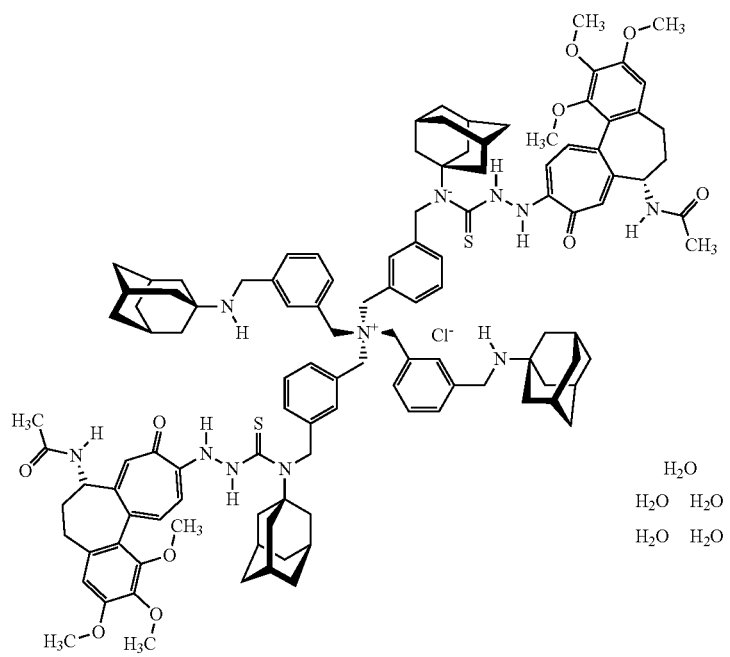
H₂O
H₂O  H₂O
H₂O  H₂O
TPR1
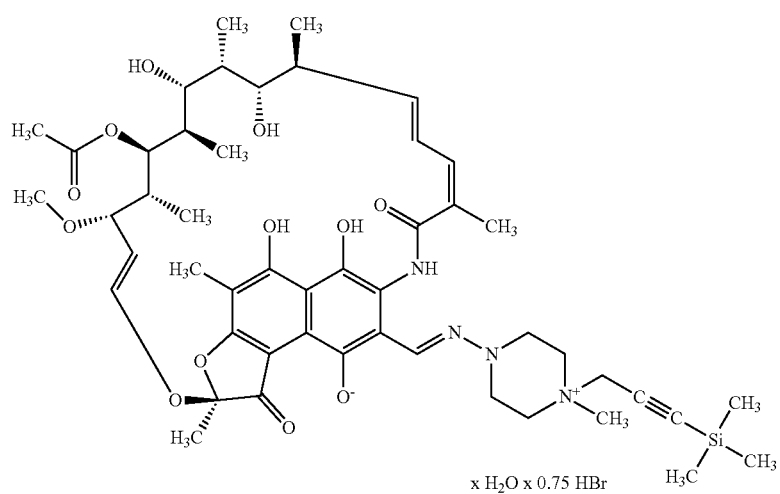
x H₂O x 0.75 HBr
TCY1
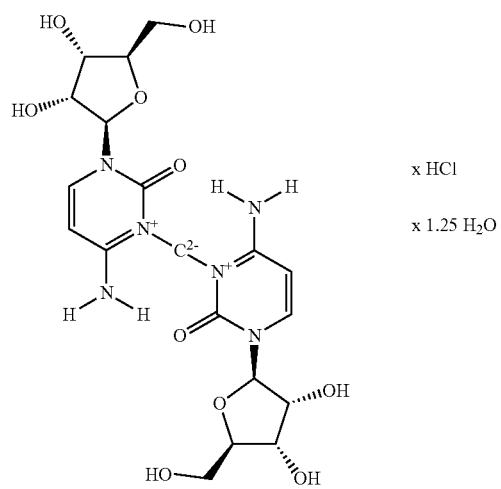
x HCl
x 1.25 H₂O While the invention has been described in detail and with reference to specific examples thereof, it will be apparent to one skilled in the art that various changes and modifications can be made therein without departing from the spirit and scope thereof.

What is claimed is:

1. A bio-artificial organ device for processing of a biological fluid for the production of a biologically active, physiologically sustainable tissue comprising:
   an inflow port for ingress of a biological fluid;
   a distribution chamber which optionally includes a pump;
   at least one column in fluid communication with the distribution chamber having a cap wherein said at least one column can receive biological fluid flow from the inflow port, wherein said at least one column comprises a decellularized, de-vitalized extracellular matrix derived from a non-micro organ source selected from the group consisting of either neonatal porcine or human liver, adult porcine or human liver, neonate porcine or human pancreas, adult porcine or human pancreas, and combinations thereof, further wherein said at least one column comprises a living cellular component selected from the group consisting of hepatocytes, hepatobiliary progenitor cells, hepatobiliary stem cells, pancreatic islet beta cells, pancreatic stem cells, and combinations thereof;
   wherein said column has one or more sensors that monitor said column for metabolic and functional activity;
   wherein when there are more than one column, the columns are independent from each other;

a holding device surrounding an entirety of an axial surface of the at least one column and configured so as to allow insertion into the holding device and removal from the holding device of the at least one column, and wherein the at least one column is attached to the distribution cap with a column connector;

a sealingly closeable outer casing;

a thermal control system including a thermos-pouch encasing the bio-artificial organ which maintains the device at an optimal temperature for the cells within the device;

the function of the bio-artificial organ may be controlled by control units selected from the group consisting of dedicated sensors, micro-controllers, wireless communication systems, micro actuators, contactless identification tags and combinations thereof;

an outflow port for egress of a biological fluid, wherein said bio-artificial organ conducts and processes said biological fluid; and the device is adapted to hold approximately 500-700 grams of cellularized tissue in order to provide sufficient tissue function to keep the body in homeostasis.

2. The bio-artificial organ device of claim 1 for processing of a biological fluid, comprising:

an apparatus external to a patient which is in communication with the one or more sensors and wherein the external apparatus is selected from the group consisting of one or more of a display, monitor, printer, computer, wireless device and global positioning device;

wherein the device is configured to be implanted in a patient;

a living cellular compound selected from the group consisting of cells from human, porcine, or other mammals, and combinations thereof; and the living cellular component is derived from a source selected from the group consisting of fetal human liver, neonatal human liver, fetal pediatric human liver, teenage human liver, adult human liver, fetal human pancreas, neonatal human pancreas, pediatric human pancreas, teenage human pancreas, adult human pancreas, cultured human hepatocytes, cultured human beta cells, stem cells derived hepatocytes, stem cells derived beta cells, human pancreatic stem cells, adult or pediatric human hepatobiliary stem cells, adult or pediatric human hepatobiliary progenitor cells and combinations thereof; or from the group consisting of fetal porcine liver, neonatal porcine liver, fetal pediatric porcine liver, teenage porcine liver, adult porcine liver, fetal porcine pancreas, neonatal porcine pancreas, pediatric porcine pancreas, teenage porcine pancreas, adult porcine pancreas, cultured porcine hepatocytes, cultured porcine beta cells, stem cells derived hepatocytes, stem cells derived beta cells, porcine pancreatic stem cells, adult or pediatric porcine hepatobiliary stem cells, adult or pediatric porcine hepatobiliary progenitor cells or combinations thereof.

3. The bio-artificial organ device of claim 1 for processing a biological fluid, wherein the one or more sensors are capable of wireless communication;

the biological fluid is blood or plasma;

the inflow port and outflow ports are attached to a central blood line configured to recirculate blood to the subject;

the device contains units selected from the group consisting of an independent redundant battery power system, a hydraulic system, the thermal control system, and combinations thereof; and the thermal control system keeps the bio-artificial organ at a constant temperature;

the one or more sensors can be used to monitor blood values before and after the columns selected from the group consisting of including but not limited to glucose levels, electrolytes, sodium, potassium, chloride, bicarbonate, pH, oxygenation level, ammonia level, lipid levels, the speed and cumulative volume of flow of the blood, temperature, blood pressure, and combinations thereof; and the one or more sensors can be used to monitor blood values selected from the group consisting of hematocrit, iron saturation concentration, red blood cell balance, and combinations thereof;

the one or more sensors can alert clinical staff overseeing the use of the devices for deviations from normal that may require adjustment of the device or additional diagnostics or therapeutic adjustments for the patient;

the one or more sensors can detect identified toxins selected from the group consisting of prescription medications, over the counter medications, herbal remedies, dietary supplements, ingested or topical toxins, environmental toxins, bio-threats, chemical weapon threats, and combinations thereof;

the one or more sensors can detect infectious agents selected from the group consisting of bacterial, viral, fungal, parasitic, and combinations thereof;

the one or more sensors can detect molecular or cellular breakdown of infectious agents selected from the group consisting of endotoxins, organism membrane fragments, membrane associated vesicles, and combinations thereof;

the device has a central blood line out and a central blood line in;

the blood flow can be arterial derived, venous derived, and combinations thereof;

the blood flow can come from an implanted or surgically created fistula, the venous blood flow is propelled by gravitational force and low pressure of the venous system; and the arterial blood flow is propelled through arterial blood pressure with or without gravitational force.

4. The bio-artificial organ device of claim 1 for processing of a biological fluid, wherein the matrix has a thickness of at least about 1 millimeter.

* * * * *